(12) United States Patent
Hurst et al.

(10) Patent No.: US 6,187,905 B1
(45) Date of Patent: Feb. 13, 2001

(54) ALPHA-KETOAMIDE DERIVATIVES

(75) Inventors: David Nigel Hurst, Welwyn; Philip Stephen Jones, Welwyn Garden City; Paul Brittain Kay, Baldock; Tony Michael Raynham, Datchet; Francis Xavier Wilson, Welwyn Garden City, all of (GB)

(73) Assignee: Hoffmann-La Roche Inc., Nutley, NJ (US)

( * ) Notice: Under 35 U.S.C. 154(b), the term of this patent shall be extended for 0 days.

(21) Appl. No.: 09/305,030

(22) Filed: May 4, 1999

(30) Foreign Application Priority Data

May 6, 1998 (GB) .................................................. 9809664

(51) Int. Cl.⁷ ..................................................... C07K 7/06
(52) U.S. Cl. ............................................. 530/329; 514/17
(58) Field of Search ............................... 514/17; 530/329

(56) References Cited

FOREIGN PATENT DOCUMENTS

| WO 98/17679 | 4/1998 | (WO) . |
| WO 99/07733 A2 | 2/1999 | (WO) . |
| WO 99/07733 A3 | 2/1999 | (WO) . |
| WO 99/07734 A2 | 2/1999 | (WO) . |
| WO 99/07734 A3 | 2/1999 | (WO) . |

OTHER PUBLICATIONS

Ogilvie, et al., Peptidomimetic Inhibitors of the Human Cytomegalovirus Protease, J. Med. Chem., vol. 40, pp. 4113–4135 (1997).

Primary Examiner—Christopher S. F. Low
Assistant Examiner—David Lukton
(74) Attorney, Agent, or Firm—George W. Johnston; William H. Epstein

(57) ABSTRACT

The invention relates to α-ketoamides of the general formula

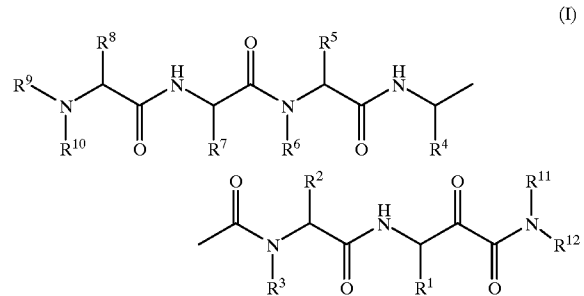

(I)

wherein $R^1$ to $R^{12}$ have the significances given in the description, and their salts. The α-ketoamide derivatives provided by the present invention inhibit proteinases of viral origin, such as HCV protease, and can be used in the treatment of viral infections, especially viral infections caused by hepatitis C, hepatitis G and human GB viruses.

320 Claims, No Drawings

ALPHA-KETOAMIDE DERIVATIVES

BACKGROUND OF THE INVENTION

The present invention is concerned with α-ketoamide derivatives and a process for their manufacture. The invention is also concerned with pharmaceutical preparations containing these derivatives and with the use of these derivatives as medicaments, especially antiviral medicaments.

SUMMARY OF THE INVENTION

The α-ketoamide derivatives provided by the present invention are compounds of the general formula

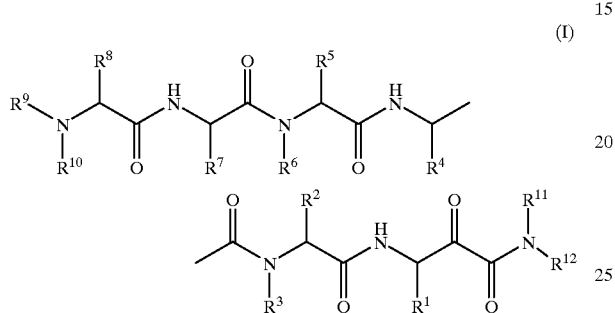

(I)

wherein
- $R^1$ represents lower alkyl, halo-lower alkyl, cyano-lower alkyl, lower alkylthio-lower alkyl, aryl-lower alkylthio-lower alkyl, aryl-lower alkyl, heteroaryl-lower alkyl, lower alkenyl, or lower alkynyl;
- $R^2$ represents lower alkyl, hydroxy-lower alkyl, carboxy-lower alkyl, aryl-lower alkyl, aminocarbonyl-lower alkyl, lower cycloalkyl-lower alkyl, aryl-lower alkoxy-aryl-lower alkyl, heteroaryl-lower alkyl, or dihalo aryl lower alkoxy aryl-lower alkyl;
- $R^3$ represents hydrogen or lower alkyl;
- $R^2$ and $R^3$ together form a cyclic bridge selected from the group consisting of —$CH_2$—$CH_2$—, —$CH_2$—$CH_2$—$CH_2$—, —CHOH—$CH_2$—, —$CH_2$—CHOH—, —$CH_2$—$CH_2$—CHOH—, —$CH_2$—CHOH—$CH_2$—, and —CHOH—$CH_2$—$CH_2$—;
- $R^4$ represents lower alkyl, hydroxy-lower alkyl, lower cycloalkyl-lower alkyl, carboxy-lower alkyl, aryl-lower alkyl, aryl-lower alkoxy-aryl-lower alkyl, aryl-lower alkoxy-lower alkyl, aryl-lower alkoxycarbonyl-lower alkyl, lower alkylthio-lower alkyl, cyano-lower alkylthio-lower alkyl, aryl-lower alkylthio-lower alkyl, lower alkenyl, aryl, heteroaryl-lower alkyl, arylsulphonyl-guanidino-lower alkyl, acetamidothio-lower alkyl, lower alkylcarbonylamino-lower alkyl, formamido-lower alkyl, or lower cycloalkyl;
- $R^5$ represents lower alkyl, hydroxy-lower alkyl, lower alkylthio-lower alkyl, aryl-lower alkyl, aryl-lower alkylthio-lower alkyl, cyano-lower alkylthio-lower alkyl, lower cycloalkyl, lower cycloalkyl-lower alkyl, aryl-lower alkoxycarbonyl-lower alkyl, aryl-lower alkoxy-aryl-lower alkyl, aryl, arylsulphonyl-guanidino-lower alkyl, aryl-lower alkoxy-lower alkyl, heteroaryl-lower alkyl, or formamido-lower alkyl;
- $R^6$ represents hydrogen or lower alkyl;
- $R^7$ represents hydrogen, lower alkyl, carboxy-lower alkyl, hydroxy-lower alkyl, aryl-lower alkyl, lower cycloalkyl-lower alkyl, lower cycloalkyl, aryl, heteroaryl-lower alkyl, nitroguanidino-lower alkyl, aryl-lower alkoxy-lower alkyl, aryl-lower alkylthio-lower alkyl, aryl-lower alkoxycarbonyl-lower alkyl, arylsulphonylguanidino-lower alkyl, acetamidothio-lower alkyl, lower alkylsulphonyl-lower alkyl, heteroaryl-lower alkyl, aryl-lower alkoxy-aryl-lower alkyl, aryl-lower alkoxy-heteroaryl-lower alkyl, lower alkylcarbonyloxy-lower alkyl, lower alkylcarbonylamino-lower alkyl, aryl-lower alkyl-heteroaryl-lower alkyl, lower alkenyloxycarbonyl-lower alkyl, lower alkylthio-lower alkyl, formamido-lower alkyl, or nitro substituted aryl-lower alkyl;
- $R^8$ represents lower alkyl, lower cycloalkyl, lower cycloalkyl-lower alkyl, carboxy-lower alkyl, hydroxy-lower alkyl, hydroxy substituted aryl-lower alkyl, aryl-lower alkyl, mercapto-lower alkyl, lower alkylsulphonyl-lower alkyl, aryl-lower alkoxy-lower alkyl, aryl-heteroaryl-lower alkyl, aryl-lower alkoxy-aryl-lower alkyl, nitroguanidino-lower alkyl, aryl, acetamidothio-lower alkyl, aryl-sulphonylguanidino-lower alkyl, aminocarbonyl-lower alkyl, aryl-lower alkoxy-lower alkyl-heteroaryl-lower alkyl, lower alkylsulphinyl-lower alkyl, lower alkylaminocarbonyl-lower alkyl, heteroaryl-lower alkyl, lower alkylthio-lower alkyl or formamido-lower alkyl; and
- $R^9$ represents hydrogen or lower alkyl; or
- $R^8$ and $R^9$ together form a cyclic bridge selected from the group consisting of —$CH_2$—$CH_2$—, $CH_2$—, —$CH_2$—S—$CH_2$—, —$CH_2$—$CH_2$—S—, and —S—$CH_2$—$CH_2$—;
- $R^{10}$ represents lower alkylcarbonyl, carboxy-lower alkylcarbonyl, arylcarbonyl, lower alkoxycarbonyl, aryl-lower alkoxycarbonyl, aryl-lower alkylcarbonyl, heteroaryl-lower alkylcarbonyl, arylamino-carbonyl-lower alkylcarbonyl, heteroarylthio-lower alkylcarbonyl, heteroarylcarbonyl, hydroxyfluorenylcarbonyl, heteroarylcarbonyl-lower alkylcarbonyl, lower alkoxy-lower alkylcarbonyl, arylcarbonyl-lower alkylcarbonyl, lower alkoxy-lower alkoxy-lower-alkoxy-lower alkylcarbonyl, arylcarbonyl-amino-lower alkylcarbonyl, heterocyclylcarbonyl, lower alkyl-carbonyloxy-lower alkylcarbonyl, aryloxy-lower alkylcarbonyl, lower alkynylcarbonyl, lower cyclo alkylcarbonyl, di(lower alkyl)amino-lower alkylcarbonyl, aryl-lower alkoxycarbonylamino-lower alkylcarbonyl, lower alkoxy-lower alkylcarbonyl, lower alkylcarbonylamino-lower alkenylcarbonyl, heterocyclyl-lower alkylcarbonyl, lower alkylthio-lower alkylcarbonyl, lower alkoxycarbonyl-lower alkylcarbonyl, aryl-lower alkenylcarbonyl, lower cycloalkenylcarbonyl, di(lower alkyl)aminocarbonyl-lower alkylcarbonyl, halo-lower alkylcarbonyl, lower alkenylcarbonyl, lower alkylcarbonylamino-lower alkylcarbonyl, lower cycloalkyl-lower alkylcarbonyl, lower alkylsulphonyl, arylsulphonyl arylaminocarbonyloxy-lower alkylcarbonyl, lower alkylsulphonyl-lower alkylcarbonyl, lower alkylcarbonyl-lower alkylcarbonyl, hydroxy-halo-lower alkylcarbonyl, di(lower alkoxy)phosphinyl-lower alkylcarbonyl, mono or di (lower alkylamino) lower alkyl carbonyl, mono or di (lower alkyl) amino substituted arylcarbonyl, lower alkoxy lower cycloalkylcarbonyl, lower alkyl substituted arylcarbonyl lower alkylcarbonyl, cyclo lower alkylcarbonyl, aryl substituted cyclo lower alkyl carbonyl, or nitro substituted aryl-lower alkylcarbonyl; and $R^{11}$ and $R^{12}$ each individually represent hydrogen, lower alkyl, aryl, heteroaryl, aryl-lower alkyl, diaryl-lower alkyl, lower cycloalkyl-lower alkyl, lower alkylaminocarbonyl-lower alkyl, lower alkylthio-lower alkyl, lower alkoxy, hydroxy, lower alkoxy substituted aryl-lower alkyl, nitro substituted aryl lower alkyl, hydroxy substituted aryl lower alkyl or hydroxylower alkyl substituted aryl lower alkyl and heteroaryl-lower alkyl;

and salts thereof.

The α-ketoamide derivatives provided by the present invention inhibit proteinases of viral origin, such as HCV protease, and can be used in the treatment of viral infections, especially viral infections caused by hepatitis C, hepatitis G and human GB viruses.

DETAILED DESCRIPTION OF THE INVENTION

As used herein, the term "lower alkyl" denotes a straight-chain or branched-chain alkyl group containing 1–7, preferably 1–4, carbon atoms, e.g. methyl, ethyl, propyl, isopropyl, n-butyl, isobutyl, sec.butyl, tert.butyl, n-pentyl, neopentyl and the like. The term "lower alkenyl" denotes a straight-chain or branched-chain alkenyl group containing 2–7 carbon atoms, e.g. vinyl, allyl, n-propenyl, n-butenyl and the like, and the term "lower alkynyl" denotes a straight-chain or branched-chain alkynyl group containing 2–7 carbon atoms, e.g. propargyl, 5-hexynyl, 6-heptynyl and the like. The term "lower cycloalkyl" denotes a cycloalkyl group which contains 3–7 carbon atoms, i.e. cyclopropyl, cyclobutyl, cyclopentyl, cyclohexyl and cycloheptyl, and which can be unsubstituted or substituted, e.g. by halo, lower alkyl, lower alkoxy or lower alkyl-carbonyl. The term "lower cycloalkenyl" denotes a cycloalkenyl group containing 3–7 carbon atoms, i.e. cyclopropenyl, cyclobutenyl, cyclopenteny, cyclohexenyl and cycloheptenyl. The term "lower alkoxy" denotes a lower alkyl group as defined hereinbefore, which is bonded via an oxygen atom, e.g. methoxy, ethoxy, n-propoxy, isopropoxy, n-butoxy, isobutoxy, tert.butoxy and the like. The term "aryl" denotes a monocyclic or polycyclic aromatic group, e.g. phenyl, naphthyl or the like, which is unsubstituted or substituted by one or more substituents selected from e.g. lower alkyl, nitro, lower alkoxy, halo, hydroxy, hydroxy-lower alkyl, e.g. hydroxymethyl, halo-lower alkyl, e.g. trifluoromethyl or other groups such as lower alkyl amino (such as dimethyl amino) and sulphamoyl and acetamido groups. The term "heteroaryl" denotes a 5- or 6-membered aromatic heterocyclic ring, heterocyclic rings contain one or two heteroatoms, which may be the same or different that contain N, O and S as the heteroatom(s) and which is optionally benz-fused and/or optionally substituted in the same manner as the aryl group defined hereinbefore. furyl, thienyl, oxazolyl, pyridyl, pyrimidinyl, benzofuranyl, benzo-thienyl, quinolyl, isoquinolyl, indolyl and the like are examples of heteroaryl groups. The term "heterocyclyl" denotes a saturated or partly unsaturated, 5- or 6-membered heterocyclic ring, the heterocyclic ring contains one or two heteroatoms, which may be the same or different, which include N, O, and S as the hetero atom(s), and, which is optionally benz-fused and/or optionally substituted in the same manner as the aryl group defined hereinbefore and/or by oxo and/or thioxo. Examples of heterocyclyl are thiazolidinyl, 1,2,3,4-tetrahydropyrimidinyl, hexahydropyrimidinyl, 5,6-dihydropyranyl and the like. The term "halo" means fluoro, chloro, bromo or iodo. It will be appreciated that the aforementioned definitions apply to the respective groups when they stand-alone or are combined with a further group or groups.

In the compounds provided by the present invention $R^1$ preferably represents represent lower alkyl, especially butyl, halo-lower alkyl, especially fluoro-lower alkyl and particularly 2,2,2-trifluoroethyl, lower alkenyl or lower alkynyl. Preferably, $R^2$ represents lower alkyl, especially isobutyl, or lower cycloalkyl-lower alkyl and $R^3$ represents hydrogen. $R^4$ preferably represents lower alkyl, especially tert.butyl, aryl or lower cycloalkyl. $R^5$ preferably represents lower alkyl, aryl-lower alkyl, especially (2-methylphenyl)-methyl, lower cycloalkyl or lower cycloalkyl-lower alkyl. $R^6$ preferably represents hydrogen. $R^7$ preferably represents lower alkyl, especially isobutyl, carboxy-lower alkyl, especially 2-carboxyethyl, aryl-lower alkyl, nitroguanidino-lower alkyl, aryl-lower alkoxy-lower alkyl, especially benzyloxymethyl, or lower cycloalkyl. Preferably, $R^8$ represents carboxy-lower alkyl, especially carboxymethyl, hydroxy-lower alkyl, especially hydroxymethyl, aryl-lower alkyl, aryl-heteroaryl-lower alkyl or heteroaryl-lower alkyl and $R^9$ represents hydrogen. $R^{10}$ preferably represents lower alkylcarbonyl, carboxy-lower alkylcarbonyl, especially 3-carboxypropionyl, aryl-lower alkoxycarbonyl, heteroaryl-lower alkylcarbonyl, heteroarylcarbonyl, hydroxyfluorenylcarbonyl, heteroarylcarbonyl-lower alkylcarbonyl, heterocyclylcarbonyl, halo-lower alkylcarbonyl, lower alkylcarbonylamino-lower alkylcarbonyl or lower cycloalkyl-lower alkylcarbonyl. Preferably, $R^{11}$ and $R^{12}$ each individually represent hydrogen, lower alkyl or aryl-lower alkyl, especially hydrogen.

Examples of preferred compounds of formula I are:

3(RS)-[[N-[N-[N-[N-[N-(3-Carboxypropionyl)-L-α-aspartyl]-L-α-glutamyl]-2-methyl-L-phenylalanyl]-3-methyl-L-valyl]-L-leucyl]amino]-5,5,5-trifluoro-N-[1(S)-2-naphthyl)ethyl]-2-oxovaleramide, 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-2-oxo-N-(1(S)-phenylpropyl)valeramide, 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-N-(2-methyl-1(S)-phenylpropyl)-2-oxovaleramide, 3(R or S)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-2-oxovaleramide, 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-N-(4-hydroxybenzyl)-2-oxovaleramide, 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-N-(3-methoxybenzyl)-2-oxovaleramide, 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-N-(α(S)-methylbenzyl)-2-oxovaleramide, N-benzyl-3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-2-oxovaleramide, 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-N-[1(S)-2-naphthyl)ethyl]-2-oxovaleramide and 3(S)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-2-oxoheptanamide.

Acidic compounds of formula I form salts with bases, e.g. alkali metal salts such as sodium or potassium salts, alkaline earth metal salts such as calcium or magnesium salts, salts with organic bases, e.g. salts with amines such as N-ethyl-piperidine, procaine or dibenzyl-amine, or salts with basic amino acids such as salts with arginine or lysine. Compounds of formula I which are basic form salts with inorganic acids, e.g. hydrochloric acid, hydrobromic acid, nitric acid, phosphoric acid, sulphuric acid, etc. and with organic acids, acetic acid, citric acid, fumaric acid, tartaric acid, malic acid, maleic acid, salicylic acid, methane-sulphonic acid, p-toluenesulphonic acid etc.

According to the process provided by the present invention, the compounds of formula I hereinbefore and their salts are manufactured by a) condensing an acid addition salt of an amine of the general formula

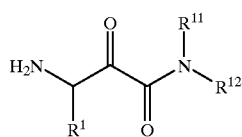
(II)

wherein $R^1$, $R^{11}$ and $R^{12}$ have the significance given earlier,
with an acid of the general formula

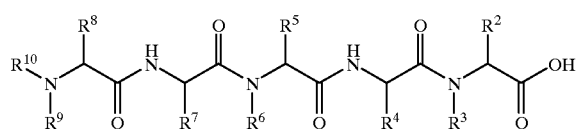
(III)

wherein $R^2$, $R^3$, $R^4$, $R^5$, $R^6$, $R^7$, $R^8$, $R^9$ and $R^{10}$ have the significance
given earlier, provided that any carboxy, and/or aminocarbonyl group(s) present is/are in protected form,
and, where required, cleaving off any protecting group(s) present in the condensation product obtained, or b) oxidizing an α-hydroxyamide of the general formula c) if desired, converting a compound of formula I obtained into a salt.

Protected carboxy, hydroxy and aminocarbonyl groups present in the starting materials of formulae II, III and IV are, respectively, carboxy, hydroxy and aminocarbonyl groups protected with a protecting group that is known per se from peptide chemistry. Thus, for example, carboxy can be protected as tert-butoxycarbonyl, hydroxy can be protected as the O-tert-butyl or benzyl ether and aminocarbonyl can be protected as tritylaminocarbonyl.

The condensation of an acid addition salt of an amine of formula II with an acid of formula III in accordance with embodiment a) of the process provided by the invention can be carried out in a manner known per se in peptide chemistry for the formation of an amide bond. In a preferred embodiment an acid addition salt, especially the p-toluene-sulphonate, of an amine of formula II is condensed with an acid of formula III in the presence of 1-(3-dimethylaminopropyl)-3-ethylcarbodiimide (EDAC), 1-hydroxybenzotriazole (HOBT) and N-ethyl-morphine (NEM) in an inert organic solvent, e.g. a halogenated hydrocarbon such as dichloro-methane, at room temperature. In a convenient embodiment the acid addition salt of the amine of formula (II) is not purified following its preparation (described hereinafter), but is condensed in crude form with an acid of formula III.

Any protecting groups present in the condensation product obtained can be cleaved off according to methods known per se in peptide chemistry. For example, tert-butoxycarbonyl is converted into carboxy, tert-butyl ether is converted into hydroxy and tritylaminocarbonyl is converted into aminocarbonyl by treatment with acid under standard conditions. A benzyl ether is converted into hydroxy by hydrogenolysis in a known manner.

The oxidation of an α-hydroxyamide of formula III in accordance with embodiment b) of the process provided by the invention is preferably carried out under the conditions of the Dess-Martin oxidation [J. Org. Chem. 48, 4155 (1983)]. Thereby, an α-hydroxyamide of formula III is dissolved in an inert organic solvent such as dimethylformamide and oxidized with 1,1,1-triacetoxy-1,1-dihydro-1,2-benziodoxol-3(1H)-one at room temperature.

The subsequent cleavage of any hydroxy protecting group present in the oxidation product can be carried out in an analogous manner to that described earlier in connection with the cleavage of a hydroxy protecting group from the condensation product obtained according to embodiment a) of the process.

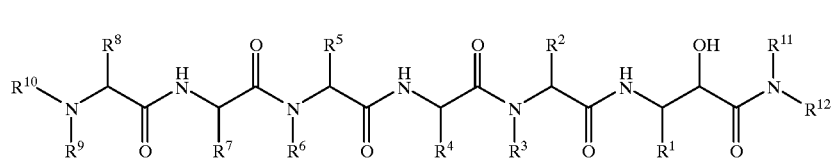
(IV)

wherein $R^1$, $R^2$, $R^3$, $R^4$, $R^5$, $R^6$, $R^7$, $R^8$, $R^9$, $R^{10}$, $R^{11}$ and $R^{12}$ have the significance given earlier, provided that any hydroxy group(s) present is/are in protected form,
and, where required, cleaving off any protecting group(s) present in the condensation product obtained,
and According to a variant of embodiment b) of the process provided by the invention, the oxidation of an α-hydroxyamide of formula IV is carried out while the latter is bonded to a solid phase synthesis resin and the product is cleaved from the resin by treatment with acid. In particular, the resin-bonded α-hydroxyamide preferably has the general formula

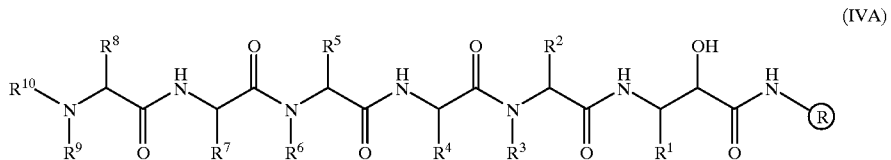

(IVA)

wherein $R^1$, $R^2$, $R^3$, $R^4$, $R^5$, $R^6$, $R^7$, $R^8$, $R^9$, $R^{10}$, $R^{11}$ and $R^{12}$ have the significance given earlier, provided that any hydroxy group(s) present is/are in protected form, and R represents a group of the formula

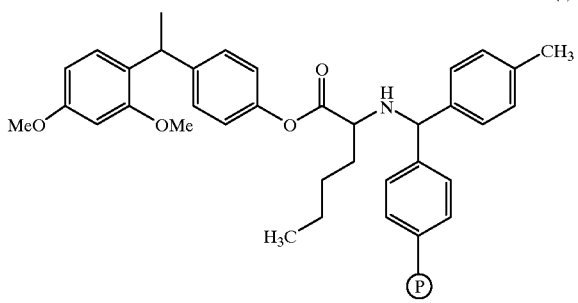

(a)

in which P represents a copoly(styrene/1% divinylbenzene) polymer matrix.

Following the oxidation, treatment of the product with acid, e.g. trifluoroacetic acid, results in cleavage from the resin and concomitant removal of any hydroxy protecting group(s) which may be present.

According to embodiment c) of the process provided by the invention a compound of formula I is converted into a salt. Thus, basic compounds of formula I are converted into salts with bases by treatment with a base and acidic compounds of formula I are converted into acid addition salts by treatment with an acid. Suitable bases and acids are those which give the base salts and acid addition salts specifically referred to herein before.

The acid addition salts of the amines of formula II used as starting materials in embodiment a) of the process provided by the invention are novel and also form an object of the present invention. They can be prepared, for example, as illustrated in Scheme 1 hereinafter in which $R^1$, $R^{11}$ and $R^{12}$ have the significance given earlier, provided that any hydroxy group(s) present is/are in protected form, and Boc represents tert-butoxycarbonyl.

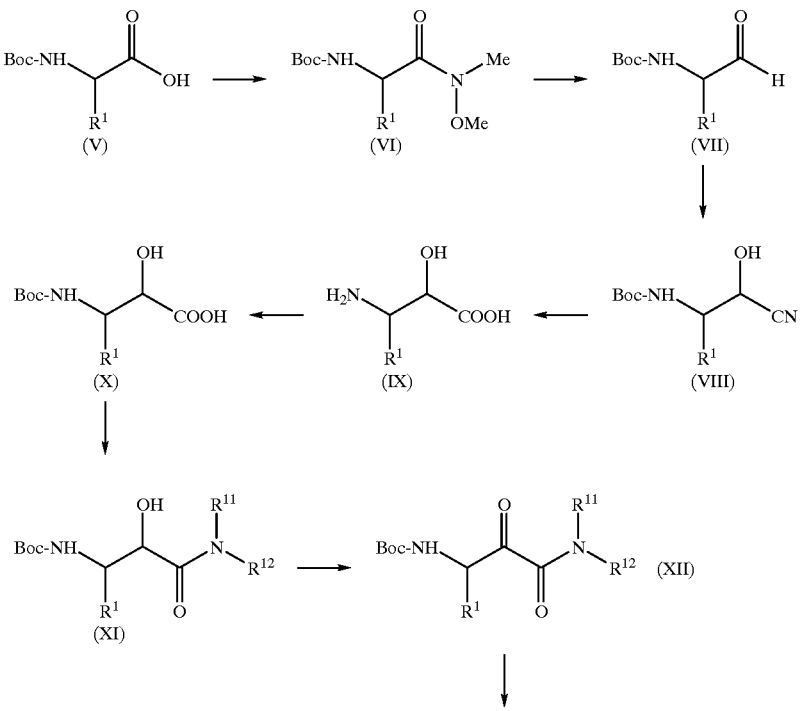

Scheme 1

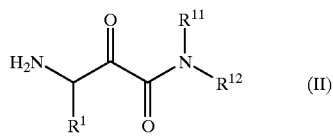

Having regard to Scheme 1, in the first stage an N-Boc protected amino acid of formula V, which is a known compound or an analogue of a known compound, is reacted with a N,O-dimethylhydroxylamine salt, especially the hydrochloride, in a known manner, e.g. in the presence of EDAC, HOBT and NEM and in an inert organic solvent, e.g. an ether such as tetrahydrofuran, at room temperature. The resulting N,O-dimethyl hydroxamate of formula VI is then reduced according to known methods, expediently using an alkali metal aluminum hydride, especially lithium aluminum hydride, to an aldehyde of formula VII. In the next stage an aldehyde of formula VII is reacted with acetone cyanohydrin in the presence of an organic base, especially a tri(lower alkyl)amine such as triethylamine, and in an inert organic solvent, e.g. a chlorinated aliphatic hydrocarbon such as dichloromethane, at room temperature. The resulting hydroxynitrile of formula VIII is subsequently treated, optionally without purification, with an acid, especially a hydrohalic acid and particularly hydrochloric acid, at an elevated temperature, suitably at reflux, to give a corresponding salt of a hydroxyacid of formula IX. This salt, optionally without purification, is treated in the next stage with di-tert-butyl dicarbonate in a conventional manner, e.g. in the presence of an inorganic base such as an alkali metal bicarbonate, e.g. sodium bicarbonate, in an inert solvent system, e.g. aqueous dioxan, at room temperature, there being thus obtained a N-Boc protected hydroxy-carboxylic acid of formula X. Condensation of an acid of formula X with an amine of the formula $HNR^{11}R^{12}$ in a manner known per se, e.g. in the presence of EDAC and HOBT and in an inert organic solvent such as a halogenated aliphatic hydrocarbon, e.g. dichloromethane, at room temperature, gives an α-hydroxyamide of formula XI. In the next stage an α-hydroxyamide of formula XI is oxidized, conveniently in a manner analogous to that described earlier in connection with embodiment b) of the process provided by the invention, to give an α-ketoamide of formula XII. Finally, an α-ketoamide of formula XII is converted into an acid addition salt of a compound of formula II by treatment with acid, especially p-toluenesulphonic acid. This is conveniently carried out by dissolving the respective salt and acid in an inert organic solvent, e.g. acetonitrile, by heating, then cooling to room temperature and stirring.

An alternative route to 3(S)-(tert-butoxyformamido)-2(S)-hydroxy-alkanoic acids of formula X in which $R^1$ represents lower alkyl is illustrated in Scheme 2 hereinafter in which $R^{1a}$ represents lower alkyl, Ph represents phenyl Boc represents tert-butoxycarbonyl and tBu represents tert-butyl.

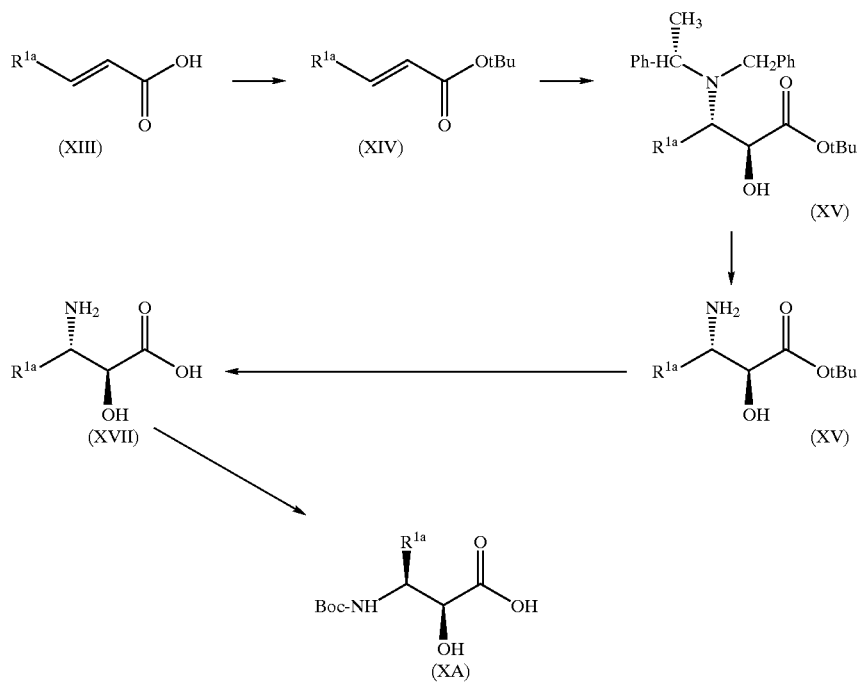

In the first stage of Scheme 2, an (E)-alkenoic acid of formula XIII, which is a known compound, is converted into the corresponding tert-butyl ester of formula XIV by reaction with N,N-dimethylformamide di(tert-butyl) acetal in an inert organic solvent, e.g. an aromatic hydrocarbon such as benzene or toluene, at an elevated temperature, e.g. about 80° C. An ester of formula XIV is then reacted firstly with (S)-(−)-N-benzyl-α-methylbenzylamine (previously activated with a lower alkyl-lithium compound such as n-butyllithium) and then with (1S)-(+)-(camphorylsulfonyl) oxaziridine, with these reactions being carried out in an inert organic solvent, e.g. an aliphatic ether such as diethyl ether or a cyclic ether such as tetrahydrofuran, at a low temperature, e.g. about −78° C. There is thus obtained a compound of formula XV that is hydrogenolyzed in a manner known per se, e.g. in the presence of a palladium/carbon catalyst, to give an amino-hydroxyalkanoate of formula XVI. This amino-hydroxyalkanoate is then de-esterified by treatment with an appropriate acid, especially trifluoroacetic acid, to give an acid addition salt of an amino-hydroxyalkanoic acid of formula XVII. Finally, treatment of this amino-hydroxyalkanoic acid of formula XVII with di-tert-butyl dicarbonate gives a 3(S)-(tert-butoxyformamido)-2(S)-hydroxy-alkanoic acid of formula XA, with the treatment being carried out in an analogous manner to that described in Scheme 1 for the conversion of a compound of formula IX into a compound of formula X.

The acids of formula III used as starting materials in embodiment a) of the process provided by the invention are novel. They can be prepared, for example, starting from a compound of the general formula

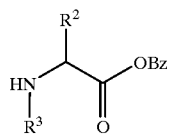

(XVIII)

wherein $R^2$ and $R^3$ have the significance given earlier, provided
that any carboxy, hydroxy or aminocarbonyl group present is in protected form,
and Bz represents benzyl.

Thus, a compound of formula XVIII can be sequentially coupled with respective amino acids or a fragment obtained during such a sequential coupling can be further coupled with a peptide derivative of appropriate length. Alternatively, a compound of formula XVIII can be coupled with an appropriate tetrapeptide.

The aforementioned coupling reactions can be carried out in a manner known per se in peptide chemistry, conveniently using the respective amino acid or peptide derivative protected at the amino group by Fmoc [(9-fluorenyl) methoxycarbonyl] in the presence of EDAC, HOBT and NEM in an organic solvent, e.g. a halogenated hydrocarbon such as dichloromethane.

Finally, after completion of the respective coupling, the resulting ester of the general formula

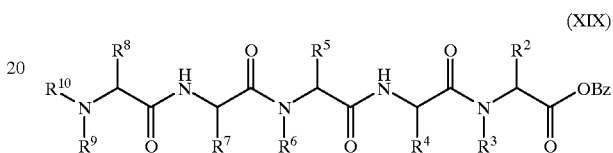

(XIX)

wherein Bz and $R^2$, $R^3$, $R^4$, $R^5$, $R^6$, $R^7$, $R^8$, $R^9$ and $R^{10}$
have the significance given earlier, provided that any carboxy, hydroxy and/or amino-carbonyl group(s) present is/are in protected form, is debenzylated in a known manner by hydrogenolysis, e.g. in the presence of a palladium/carbon catalyst, to give an acid of formula III.

The α-hydroxyamides of formula IV used as starting materials in embodiment b) of the process provided by the invention are novel and also form an object of the present invention. They can be prepared, for example, as illustrated in Scheme 3 hereinafter in which Boc, $R^1$, $R^2$, $R^3$, $R^4$, $R^5$, $R^6$, $R^7$, $R^8$, $R^9$, $R^{10}$, $R^{11}$ and $R^{12}$ have the significance given earlier, provided that any hydroxy group(s) present is/are in protected form.

Scheme 3

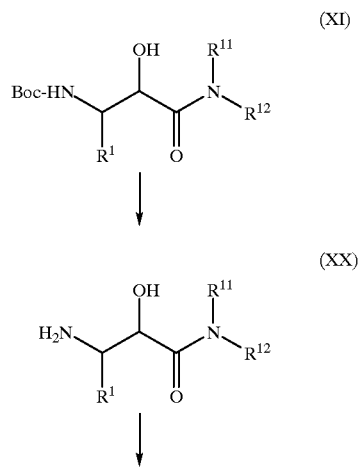

-continued

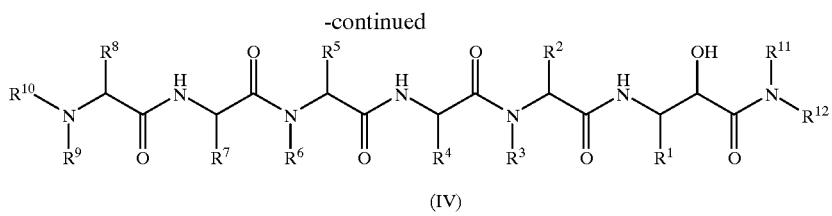

(IV)

Having regard to Scheme 3, in the first step a compound of formula XI, prepared as described in Scheme 1, is treated with an acid, preferably p-toluenesulphonic acid, to give an acid addition salt of an amine of formula XX. This treatment is carried out in a manner analogous to that described earlier in connection with the conversion of an α-ketoamide of formula XII into an acid addition salt of an amine of formula II. Subsequently, an acid addition salt of an amine of formula XX is converted into an α-hydroxyamide starting material of formula IV by condensation with an acid of formula III. The condensation is carried out in an analogous manner to that described earlier in connection with the condensation of an acid addition salt of an amine of formula II with an acid of formula III.

Alternatively, α-hydroxyamide starting materials of formula IV in which $R^{11}$ represents hydrogen and $R^{12}$ represents lower alkyl, aryl, heteroaryl, aryl-lower alkyl, diaryl-lower alkyl, lower cycloalkyl-lower alkyl, lower alkylaminocarbonyl-lower alkyl or lower alkylthio-lower alkyl and $R^2$, $R^4$, $R^5$, $R^7$ and $R^8$ represent other than protected hydroxy-lower alkyl can be prepared by firstly reacting an aldehyde of the general formula

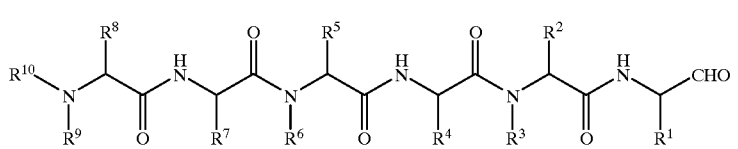

(XXI)

wherein $R^1$, $R^2$, $R^3$, $R^4$, $R^5$, $R^6$, $R^7$, $R^8$, $R^9$ and $R^{10}$ have the significance given in formula IV, with an isocyanide of the general formula $$R^{12a}NC \quad (XXII)$$

wherein $R^{12a}$ represents lower alkyl, aryl, heteroaryl, aryl-lower alkyl, diaryl-lower alkyl, lower cycloalkyl-lower alkyl, lower alkylaminocarbonyl-lower alkyl or lower alkylthio-lower alkyl, in the presence of excess formic acid. When the aryl moiety of the aryl-lower alkyl isocyanide is substituted by a reactive group, e.g. hydroxy or hydroxymethyl, this is protected in a conventional manner. The reaction is suitably effected in an inert organic solvent, e.g. a chlorinated aliphatic hydrocarbon such as dichloromethane, at about room temperature and yields a mixture of an α-hydroxyamide of formula IV and a corresponding formyloxy compound of the general formula

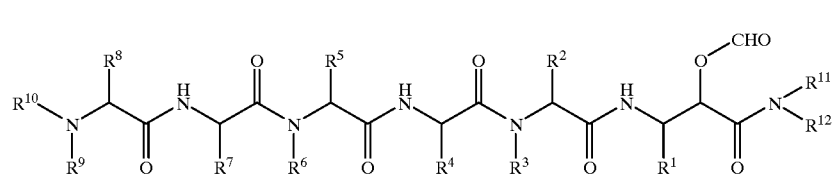

(XXIII)

wherein $R^1$, $R^2$, $R^3$, $R^4$, $R^5$, $R^6$, $R^7$, $R^8$, $R^9$, $R^{10}$, $R^{11}$ and $R^{12}$ have the significance given in formula IV.

On treatment of this mixture of α-hydroxyamide and formyloxy compound with aqueous ammonia at room temperature, the formyloxy compound is converted into the corresponding α-hydroxyamide of formula IV.

The aldehydes of formula XXI can, in turn, be prepared by firstly from a hydroxamate of the general formula

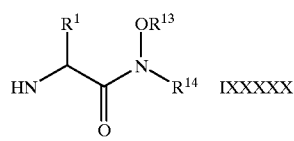

(XXIV)

IXXXXX wherein $R^1$ has the significance given earlier, Q represents an amino protecting group and $R^{13}$ and $R^{14}$ each represent lower alkyl, especially methyl, by reduction with an alkali metal aluminum hydride, conversion of the resulting aldehyde into an acetal of the general formula (XXV)

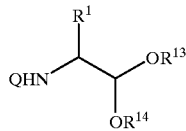

wherein $R^1$, $R^{13}$ and $R^{14}$ and Q have the significance given earlier,
condensation of this acetal (after removal of the amino protecting group) with an acid of formula III hereinbefore and deacetalization of the resulting acetal of the general formula (XXVI)

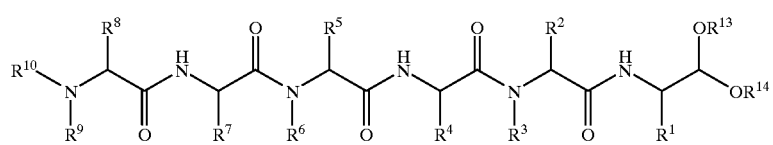

wherein $R^1$, $R^2$, $R^3$, $R^4$, $R^5$, $R^6$, $R^7$, $R^8$, $R^9$, $R^{10}$, $R^{11}$ and $R^{12}$ have the significance given in formula IV.

The reduction of a hydroxamate of formula XXIV is conveniently carried out using lithium aluminum hydride.

The conversion of a resulting aldehyde into an acetal of formula XXV can be carried out in a known manner, e.g. by treatment with trimethyl orthoformate in the presence of an acid such as p-toluenesulphonic acid, The condensation of an acetal of formula XXV with an acid of formula III can be carried out in a manner known per se in peptide chemistry, conveniently in the presence of EDAC, HOBT and NEM and in an inert organic solvent, e.g. a halogenated hydrocarbon such as dichloromethane.

The deacetalization of an acetal of formula XXVI is carried out in a manner known per se, conveniently using trifluoroacetic acid or an equivalent strong acid in the presence of an inert organic solvent such as a halogenated aliphatic hydrocarbon, e.g. dichloromethane, and in the presence of water. Suitably, the deacetalization is carried out at about room temperature. Any hydrolysis-sensitive protecting group is cleaved off under the conditions used for the deacetalization.

The hydroxamates of formula XXIV, insofar as they are not known compounds or analogues of known compounds can be prepared in a similar manner to the known representatives or as described in the Examples hereinafter or in analogy thereto.

The resin-bonded α-hydroxyamides of formula IVA can be prepared, for example, by removing the Fmoc group from a swollen conjugate resin of the formula R-Fmoc, wherein R and Fmoc have the significance given earlier, e.g. using dimethylformamide/piperidine, and reacting the deprotected conjugate resin firstly with a hydroxyacid of the general formula (XXVII)

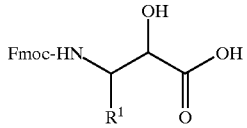

wherein $R^1$ and Fmoc have the significance given earlier, and then with acetic acid. Both reactions are conveniently performed in an inert organic solvent, e.g. dimethylformamide, in the presence of 2-(1H-benzotriazol-1-yl)-1,1,3,3-tetramethyluronium tetrafluoroborate (TBTU) and N-methylmorpholine at about room temperature. This gives a resin conjugate of the formula (XXVIII)

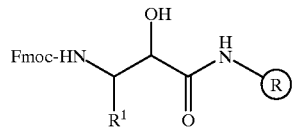

wherein R, $R^1$ and Fmoc have the significance given earlier, which, after deprotection, is subsequently condensed in sequence with respective N-protected amino acids to give the desired resin-bonded α-hydroxyamide of formula IVA.

The hydroxy-acids of formula XXVII can be prepared in an analogous manner to the compounds of formula XA in Scheme 2 hereinbefore.

Compounds also included within the scope of this invention include compounds of formula (XXIX):

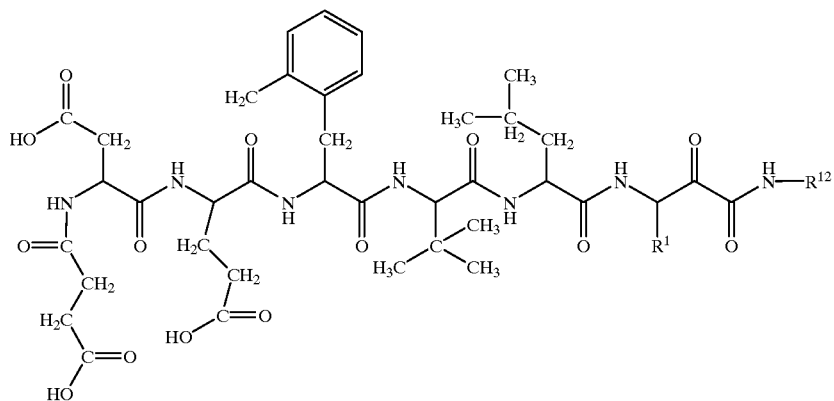

(XXIX)

wherein $R^1$ is selected from the group consisting of lower alkyl and halo-lower alkyl and $R^{12}$ is selected from the group consisting of hydrogen, lower alkyl, aryl-lower alkyl, diaryl-lower alkyl, lower cycloalkyl-lower alkyl, lower alkylaminocarbonyl-lower alkyl, lower alkylthio-lower alkyl, aryl-lower alkyl-lower alkoxy, aryl-lower alkyl-nitro, aryl-lower alkyl-hydroxy-lower alkyl, aryl-hydroxy-lower alkyl, heteroaryl, which contains less than three heteroatoms,-lower alkyl;

Formula (XXX):

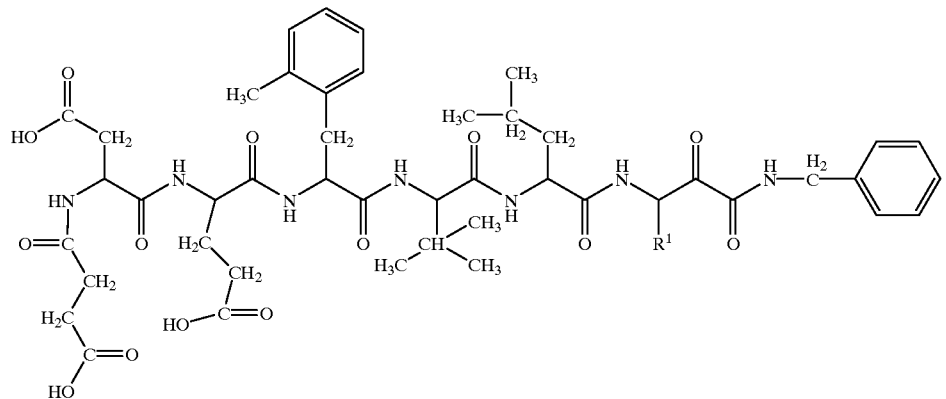

(XXX)

wherein $R^1$ is selected from the group consisting of lower alkenyl, cyano-lower alkyl, lower alkynyl, aryl-lower alkyl, lower alkylthio-lower alkyl, aryl-lower alkylthio-lower alkyl, heteroaryl, which contains less than three heteroatoms,-lower alkyl;

Formula (XXXI):

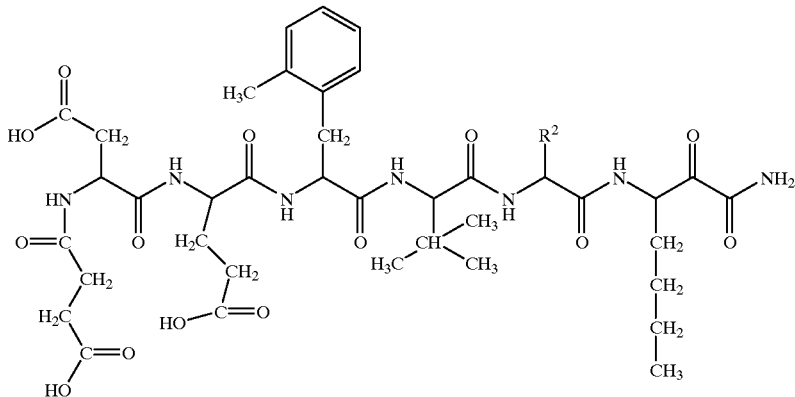

(XXXI)

wherein $R^2$ is selected from the group consisting of lower alkyl, hydroxy-lower alkyl, aminocarbonyl-lower alkyl, dihalo-oxoaryl-lower alkyl-aryl-lower alkyl, heteroaryl, which contains less than three heteroatoms-lower alkyl, lower cycloalkyl-lower alkyl;

Formula (XXXII):

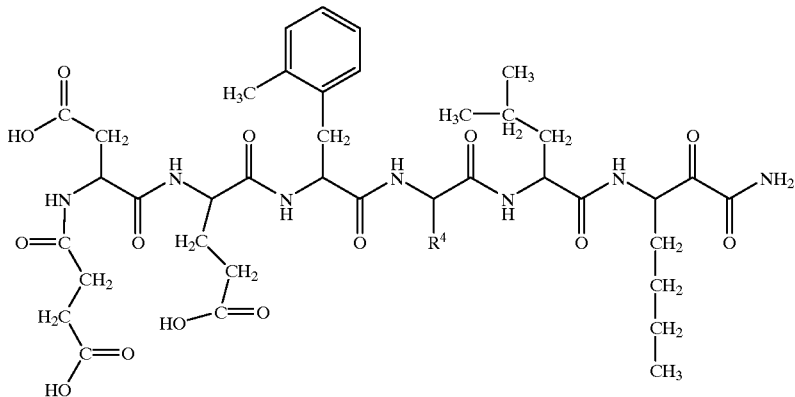

(XXXII)

wherein $R^4$ is selected from the group consisting of lower cycloalkyl, aryl-lower alkoxycarbonyl-lower alkyl, carboxy-lower alkyl, aryl-lower alkyl, lower cycloalkyl-lower alkyl, aryl-lower alkoxy-aryl-lower alkyl, aryl, aryl-lower alkoxy-lower alkyl, lower alkylcarbonylamino-lower alkyl, lower alkyl-thio-lower alkyl, lower alkenyl, and $(CH_2)_2$—NH—C(NH)—NH—(p-tolyl);

Formula (XXXIII):

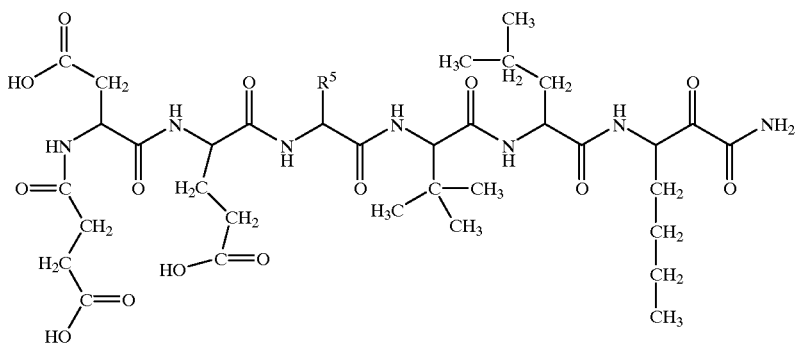

(XXXIII)

wherein R⁵ is selected from the group consisting of lower alkyl, hydroxy-lower alkyl, aryl-lower alkyl-thio-lower alkyl, lower cycloalkyl, lower cycloalkyl-lower alkyl, aryl-lower alkoxycarbonyl-lower alkyl, aryl-lower alkoxy-aryl-lower alkyl, aryl, (CH₂)₃—NH—C(NH)—NH—(p-tosyl), aryl-lower alkoxy-lower alkyl, and heteroaryl, which contains less thee heteroatoms,-lower alkyl; heteroaryl, which contains less that three heteroatoms-lower alkyl, lower alkylcarbonylamino-lower alkyl, aryl-lower alkyl-heteroaryl, which contains less than three heteroatoms,-lower alkyl, lower alkyl-thio-lower alkyl, heteroaryl, which contains less than three heteroatoms,-lower alkyl, lower alkenyloxycarbonyl-lower alkyl, lower Formula (XXXIV):

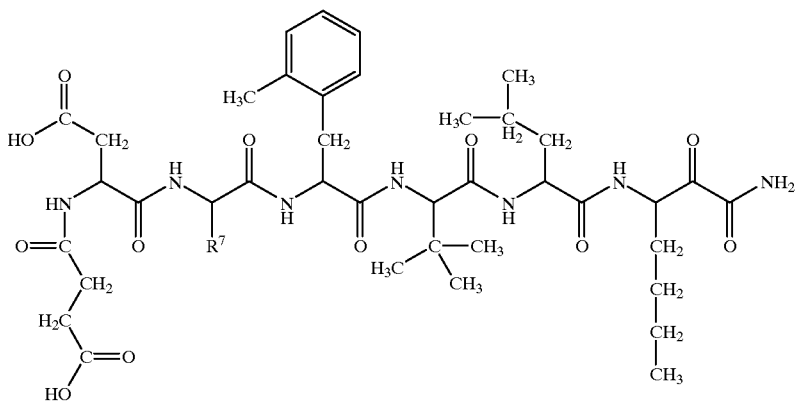

(XXXIV)

wherein R⁷ is selected from the group consisting of aryl-lower alkoxycarbonyl-lower alkyl, aryl-lower alkoxy-aryl-lower alkyl, nitroguanidino-lower alkyl, aryl-lower alkoxy-cycloalkyl, aryl, formidamino-lower alkyl, aryl-nitro-lower alkyl, aryl-lower alkoxy-lower alkyl, lower alkyl, hydrogen, and carboxy-lower alkyl.

Formula (XXXV): (XXXV)

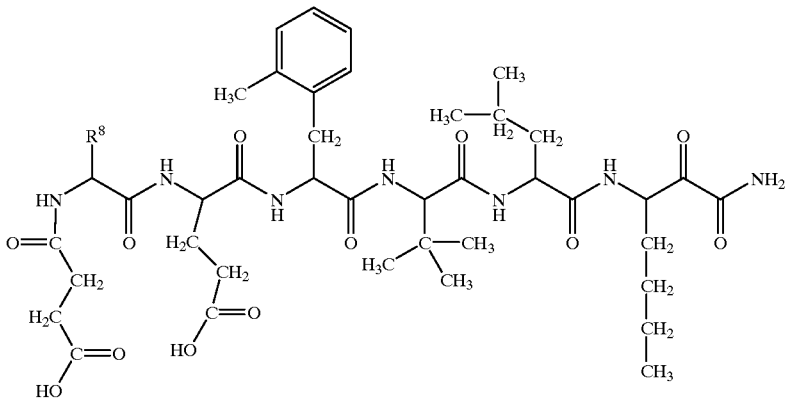

wherein R⁸ is selected from the group consisting of lower cycloalkyl-lower alkyl, lower cycloalkyl, hydroxy-lower alkyl, aryl-lower alkoxy-aryl-lower alkyl, nitroguanidino-lower alkyl, aryl, amino-lower alkyl, arylsulfonylguanidino-lower alkyl, carboxy-lower alkyl, aryl-lower alkoxy-lower alkyl-heteroaryl, which contains less than three heteroatoms-lower alkyl, heteroaryl-lower alkyl, lower alkylsulfinyl-lower alkyl, lower alkylaminocarbonyl-lower alkyl, lower alkylsuphonyl-lower alkyl, aryl-lower alkyl, formamido-lower alkyl, lower alkyl, and aminocarbonyl-lower alkyl; and lower alkoxy-lower alkoxy-lower alkylcarbonyl, di(lower alkoxy)phosphinyl-lower alkylcarbonyl, bicycloloweralkylcarbonyl, heteroaryl, which contains less that three heteroatoms,-lower alkylcarbonyl, lower alkynylcarbonyl, (di(halo-lower alkyl-lower cycloalkyl) carbonyl, lower alkylthio-lower alkylcarbonyl, arylcarbonyl-amino-lower alkylcarbonyl, lower alkylcarbonylamino-lower alkylcarbonyl, arylaminocarbonyl-lower alkylcarbonyl, heteroarylthio-lower alkylcarbonyl, lower cycloalkylcarbonyl, lower cycloalkyl-arylcarbonyl, nitroaryl-lower alkylcarbonyl, lower alkylcarbonyl, and aryl-lower alkoxy carbonyl.

Formula (XXXVI): (XXXVI)

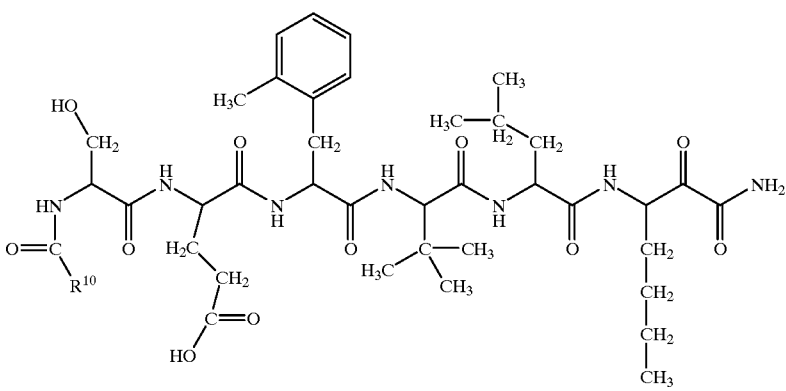

wherein R¹⁰ is selected from the group consisting of lower alkylamino-lower alkylcarbonyl, lower alkylcarbonyl-lower alkylcarbonyl, heteroaryl, which contains less than three heteroatoms, carbonyl, hydroxyfluorenylcarbonyl, heterocycylcarbonyl, aryl-di(lower alkyl)aminocarbonyl, lower cycloalkyl-lower alkoxycarbonyl, aryl-lower alkoxycarbonylamino-lower alkylcarbonyl, lower alkoxy-lower alkylcarbonyl, lower alkylcarbonylamino-lower alkenylcarbonyl, aryl-lower alkenylcarbonyl, lower alkoxycarbonyl-lower alkylcarbonyl, heteroaryl, which contains less than three heteroatoms, carbonyl-lower alkylcarbonyl, hydroxy-halo-lower alkylcarbonyl, di(lower alkyl)aminocarbonyl-lower alkylcarbonyl, lower alkylcarbonyl, lower cycloalkyl-lower alkylcarbonyl, lower alkenylcarbonyl, arylcarbonyl-lower alkylcarbonyl, aryl-lower alkylcarbonyl-lower alkylcarbonyl, lower alkoxy- As mentioned earlier, the compounds of formula I and their salts are inhibitors of proteases of viral origin. For example, all compounds of formula 1 are inhibitors against HCV protease. This activity can be demonstrated using an assay that is described in detail in WO 98/22496, published May 28, 1998.

The following $IC_{50}$ values have been determined:

TABLE

| Compound of formula I | HCV proteinase $IC_{50}$ ($\mu$mol/l) |
|---|---|
| A | 0.004 |
| B | 0.007 |
| C | 0.007 |

TABLE-continued

| Compound of formula I | HCV proteinase IC$_{50}$ ($\mu$mol/l) |
| --- | --- |
| D | 0.007 |
| E | 0.004 |
| F | 0.006 |
| G | 0.004 |
| H | 0.004 |
| I | 0.008 |
| J | 0.0115 |

Compounds:
A=3(RS)-[[N-[N-[N-[N-[N-(3-Carboxypropionyl)-L-α-aspartyl]-L-α-glutamyl]-2-methyl-L-phenylalanyl]-3-methyl-L-valyl]-L-leucyl]amino]-5,5,5-trifluoro-N-[1(S)-2-naphthyl)ethyl]-2-oxovaleramide.
B=3(RS)-[[N-[N-[N-[N-[N-(3-Carboxypropionyl)-L-α-aspartyl]-L-α-glutamyl]-2-methyl-L-phenylalanyl]-3-methyl-L-valyl]-L-leucyl]amino]-5,5,5-trifluoro-2-oxo-N-(1(S)-phenylpropyl)valeramide.
C=3(RS)-[[N-[N-[N-[N-[N-(3-Carboxypropionyl)-L-α-aspartyl]-L-α-glutamyl]-2-methyl-L-phenylalanyl]-3-methyl-L-valyl]-L-leucyl]amino]-5,5,5-trifluoro-N-(2-methyl-1(S)-phenylpropyl)-2-oxovaleramide.
D=3(R or S)-[[N-[N-[N-[N-[N-(3-Carboxypropionyl)-L-α-aspartyl]-L-α-glutamyl]-2-methyl-L-phenylalanyl]-3-methyl-L-valyl]-L-leucyl]amino]-5,5,5-trifluoro-2-oxovaleramide.
E=3(RS)-[[N-[N-[N-[N-[N-(3-Carboxypropionyl)-L-α-aspartyl]-L-α-glutamyl]-2-methyl-L-phenylalanyl]-3-methyl-L-valyl]-L-leucyl]amino]-5,5,5-trifluoro-N-(4-hydroxybenzyl)-2-oxovaleramide.
F=3(RS)-[[N-[N-[N-[N-[N-(3-Carboxypropionyl)-L-α-aspartyl]-L-α-glutamyl]-2-methyl-L-phenylalanyl]-3-methyl-L-valyl]-L-leucyl]amino]-5,5,5-trifluoro-N-(3-methoxybenzyl)-2-oxovaleramide.
G=3(RS)-[[N-[N-[N-[N-[N-(3-Carboxypropionyl)-L-α-aspartyl]-L-α-glutamyl]-2-methyl-L-phenylalanyl]-3-methyl-L-valyl]-L-leucyl]amino]-5,5,5-trifluoro-N-(α(S)-methylbenzyl)-2-oxovaleramide.
H=N-Benzyl-3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-2-oxovaleramide.
I=3(RS)-[[N-[N-[N-[N-[N-(3-Carboxypropionyl)-L-α-aspartyl]-L-α-glutamyl]- 2-methyl-L-phenylalanyl]-3-methyl-L-valyl]-L-leucyl]amino]-5,5,5-trifluoro-N-[1(S)-2-naphthyl)ethyl]-2-oxovaleramide.
J=3(S)-[[N-[N-[N-[N-[N-(3-Carboxypropionyl)-L-α-aspartyl]-L-α-glutamyl]-2-methyl-L-phenylalanyl]-3-methyl-L-valyl]-L-leucyl]amino]-2-oxoheptanamide.

The compounds of formula I and their salts can be used as medicaments, e.g. in the form of pharmaceutical preparations. The pharmaceutical preparations can be administered eternally such as orally in the form of tablets, coated tablets, dragees, hard and soft gelatin capsules, solutions, emulsions or suspensions, nasally, e.g. in the form of nasal sprays, or rectally, e.g. in the form of suppositories. They may, however, also be administered parenterally, e.g. in the form of injection solutions.

The compounds of formula I and their salts can be processed with pharmaceutically inert, organic or inorganic carriers for the production of pharmaceutical preparations. Lactose, corn starch or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like; depending on the nature of the active ingredient no carriers are, however, usually required in the case of soft gelatin capsules. Suitable carriers for the production of solutions and syrups are, for example, water, polyols, sucrose, invert sugar, glucose and the like. Suitable carriers for suppositories are, for example, natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a salt thereof in association with a compatible pharmaceutical carrier are also an object of the present invention, as is a process for the production of such medicaments which comprises bringing one or more of these compounds or salts and, if desired, one or more other therapeutically valuable substances into a galenical administration form together with a compatible pharmaceutical carrier.

As mentioned earlier, the compounds of formula I and their salts can be used in accordance with the invention as therapeutically active substances, especially as antiviral agents. The dosage can vary within wide limits and will, of course, be fitted to the individual requirements in each particular case. In general, in the case of administration to adults a convenient daily dosage should be about 3 mg to about 3 g, preferably about 10 mg to 1 g. The daily dosage may be administered as a single dose or in divided doses and, in addition, the upper dosage limit referred to earlier may be exceeded when this is found to be indicated.

Finally, the use of compounds of formula I and their salts for the production of medicaments, especially of antiviral medicaments, is also an object of the invention.

The following Examples illustrate the present invention:

EXAMPLE 1 i) 194 mg (0.5 mmol) of 3(RS)-(tert-butoxyformamido)-5,5,5-trifluoro-2',4'-dimethyl-2-oxovaleranilide and 285 mg (1.5 mmol) of p-toluenesulphonic acid monohydrate were dissolved in 5 ml of acetonitrile by heating to reflux for 15 seconds. The solution was allowed to cool and was stirred at room temperature for 1 hour. 20 ml of diethyl ether were added to the resulting suspension and the crude 3(RS)-amino-5,5,5-trifluoro-2',4'-dimethyl-2-oxovaleranilide p-toluenesulphonate (1:1) which formed as a white solid was filtered off.

115 mg (0.25 mmol) of the foregoing 3(RS)-amino-5,5,5-trifluoro-2',4'-dimethyl-2-oxovaleranilide p-toluenesulphonate (1:1), 183 mg (0.2 mmol) of N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucine, 58 mg (0.3 mmol) of 1-(3-dimethylamino-propyl)-3-ethylcarbodiimide, 30 mg (0.22 mmol) of 1-hydroxybenzotriazole and 46 mg (0.4 mmol) of N-ethylmorpholine were dissolved in 10 ml of dichloromethane and the solution was stirred at room temperature for 6 hours. The solution was then washed with 2M hydrochloric acid and saturated sodium hydrogen carbonate solution, dried over anhydrous magnesium sulphate, filtered and evaporated. The residue was chromatographed on silica gel using 3.5% methanol in dichloromethane for the elution. The solid obtained was triturated with diethyl ether and filtered off to give 61 mg of 3(RS)-[[N-[N-[N-[N-[N-[3-

(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-2',4'-dimethyl-2-oxovaleranilide as a white solid, MS: m/e 1188.4 [M+H]$^+$.

ii) 50 mg (0.042 mmol) of 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-2',4'-dimethyl-2-oxovaleranilide were dissolved in 3 ml of trifluoroacetic acid and the solution was stirred at room temperature for 30 minutes. The solution was then diluted with 10 ml of toluene and the solvent was removed by evaporation. The solid was triturated with diethyl ether to give 29 mg of 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-2',4'-dimethyl-2-oxovaleranilide as a white solid, MS: m/e 1020.4 [M+H]$^+$.

The 3(RS)-(tert-butoxyformamido)-5,5,5-trifluoro-2',4'-dimethyl-2-oxovaleranilide used as the starting material was prepared as follows:

a) 1.86 g (6.2 mmol) of N,O-dimethyl 2(RS)-(tert-butoxyformamido)-4,4,4-trifluorobutyrohydroxamate were dissolved in 30 ml of anhydrous tetrahydrofuran and the solution was cooled to 0° C. 5 ml (5 mmol) of a 1M solution of lithium aluminum hydride in tetrahydrofuran were added dropwise under a nitrogen atmosphere while maintaining the temperature at 0° C. The mixture was stirred for 30 minutes at 0° C. and the reaction was then quenched by the dropwise addition of saturated potassium hydrogen sulphate solution. The tetrahydrofuran was removed by evaporation and 40 ml of diethyl ether were added. The resulting mixture was stirred vigorously for 20 minutes and the ethereal layer was separated, dried over anhydrous magnesium sulphate, filtered and evaporated. The residue was dissolved in 15 ml of dichloromethane and 1.58 g (18.6 mmol) of acetone cyanohydrin and 376 mg (3.72 mmol) of triethylamine were added. The solution was stirred at room temperature for 1.5 hours, then diluted with 50 ml of diethyl ether and washed five times with water. The organic phase was dried over anhydrous magnesium sulphate, filtered and evaporated, and the residue was chromatographed on silica gel using 35% ethyl acetate in petroleum ether for the elution. The resulting oil was refluxed in 40 ml of 5M hydrochloric acid for 17 hours before being evaporated to dryness. The residue was dissolved in 20 ml of dioxan and 20 ml of water, 5 g (59.8 mmol) of sodium hydrogen carbonate and 3 g (13.76 mmol) of di-tert-butyl dicarbonate were added and the mixture was stirred vigorously for 3 days. The solvent was removed by evaporation and the residue was dissolved in 50 ml of diethyl ether and 50 ml of water. The aqueous solution was separated, acidified with 2M hydrochloric acid and then extracted twice with diethyl ether. The combined ethereal extracts were dried over anhydrous magnesium sulphate, filtered and evaporated. The residue was triturated with 33% diethyl ether in petroleum ether to give 1.01 g of 3(RS)-(tert-butoxyformamido)-5,5,5-trifluoro-2(RS)-hydroxyvaleric acid as a white solid, MS: m/e 288 [M+H]$^+$.

b) A mixture of 287 mg (1 mmol) of 3(RS)-(tert-butoxyformamido)-5,5,5-trifluoro-2(RS)-hydroxyvaleric acid, 363 mg (3 mmol) of 2,4-dimethylaniline, 288 mg (1.5 mmol) of 1-(3-dimethylaminopropyl)-3-ethylcarbodiimide hydrochloride and 150 mg (1.1 mmol) of 1-hydroxybenzotriazole in 10 ml of dichloromethane was stirred at room temperature for 2 hours. The solution was diluted with diethyl ether, washed with 2M hydrochloric acid and saturated sodium bicarbonate solution and then dried over anhydrous magnesium sulphate, filtered and evaporated to give 363 mg of 3(RS)-(tert-butoxyformamido)-5,5,5-trifluoro-2(RS)-hydroxy-2',4' dimethylvaleranilide as a white solid, $^1$H NMR (250 MHz, CDC$_3$) δ: 1.4 (s,4H), 1.45 (s,5H), 2.1 (s,1.5H), 2.15 (s, 1.5H), 2.3 (s,3H), 2.2–2.6 (m,1H), 2.7–3(m,1H), 4.2–4.6 (m,2H), 5.3 (d,0.5H), 5.6 (d,0.5H), 5.9 (d,0.5H), 6.2 (d,0.5H), 7.0 (m,2H), 7.6 (d,0.5H), 7.7 (d,0.5H), 8.6 (s,1H).

c) A mixture of 360 mg (0.92 mmol) of 3(RS)-(tert-butoxyformamido)-5,5,5-trifluoro-2(RS)-hydroxy-2',4'-dimethylvaleranilide and 424 mg (1 mmol) of 1,1,1-triacetoxy-1,1-dihydro-1,2-benziodoxol-3(1H)-one in 10 ml of dichloromethane was stirred under a nitrogen atmosphere for 1 hour. The solution was extracted with a solution of 2.5 g of sodium thiosulphate in 10 ml of saturated sodium bicarbonate solution, then dried over anhydrous magnesium sulphate, filtered and evaporated to dryness. The residue was chromatographed on silica gel using 25% ethyl acetate in petroleum ether for the elution. The solid obtained was triturated with petroleum ether to give 222 mg of 3(RS)-(tert-butoxyformamido)-5,5,5-trifluoro-2',4'-dimethyl-2-oxovaleranilide as a white solid, $^1$H NMR (250 MHz, CDCl$_3$) δ:1.4 (s,9H), 2.25 (s,3H), 2.3 (s,3H), 2.8–3.1 (m,2H), 5.2–5.3 (m,1H), 5.4–5.5 (d,1H), 7.0–7.1 (m,2H), 7.7–7.8 (d,1H), 8.4–8.5 (br.s,1H).

The N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucine used in the second paragraph of part i) of this Example was prepared as follows:

a) A solution of 25 g (63.6 mmol) of L-leucine benzyl ester p-toluenesulphonic acid salt, 14.69 g (63.6 mmol) of N-(tert-butoxycarbonyl)-3-methyl-L-valine, 9.73 g (63.6 mmol) of 1-hydroxybenzotriazole, 7.32 g (63.3 mmol) of N-ethylmorpholine and 12.21 g (63.6 mmol) of 1-(3-dimethylaminopropyl)-3-ethylcarbodiimide hydrochloride in 500 ml of dichloromethane was stirred at room temperature overnight. The solution was washed with water, sodium hydrogen carbonate solution, 2M hydrochloric acid and saturated sodium chloride solution and dried over anhydrous magnesium sulphate. Evaporation gave 21.65 g of N-[(N-tert-butoxycarbonyl)-3-methyl-L-valyl]-L-leucine benzyl ester as an oil which was used in the next step without further purification, MS:m/e 435 [M+H]+.

b) A solution of 9.74 g. (22.4 mmol) of N-[(N-tert-butoxycarbonyl)-3-methyl-L-valyl]-L-leucine benzyl ester in 25 ml of trifluoroacetic acid and 50 ml of dichloromethane was stirred at room temperature for 30 minutes. The solvent was removed by evaporation and 50 ml of toluene were added. Evaporation gave N-(3-methyl-L-valyl)-L-leucine benzyl ester as an oil, which was used in the next step without further purification.

c) A solution of the foregoing oil, 9 g (22.4 mmol) of N-(9-fluorenylmethoxycarbonyl)-2-methyl-L-phenylalanine, 3.43 g (22.4 mmol) of 1-hydroxybenzotriazole, 3.87 g (33.66 mmol) of N-ethylmorpholine and 4.31 g (22.4 mmol) of 1-(3-dimethylaminopropyl)-3-ethylcarbodiimide hydrochloride in 100 ml of dichloromethane was stirred at room temperature overnight. The solution was washed with water, sodium hydrogen carbonate solution, 2M hydrochloric acid and saturated sodium chloride solution and dried over anhydrous magnesium sulphate. Evaporation and chromatography on silica gel using 30% ethyl acetate in petroleum ether (b.p. 40–60° C.) for the elution gave 12.32 g of N-[N-[N-[(9- fluorenyl)methoxycarbonyl]-2-methyl-L-phenylalanyl]-3-methyl-L-valyl]-L-leucine benzyl ester as an oil, MS: m/e 718 [M+H]+.

d) A solution of 10 g (13.95 mmol) of N-[N-[N-[(9-fluorenyl)methoxycarbonyl]-2-methyl-L-phenylalanyl]-3-methyl-L-valyl]-L-leucine benzyl ester in 30 ml of piperidine and 120 ml of dichloromethane was stirred for 30 minutes at room temperature. The solvent was removed by evaporation and the residue was chromatographed on silica gel using firstly 20% ethyl acetate in hexane and then 10% methanol in dichloromethane for the elution. Evaporation gave 6.9 g of N-[N-[2-methyl-L-phenylalanyl]-3-methyl-L-valyl]-L-leucine benzyl ester in the form of an oil which was used in the next step without further purification.

e) A solution of 6.9 g of the foregoing oil, 2.13 g (13.95 mmol) of 1-hydroxybenzotriazole, 2.68 g (13.95 mmol) of 1-(3-dimethylaminopropyl)-3-ethylcarbodiimide hydrochloride and 5.93 g (13.95 mmol) of N-[(9-fluorenyl)methoxycarbonyl]-O-tert-butyl-L-α-glutamic acid in 150 ml of dichloromethane was stirred at room temperature overnight. The solution was washed with water, sodium hydrogen carbonate solution, 2M hydrochloric acid and saturated sodium chloride solution and dried over anhydrous magnesium sulphate. Evaporation and chromatography of the residue on silica gel using 30% ethyl acetate in petroleum ether (b.p. 40–60° C.) for the elution gave 10.89 g of N-[N-[N-[(9-fluorenyl)methoxycarbonyl]-O-tert-butyl-L-α-glutamyl]-2-methyl-L-phenylalanyl]-3-methyl-L-valyl]-L-leucine benzyl ester as a thick oil, MS: m/e 903 [M+H]$^+$.

f) A solution of 10.89 g (12.07 mmol) of N-[N-[N-[N-[(9-fluorenyl)methoxycarbonyl]-O-tert-butyl-L-a-glutamyl]-2-methyl-L-phenylalanyl]-3-methyl-L-valyl]-L-leucine benzyl ester in 30 ml of piperidine and 120 ml of dichloromethane was stirred for 30 minutes at room temperature. The solvent was removed by evaporation and the residue was chromatographed on silica gel using firstly 20% ethyl acetate in hexane and then 10% methanol in dichloromethane for the elution. Evaporation gave N-[N-[N-[O-tert-butyl-L-α-glutamyl]-2-methyl-L-phenylalanyl]-3-methyl-L-valyl]-L-leucine benzyl ester in the form of an oil which was used in the next step without further purification.

g) A solution of the foregoing oil, 4.96 g (12.07 mmol) of N-[(9-fluorenyl)methoxycarbonyl]-O-tert-butyl-L-α-aspartic acid, 1.85 g (12.07 mmol) of 1-hydroxybenzotriazole and 2.32 g (12.07 mmol) of 1-(3-dimethylaminopropyl)-3-ethylcarbodiimide hydrochloride in 100 ml of dichloromethane was stirred at room temperature overnight. The solution was washed with water, sodium hydrogen carbonate solution, 2M-hydrochloric acid and saturated sodium chloride solution and dried over anhydrous magnesium sulphate. Evaporation and chromatography of the residue on silica gel using ethyl acetate for the elution gave 10.088 g of N-[N-[N-[N-[(9-fluorenyl)methoxycarbonyl]-O-tert-butyl-L-α-aspartyl]-O-tert-butyl-L-α-glutamyl]-2-methyl-L-phenylalanyl]-3-methyl-L-valyl]-L-leucine benzyl ester as a white solid. MS: m/e 1074 [M+H]$^+$.

h) A solution of 10.088 g (9.4 mmol) of N-[N-[N-[N-[(9-fluorenyl)methoxycarbonyl]-O-tert-butyl-L-α-aspartyl]-O-tert-butyl-L-α-glutamyl]-2-methyl-L-phenylalanyl]-3-methyl-L-valyl]-L-leucine benzyl ester in 30 ml of piperidine and 120 ml of dichloromethane was stirred for 30 minutes at room temperature. The solvent was removed by evaporation and the residue was chromatographed on silica gel using firstly 20% ethyl acetate in hexane and then 10% methanol in dichloromethane for the elution. Evaporation gave N-[N-[N-[O-tert-butyl-L-α-aspartyl]-O-tert-butyl-L-α-glutamyl-2-methyl-L-phenylalanyl]-3-methyl-L-valyl]-L-leucine benzyl ester in the form of an oil which was used in the next step without further purification.

i) A solution of 8 g of the foregoing oil, 1.64 g (9.4 mmol) of tert-butyl hydrogen succinate, 1.44 g (9.4 mmol) of 1-hydroxybenzotriazole and 1.805 g (9.4 mmol) of 1-(3-dimethylaminopropyl)-3-ethylcarbodiimide hydrochloride in dichloromethane was stirred at room temperature overnight. The solution was washed with water, sodium hydrogen carbonate solution, 2M hydrochloric acid and saturated sodium chloride solution and dried over anhydrous magnesium sulphate. Evaporation and trituration of the residue with acetone gave 6.87 g of N-[N-[N-[N-[3-(tert-butoxycarbonyl)propionyl]-O-tert-butyl-L-αaspartyl]-O-tert-butyl-L-α-glutamyl]-2-methyl-L-phenylalanyl]-3-methyl-L-valyl]-L-leucine benzyl ester as a white solid, MS: m/e 1008.6 [M+H]+, m/e 1030.3 [M+Na]$^+$.

j) A solution of 6.8 g (6.75 mmol) of N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucine benzyl ester in 200 ml of dimethylformamide was hydrogenated over 600 mg of 10% palladium/carbon for 1 hour. The catalyst was removed by filtration and the filtrate was evaporated to give 15 g of crude product which was chromatographed on silica gel using 10–15% methanol in dichloromethane for the elution to give 6 g of N-N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucine as a white solid of melting point 235–236° C.; MS: m/e 918.4 [M+H]+, m/e 940.3 [M+Na]$^+$.

EXAMPLE 2 i) In an analogous manner to that described in Example 1i), but using 3(RS)-(tert-butoxyformamido)-5,5,5-trifluoro-4'-methoxy-2'-methyl-2-oxovaleranilide in place of 3(RS)-(tert-butoxyformamido)-5,5,5-trifluoro-2',4'-dimethyl-2-oxovaleranilide there was obtained 3(RS)-[[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-4'-methoxy-2'-methyl-2-oxovaleranilide, MS: m/e 1204.8 [M+H]$^+$.

ii) In an analogous manner to that described in Example 1ii), from 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-4'-methoxy-2'-methyl-2-oxovaleranilide there was obtained 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-4'-methoxy-2'-methyl-2-oxovaleranilide, MS: m/e 1036.4 [M+H]$^+$.

The 3(RS)-(tert-butoxyformamido)-5,5,5-trifluoro-4'-methoxy-2'-methyl-2-oxovaleranilide used as the starting material was prepared as follows:

a) In an analogous manner to that described in Example 1b), from 3(RS)-(tert-butoxyformamido)-5,5,5-trifluoro-2(RS)-hydroxyvaleric acid and 4-methoxy-2-methylaniline there was obtained 3(RS)-(tert-butoxyformamido)-5,5,5-trifluoro-2(RS)-hydroxy-4'-methoxy-2'-methylvaleranilide, $^1$H NMR (400 MHz, CDCl$_3$) δ: 1.4 (s,4.5H), 1.45 (s,4.5H), 2.2 (s,1.5H), 2.23 (s,1.5H), 2.3–2.55 (m,1H), 2.8–3.0

(m,1H), 3.8 (s,3H), 4.2–4.45 (m,2H), 5.2 (d,0.5H), 5.4 (d,0.5H), 5.9 (d,0.5H), 6.2 (d,0.5H), 6.75 (m,2H), 7.55–7,7 (m,1 H), 8.48 (s,0.5H), 8.52 (s,0.5H).

b) In an analogous manner to that described in Example 1c), from 3(RS)-(tert-butoxyformamido)-5,5,5-trifluoro-2 (RS)-hydroxy-4'-methoxy-2'-methylvaleranilide there was obtained 3(RS)-(tert-butoxyformamido)-5,5,5-trifluoro-4'-methoxy-2'-methyl-2-oxovaleranilide, $^1$H NMR (400 MHz, DMSO) δ: 1.35 (s,9H), 2.1 (s,3H), 2.5–2.7 (m,1H), 2.75–2.9 (m,1 H), 3.7 (s,3H), 5.0 (m,1H), 6.7–6.85 (m,2H), 7.1 (d,1H), 7.7 (d,1H), 10.0 (s,1H).

EXAMPLE 3 i) In an analogous manner to that described in Example 1i), but using 3(RS)-(tert-butoxyformamido)-5,5,5-trifluoro-N-methyl-2-oxovaleramide in place of 3(RS)-(tert-butoxyformamido)-5,5,5-trifluoro-2',4'-dimethyl-2-oxovaleranilide there was obtained 3(RS)-[[N-[N-[N-[N-[N-[3-(tert-butoxycarbonyl)propionyl]-O-tert-butyl-L-α-aspartyl]-O-tert-butyl-L-αglutamyl]-2-methyl-L-phenylalanyl]-3-methyl-L-valyl]-L-leucyl]amino]-5,5,5-trifluoro-N-methyl-2-oxovaleramide, MS: m.e 1098.7 [M+H]$^+$.

ii) In an analogous manner to that described in Example 1ii), from 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-N-methyl-2-oxovaleramide there was obtained 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-N-methyl-2-oxovaleramide, MS: m/e 930.4 [M+H]$^+$.

The 3(RS)-(tert-butoxyformamido)-5,5,5-trifluoro-N-methyl-2-oxovaleramide used as the starting material was prepared as follows:

a) In an analogous manner to that described in Example 1b), from 3(RS)-(tert-butoxyformamido)-5,5,5-trifluoro-2 (RS)-hydroxyvaleric acid and methylamine there was obtained 3(RS)-(tert-butoxyformamido)-5,5,5-trifluoro-2 (RS)-hydroxy-N-methylvaleramide, $^1$H NMR (400 MHz, DMSO) δ: 1.32 (s,4.5H), 1.36 (s,4.5H), 1.95–2.1 (m,0.5H), 2.2–2.5 (m, 1.5H), 2.6 (t,3H), 3.9 (m,1H), 4.05–4.2 (m,1.5H), 5.8 (d,0.5H), 5.95 (d,0.5H), 6.37 (d,0.5H), 6.85 (d,0.5H), 7.75–7.85 (m,1H).

b) In an analogous manner to that described in Example 1c), from 3(RS)-(tert-butoxyformamido)-5,5,5-trifluoro-2 (RS)-hydroxy-N-methylvaleramide there was obtained 3(RS)-(tert-butoxyformamido)-5,5,5-trifluoro-N-methyl-2-oxovaleramide, $^1$H NMR (400 MHz, DMSO) δ: 1.38 (s,9H), 2.65 (d,3H), 2.4–2.9 (m,2H), 4.9–5.0 (m,1H), 7.55 (d,1H), 8.6–8.75 (m,1H).

EXAMPLE 4 i) In an analogous manner to that described in Example 1i), but using 3(RS)-(tert-butoxyformamido)-5,5,5-trifluoro-2-oxo-N-propylvaleramide in place of 3(RS)-(tert-butoxyformamido)-5,5,5-trifluoro-2',4'-dimethyl-2-oxovaleranilide there was obtained 3(RS)-[[N-[N-[N-[N-[N-[3-(tert-butoxycarbonyl)propionyl]-O-tert-butyl-L-α-aspartyl]-O-tert-butyl-L-αglutamyl]-2-methyl-L-phenylalanyl]-3-methyl-L-valyl]-L-leucyl]amino]-5,5,5-trifluoro-2-oxo-N-propylvaleramide, $^1$H NMR (400 MHz, DMSO) δ: 0.8–0.9 (m,18H), 1.38 (s,27H), 1.35–1.9 (m,7H), 2.1 (m,2H), 2.25 (s,3H), 2.3–2.45 (m,4H), 2.5–2.65 (m,3H), 2.7–3.1 (m,5H), 4.2 (m,1H), 4.25 (d,1H), 4.3–4.4 (q,1H), 4.5–4.6 (q,1H), 4.65–4.75 (q,1H), 5.0–5.1 (m,0.5H) 5.15–5.2 (m,0.5H), 7–7.15 (m,4H), 7.7–7.85 (m,2H), 8.0 (t,1H), 8.1 (m,1H), 8.15 (d,1H), 8.6 (d,0.5H), 8.7 (m,1H), 8.8 (d,0.5H).

ii) In an analogous manner to that described in Example 1ii), from 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-2-oxo-N-propylvaleramide there was obtained 3(RS)-[[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-2-oxo-N-propylvaleramide, MS: m.e 958.4 [M+H]$^+$.

The 3(RS)-(tert-butoxyformamido)-5,5,5-trifluoro-2-oxo-N-propylvaleramide used as the starting material was prepared as follows:

a) In an analogous manner to that described in Example 1b), from 3(RS)-(tert-butoxyformamido)-5,5,5-trifluoro-2 (RS)-hydroxyvaleric acid and n-propylamine there was obtained 3(RS)-(tert-butoxyformamido)-5,5,5-trifluoro-2 (RS)-hydroxy-N-propylvaleramide, MS: m/e 329.1 [M+H]$^+$.

b) In an analogous manner to that described in Example 1c), from 3(RS)-(tert-butoxyformamido)-5,5,5-trifluoro-2 (RS)-hydroxy-N-propylvaleramide there was obtained 3(RS)-(tert-butoxyformamido)-5,5,5-trifluoro-2-oxo-N-propylvaleramide, $^1$H NMR (250 MHz, CDCl$_3$) δ: 0.8–0.90 (t,3H), 1.4 (s,9H), 1.45–1.6 (m,2H), 2.7–3.0 (m,2H), 3.15–3.3 (q,2H), 5.1 (m,1H), 5.35 (d,1H), 6.8 (m,1H).

EXAMPLE 5 i) In an analogous manner to that described in Example 1i), but using 3(RS)-(tert-butoxyformamido)-N-butyl-5,5,5-trifluoro-2-oxovaleramide in place of 3(RS)-(tert-butoxyformamido)-5,5,5-trifluoro-2',4'-dimethyl-2-oxovaleranilide there was obtained 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-N-butyl-5,5,5-trifluoro-2-oxovaleramide, $^1$H NMR (400 MHz, DMSO) δ: 0.8–0.9 (m, 18H), 1.18–1.28 (m,2H), 1.38 (s,27H), 1.35–1.8 (m,7H), 2.1 (m,2H), 2.25 (s,3H), 2.3–2.45 (m,4H), 2.45–2.6 (m,3H), 2.7–3.1 (m,5H), 4.2 (m,1H), 4.25 (d,1H), 4.3–4.4 (q 1H), 4.5–4.6 (q,1H), 4.65–4.75 (q,1H), 5.0–5.1 (m,0.25H), 5.1–5.2 (m,0.75H), 7.0–7.15 (m,4H), 7.7 (d,1H), 7.8 (d,1H), 8.0 (d,1H), 8.1 (d,1H), 8.25 (d,1H), 8.55 (d,1H), 8.7 (t,1H).

ii) In an analogous manner to that described in Example 1ii), from 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-N-butyl-5,5,5-trifluoro-2-oxovaleramide there was obtained 3(RS)-[[N-[N-[N-[N-(3-carboxypropionyl)-L-α-aspartyl]-L-α-glutamyl]-2-methyl-L-phenylalanyl]-3-methyl-L-valyl]-L-leucyl]amino]-N-butyl-5,5,5-trifluoro-2-oxovaleramide, MS: m/e 972.3 [M+H]$^+$.

The 3(RS)-(tert-butoxyformamido)-N-butyl-5,5,5-trifluoro-2-oxovaleramide used as the starting material was prepared as follows:

a) In an analogous manner to that described in Example 1b), from 3(RS)-(tert-butoxyformamido)-5,5,5-trifluoro-2 (RS)-hydroxyvaleric acid and n-butylamine there was obtained 3(RS)-(tert-butoxyformamido)-N-butyl-5,5,5- trifluoro-2(RS)-hydroxyvaleramide, ¹H NMR (250 MHz, CDCl₃) δ: 0.9–1.0 (t,3H), 1.3–1.6 (m, 13H), 2.1–2.5 (m,1H), 2.6–2.9 (m,1H), 3.1–3.4 (m,2H), 4.0–4.2 (m,2H), 5.2 (d,0.5H), 5.4–5.5 (m,1H), 5.6 (d,0.5H), 7.8–7.9 (m,1H).

b) In an analogous manner to that described in Example 1c), from 3(RS)-(tert-butoxyformamido)-N-butyl-5,5,5-trifluoro-2(RS)-hydroxyvaleramide there was obtained 3(RS)-(tert-butoxyformamido)-N-butyl-5,5,5-trifluoro-2-oxovaleramide, ¹H NMR (250 MHz, CDCl₃) δ: 0.9–1.0 (t,3H), 1.3–1.6 (m, 13H), 2.7–3.1 (m,2H), 3.3–3.4 (q,2H), 5.1–5.2 (m,1H), 5.3–5.4 (d,1H), 6.8–6.9 (m,1H).

EXAMPLE 6 i) In an analogous manner to that described in Example 1i), but using 3(RS)-(tert-butoxyformamido)-5,5,5-trifluoro-N-hexyl-2-oxovaleramide in place of 3(RS)-(tert-butoxyformamido)-5,5,5-trifluoro-2',4'-dimethyl-2-oxovaleranilide there was obtained 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-N-hexyl-2-oxovaleramide, MS: m/e 1168.7 [M+H]⁺.

ii) In an analogous manner to that described in Example 1ii), from 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-N-hexyl-2-oxovaleramide there was obtained 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-N-hexyl-2-oxovaleramide, MS: m/e 1000.3 [M+H]⁺.

The 3(RS)-(tert-butoxyformamido)-5,5,5-trifluoro-N-hexyl-2-oxovaleramide used as the starting material was prepared as follows:

a) In an analogous manner to that described in Example 1b), from 3(RS)-(tert-butoxyformamido)-5,5,5-trifluoro-2(RS)-hydroxyvaleric acid and n-hexylamine there was obtained 3(RS)-(tert-butoxyformamido)-5,5,5-trifluoro-N-hexyl- 2(RS)-hydroxyvaleramide, ¹H NMR (250 MHz, CDCl₃) δ: 0.8–0.9 (t,3H), 1.2–1.6 (m, 17H), 2.1–2.8 (m,2H), 3.15–3.4 (m,2H), 4.05–4.3 (m,2H), 5.2 (d,0.5H), 5.4–5.5 (m,1H), 5.65 (d,0.5H), 6.8–7.0 (m,1H).

b) In an analogous manner to that described in Example 1c), from 3(RS)-(tert-butoxyformamido)-5,5,5-trifluoro-N-hexyl-2(RS)-hydroxyvaleramide there was obtained 3(RS)-(tert-butoxyformamido)-5,5,5-trifluoro-N-hexyl-2-oxovaleramide, ¹H NMR (250 MHz, CDCl₃) δ: 0.8–0.9 (t,3H), 1.2–1.7 (m, 17H), 2.8–3.1 (m,2H), 3.3 (q,2H), 5.15 (m,1H), 5.4 (d,2H), 6.8–6.9 (m,1H).

EXAMPLE 7 i) In an analogous manner to that described in Example 1i), but using 2-[3(RS)-(tert-butoxyformamido)-5,5,5-trifluoro-2-oxovaleramido]-N-methylacetamide in place of 3(RS)-(tert-butoxyformamido)-5,5,5-trifluoro-2',4'-dimethyl-2-oxovaleranilide there was obtained 2-[3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-2-oxovaleramido]-N-methylacetamide, MS: m/e 1155.6 [M+H]⁺.

ii) In an analogous manner to that described in Example 1ii), from 2-[3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-2-oxovaleramido]-N-methylacetamide there was obtained N2-[3(RS)-[[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-2-oxovaleryl]-N1-methylglycinamide, MS: m/e 987.5 [M+H]⁺.

The 2-[3(RS)-(tert-butoxyformamido)-5,5,5-trifluoro-2-oxovaleramido]-N-methylacetamide used as the starting material was prepared as follows:

a) In an analogous manner to that described in Example 1b), from 3(RS)-(tert-butoxyformamido)-5,5,5-trifluoro-2(RS)-hydroxyvaleric acid and glycine methylamide there was obtained 2-[3(RS)-(tert-butoxyformamido)-5,5,5-trifluoro-2(RS)-hydroxyvaleramido]-N-methylacetamide, ¹H NMR (400 MHz, DMSO) δ: 1.3–1.4 (d,9H), 2.25–2.6 (m,2H), 2.6 (dd,3H), 3.5–3.8 (m,2H), 3.9–4.0 (m,1H), 4.1–4.2 (m,1H), 5.9 (d,0.5H), 6.1 (d,0.5H), 6.5 (d,0.5H), 6.9 (d,0.5H), 7.65–7.75 (m,1H), 8.0–8.1 (m,1H).

b) In an analogous manner to that described in Example 1c), from 2-[3(RS)-(tert-butoxyformamido)-5,5,5-trifluoro-2(RS)-hydroxyvaleramido]-N-methylacetamide there was obtained 2-[3(RS)-(tert-butoxyformamido)-5,5,5-trifluoro-2-oxovaleramido]-N-methylacetamide, ¹H NMR (400 MHz, DMSO) δ: 1.3–1.45 (s,9H), 2.6 (d,3H), 2.4–2.9 (m,2H), 3.6–3.8 (m,2H), 5.0–5.1 (m,1H), 7.5 (d,1H), 7.8 (m,1H), 8.8–8.9 (t,1H).

EXAMPLE 8 i) In an analogous manner to that described in Example 1i), but using 3(RS)-(tert-butoxyformamido)-5,5,5-trifluoro-N-[2-(methylthio)ethyl]-2-oxovaleramide in place of 3(RS)-(tert-butoxyformamido)-5,5,5-trifluoro-2',4'-dimethyl-2-oxovaleranilide there was obtained 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-N-[2-(methylthio)ethyl]-2-oxovaleramide, MS: m/e 1158.7 [M+H]⁺.

ii) In an analogous manner to that described in Example 1ii), from 3(RS)-[[N-[N-[N-[N-[N-[3-(tert-butoxycarbonyl)propionyl]-O-tert-butyl-L-α-aspartyl]-O-tert-butyl-L-α-glutamyl]- 2-methyl-L-phenylalanyl]-3-methyl-L-valyl]-L-leucyl]amino]-5,5,5-trifluoro-N-[2-(methylthio)ethyl]-2-oxovaleramide there was obtained 3(RS)-[[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-N-[2-(methylthio)ethyl]-2-oxovaleramide, MS: m/e 990.3 [M+H]⁺.

The 3(RS)-(tert-butoxyformamido)-5,5,5-trifluoro-N-[2-(methylthio)ethyl]-2-oxovaleramide used as the starting material was prepared as follows:

a) In an analogous manner to that described in Example 1b), from 3(RS)-(tert-butoxyformamido)-5,5,5-trifluoro-2(RS)-hydroxyvaleric acid and 2-(methylthio)ethylamine there was obtained 3(RS)-(tert-butoxyformamido)-5,5,5-trifluoro-2(RS)-hydroxy-N-[2-(methylthio)ethyl] valeramide, ¹H NMR (250 MHz, CDCl₃) δ: 1.4 (d,9H), 2.1 (s,3H), 2.1–2.8 (m,4H), 3.4–3.6 (m,2H), 4.1–4.4 (m,2H), 5.3 (d,0.5H), 5.4–5.7 (m, 1.5H), 7.2–7.4 (m,1H).

b) In an analogous manner to that described in Example 1c), from 3(RS)-tert-butoxyformamido)-5,5,5-trifluoro-2(RS)-hydroxy-N-[2-(methylthio)ethyl]valeramide there was obtained 3(RS)-(tert-butoxyformamido)-5,5,5-trifluoro-N-[2-(methylthio)ethyl]-2-oxovaleramide, ¹H NMR (250

MHz, CDCl₃) δ: 1.4 (s,3H), 2.1 (s,3H), 2.6 (t,2H), 2.7–3.0 (m,2H), 3.5 (q,2H), 5.1 (q,1H), 5.4 (d,1H), 7.2 (m,1H).

EXAMPLE 9 i) In an analogous manner to that described in Example 1i), but using 3(RS)-(tert-butoxyformamido)-5,5,5-trifluoro-N-isopropyl-2-oxovaleramide in place of 3(RS)-(tert-butoxyformamido)-5,5,5-trifluoro-2',4'-oxovaleranilide there was obtained 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-N-isopropyl-5,5,5-trifluoro-2-oxovaleramide, ¹H NMR (400 MHz, DMSO) δ: 0.75–0.95 (m, 15H), 1.0–1.1 (m,6H), 1.5–1.9 (m,4H), 2.05–2.15 (m,2H), 2.25 (s,3H), 2.3–2.4 (m,6H), 2.5–3.0 (m,4H), 3.8–3.9 (m,1H), 4.15–4.4 (m,3H), 4.5–4.6 (q,1H), 4.6–4.7 (q,1H), 5.0 (m,0.5H), 5.2 (m,0.5H), 6.95–7.1 (m,4H), 7.7–7.85 (m,2H), 7.9–8.0 (t,1H), 8.1 (m,1H), 8.2 (d,1H), 8.5–8.6 (t, 1.5H), 8.65 (d,0.5H).

ii) In an analogous manner to that described in Example 1ii), from 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-N-isopropyl-5,5,5-trifluoro-2-oxovaleramide there was obtained 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-N-isopropyl-2-oxovaleramide, MS: m/e 958.4 [M+H]⁺.

The 3(RS)-(tert-butoxyformamido)-5,5,5-trifluoro-N-isopropyl-2-oxovaleramide used as the starting material was prepared as follows:

a) In an analogous manner to that described in Example 1b), from 3(RS)-(tert-butoxyformamido)-5,5,5-trifluoro-2(RS)-hydroxyvaleric acid and isopropylamine there was obtained 3(RS)-(tert-butoxyformamido)-5,5,5-trifluoro-2(RS)-hydroxy-N-isopropylvaleramide, MS: m/e 329.1 [M+H]⁺.

b) In an analogous manner to that described in Example 1c), from 3(RS)-(tert-butoxyformamido)-5,5,5-trifluoro-2(RS)-hydroxy-N-isopropylvaleramide there was obtained 3(RS)-(tert-butoxyformamido)-5,5,5-trifluoro-N-isopropyl-2-oxovaleramide, ¹H NMR (250 MHz, CDCl₃) δ: 1.1 (d,6H), 1.4 (s,9H), 2.7–3.0 (m,2H), 4.0 (m,1H), 5.1 (q, 1H), 5.3–5.4 (d,1H), 6.6 (d,1H).

EXAMPLE 10 i) In an analogous manner to that described in Example 1i), but using 3(RS)-(tert-butoxyformamido)-5,5,5-trifluoro-N-[(diisopropyl)methyl]-2-oxovaleramide in place of 3(RS)-(tert-butoxyformamido)-5,5,5-trifluoro-2',4'-dimethyl-2-oxovaleranilide there was obtained 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-N-[(diisopropyl)methyl]-2-oxovaleramide, MS: m/e 1182.9 [M+H]⁺.

ii) In an analogous manner to that described in Example 1ii), from 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-N-[(diisopropyl)methyl]-2-oxovaleramide there was obtained 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl] amino]-5,5,5-trifluoro-N-(1-isopropyl-2-methylpropyl)-2-oxovaleramide, MS: m/e 1014.5 [M+H]⁺.

The 3(RS)-(tert-butoxyformamido)-5, 5,5-trifluoro-N-[(diisopropyl)methyl]-2-oxovaleramide used as the starting material was prepared as follows:

a) In an analogous manner to that described in Example 1b), from 3(RS)-(tert-butoxyformamido)-5,5,5-trifluoro-2(RS)-hydroxyvaleric acid and 2,4-dimethyl-3-pentylamine there was obtained 3(RS)-(tert-butoxyformamido)-5,5,5-trifluoro-2(RS)-hydroxy-N-(diisopropyl)methyl]valeramide, ¹H NMR (400 MHz, DMSO) δ: 0.7–0.8 (dd, 12H), 1.3–1.4 (d,9H), 1.7–1.8 (m,2H), 2.05–2.5 (m,2H), 3.3–3.4 (m,1H), 3.9–4.0 (m,1H), 4.1–4.2 (m,1H), 5.8 (d,0.5H), 6.0 (d,0.5H), 6.3 (d,0.5H), 6.8 (d,0.5H), 7.1–7.2 (t,1H).

b) In an analogous manner to that described in Example 1c), from 3(RS)-(tert-butoxyformamido)-5,5,5-trifluoro-2(RS)-hydroxy-N-(diisopropyl)methyl]valeramide there was obtained 3(RS)-(tert-butoxyformamido)-5,5,5-trifluoro-N-[(diisopropyl)methyl]-2-oxovaleramide, ¹H NMR (400 MHz, DMSO) δ: 0.7–0.85 (m, 12H), 1.3 (s,9H), 1.8–1.9 (m,2H), 2.5–2.8 (m,2H), 3.3–3.4 (m,1H), 4.9 (m,1H), 7.5–7.6 (d,1H), 8.1–8.2 (d,1H).

EXAMPLE 11 i) In an analogous manner to that described in Example 1i), but using 3(RS)-(tert-butoxyformamido)-5,5,5-trifluoro-2-oxo-N-[(diphenyl)methyl]valeramide in place of 3(RS)-(tert-butoxyformamido)-5,5,5-trifluoro-2',4'-dimethyl-2-oxovaleranilide there was obtained 3(RS)-[[N-[N-[N-[N-[N-[3-(tert-butoxycarbonyl)propionyl]-O-tert-butyl-L-α-aspartyl]-O-tert-butyl-L-αglutamyl]-2-methyl-L-phenylalanyl]-3-methyl-L-valyl]-L-leucyl]amino]-5,5,5-trifluoro-2-oxo-N-(diphenylmethyl)valeramide, MS: m/e 1251.0 [M+H]⁺.

ii) In an analogous manner to that described in Example 1ii), from 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-2-oxo-N-(diphenylmethyl)valeramide there was obtained 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-2-oxo-N-(diphenylmethyl)valeramide, MS: m/e 1082.4 [M+H]⁺.

The 3(RS)-(tert-butoxyformamido)-5,5,5-trifluoro-2-oxo-N-[(diphenyl)methyl]valeramide used as the starting material was prepared as follows:

a) In an analogous manner to that described in Example 1b), from 3(RS)-(tert-butoxyformamido)-5,5,5-trifluoro-2(RS)-hydroxyvaleric acid and diphenylmethylamine there was obtained 3(RS)-(tert-butoxyformamido)-5,5,5-trifluoro-2(RS)-hydroxy-N-[(diphenyl)methyl]valeramide, ¹H NMR (250 MHz, CDCl₃) δ: 1.4 (d,9H), 2.1–2.8 (m,2H), 4.1–4.4 (m,2H), 5.1 (d,0.5H), 5.5 (m,0.5H), 5.9–6.2 (m,1H), 7.1–7.4 (m, 10H), 7.5–7.6 (m,1H).

b) In an analogous manner to that described in Example 1c), from 3(RS)-(tert-butoxyformamido)-5,5,5-trifluoro-2(RS)-hydroxy-N-[(diphenyl)methyl]valeramide there was obtained 3(RS)-(tert-butoxyformamido)-5,5,5-trifluoro-2-oxo-N-[(diphenyl)methyl]valeramide, ¹H NMR (250 MHz, CDCl₃) δ: 1.4 (s,9H), 2.7–3.0 (m,2H), 5.1 (q,1H), 5.4 (d,1H), 6.15 (d,1H), 7.1–7.4 (m, 10H), 7.4–7.5 (d,1H).

EXAMPLE 12 i) In an analogous manner to that described in Example 1i), but using 3(RS)-(tert-butoxyformamido)-N-tert-butyl-5, 5,5-trifluoro-2-oxo-valeramide in place of 3(RS)-(tert-butoxyformamido)-5,5,5-trifluoro-2',4'-dimethyl-2-oxovaleranilide there was obtained 3(RS)-[[N-[N-[N-[N-[N-[3-(tert-butoxycarbonyl)propionyl]-O-tert-butyl-L-α-aspartyl]-O-tert-butyl-L-α-glutamyl]2-methyl-L-phenylalanyl]-3-methyl-L-valyl]-L-leucyl]amino]-N-tert-butyl-5,5,5-trifluoro-2-oxovaleramide, MS: m/e 1140.6 [M+H]$^+$.

ii) In an analogous manner to that described in Example 1ii), from 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-N-tert-butyl-5,5,5-trifluoro-2-oxovaleramide there was obtained N-tert-butyl-3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-2-oxovaleramide, MS: m/e 972.4 [M+H]$^+$.

The 3(RS)-(tert-butoxyformamido)-N-tert-butyl-5,5,5-trifluoro-2-oxovaleramide used as the starting material was prepared as follows:

a) In an analogous manner to that described in Example 1b), from 3(RS)-(tert-butoxyformamido)-5,5,5-trifluoro-2(RS)-hydroxyvaleric acid and tert-butylamine there was obtained 3(RS)-(tert-butoxyformamido)-N-tert-butyl-5,5,5-trifluoro-2(RS)-hydroxyvaleramide, $^1$H NMR (250 MHz, CDCl$_3$) δ: 1.3–1.5 (m, 18H), 2.1–2.8 (m,2H), 3.9–4.2 (m,2H), 5.2 (d,0.5H), 5.35 (d,0.5H), 5.5 (t,1H), 6.7 (s,1H).

b) In an analogous manner to that described in Example 1c), from 3(RS)-(tert-butoxyformamido)-N-tert-butyl-5,5,5-trifluoro-2(RS)-hydroxyvaleramide there was obtained 3(RS)-(tert-butoxyformamido)-N-tert-butyl-5,5,5-trifluoro-2-oxovaleramide, $^1$H NMR (250 MHz, CDCl$_3$) δ: 1.35 (s,9H), 1.4 (s,9H), 2.7–3.0 (m,2H), 5.1 (q,1H), 5.4 (d,1H), 6.7 (s,1H).

EXAMPLE 13 i) In an analogous manner to that described in Example 1i), but using N-benzyl-3(RS)-(tert-butoxyformamido)-5,5,5-trifluoro-2-oxo-valeramide in place of 3(RS)-(tert-butoxyformamido)-5,5,5-trifluoro-2',4'-dimethyl-2-oxovaleranilide there was obtained N-benzyl-3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-2-oxovaleramide, MS: m/e 1174.8 [M+H]$^+$.

ii) In an analogous manner to that described in Example 1ii), from N-benzyl-3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-2-oxovaleramide there was obtained N-benzyl-3(RS)-[[N-[N-[N-[N-[N-( 3-carboxypropionyl)-L-α-aspartyl]-L-α-glutamyl]-2-methyl-L-phenylalanyl]-3-methyl-L-valyl]-L-leucyl]amino]-5,5,5-trifluoro-2-oxovaleramide, MS: m/e 1006.4 [M+H]$^+$.

The N-benzyl-3(RS)-(tert-butoxyformamido)-5,5,5-trifluoro-2-oxo-valeramide used as starting material was prepared as follows:

a) In an analogous manner to that described in Example 1b), from 3(RS)-(tert-butoxyformamido)-5,5,5-trifluoro-2(RS)-hydroxyvaleric acid and benzylamine there was obtained N-benzyl-3(RS)-(tert-butoxyformamido)-5,5,5-trifluoro-2(RS)-hydroxyvaleramide, $^1$H NMR (250 MHz, DMSO) δ: 1.4 (s,9H), 2.3–2.7 (m,2H), 4.0–4.1 (m,1H), 4.2–4.5 (m,3H), 6.0 (d,0.5H), 6.1 (d,0.5H), 6.5 (d,0.5H), 7.0 (d,0.5H), 7.3–7.4 (m,5H), 8.4–8.5 (m,1H).

b) In an analogous manner to that described in Example 1c), from N-benzyl-3(RS)-(tert-butoxyformamido)-5,5,5-trifluoro-2(RS)-hydroxyvaleramide there was obtained N-benzyl-3(RS)-(tert-butoxyformamido)-5,5,5-trifluoro-2-oxovaleramide, $^1$H NMR (250 MHz, CDCl$_3$) δ: 1.4 (s,9H), 2.7–3.0 (m,2H), 4.5 (d,2H), 5.2 (q,1H), 5.4 (d,1H), 7.05–7.15 (m,1H), 7.2–7.4 (m,5H).

EXAMPLE 14 i) In an analogous manner to that described in Example 1i), but using 3(RS)-(tert-butoxyformamido)-N-(1(S)-cyclohexylethyl)-5,5,5-trifluoro-2-oxovaleramide in place of 3(RS)-(tert-butoxyformamido)-5,5,5-trifluoro-2',4'-dimethyl-2-oxovaleranilide there was obtained 3(RS)-[[N-[N-[N-[N-[N-[3-(tert-butoxycarbonyl)propionyl]-O-tert-butyl-L-α-aspartyl]-O-tert-butyl-L-αglutamyl]-2-methyl-L-phenylalanyl]-3-methyl-L-valyl]-L-leucyl]amino]-N-(1(S)-cyclohexylethyl)-5,5,5-trifluoro-2-oxovaleramide, $^1$H NMR (400 MHz, DMSO) δ: 0.75–0.95 (m,15H), 1.0–1.1 (t,3H), 1.1–1.2 (m,4H), 1.4 (s,27H), 1.5–1.9 (m,8H), 2.0–2.2 (m,2H), 2.2 (d,3H), 2.30–2.45 (m,5H), 2.5–3.0 (m,5H), 3.5–3.6 (m,1H), 4.15–4.3 (m,2H), 4.3–4.4 (m,1H), 4.50 (m,1H), 4.6–4.7 (q,1H), 5.0 (m,0.5H), 5.2–5.3 (m,0.5H), 7.0–7.15 (m,4H), 7.7–7.75 (dd,1H), 7.75–7.80 (d,1H), 7.9–8.0 (t,1H), 8.05–8.1 (dd,1H), 8.2 (d,1H), 8.4–8.5 (t, 1.5H), 8.7–8.8 (d,0.5H).

ii) In an analogous manner to that described in Example 1ii), from 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-N-(1(S)-cyclohexylethyl)-5,5,5-trifluoro-2-oxovaleramide there was obtained 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-N-(1(S)-cyclohexylethyl)-5,5,5-trifluoro-2-oxovaleramide, MS: m/e 1026.3 [M+H]$^+$.

The 3(RS)-(tert-butoxyformamido)-N-(1(S)-cyclohexylethyl)-5,5,5-trifluoro-2-oxovaleramide used as the starting material was prepared as follows:

a) In an analogous manner to that described in Example 1b), from 3(RS)-(tert-butoxyformamido)-5,5,5-trifluoro-2(RS)-hydroxyvaleric acid and (S)-1-cyclohexylethylamine there was obtained 3(RS)-(tert-butoxyformamido)-N-(1(S)-cyclohexylethyl)-5,5,5-trifluoro-2(RS)-hydroxyvaleramide, $^1$H NMR (400 MHz, DMSO) δ: 0.8–1.3 (m,9H), 1.3–1.4 (d,9H), 1.55–1.7 (m,5H), 2.0–2.5 (m,2H), 3.55–3.65 (m,1H), 3.8–3.9 (m,1H), 4.05–4.2 (m,1H), 6.3–6.4 (m,0.5H), 6.8–6.9 (m,0.5H), 7.4–7.5 (m,1H).

b) In an analogous manner to that described in Example 1c), from 3(RS)-(tert-butoxyformamido)-N-(1(S)-cyclohexylethyl)-5,5,5-trifluoro-2(RS)-hydroxyvaleramide there was obtained 3(RS)-(tert-butoxyformamido)-N-(1(S)-cyclohexylethyl)-5,5,5-trifluoro-2-oxovaleramide, $^1$H NMR (400 MHz, DMSO) δ: 0.75–1.2 (m,9H), 1.35 (s,9H), 1.5–1.7 (m,5H), 2.45–2.85 (m,2H), 3.55–3.65 (m,1H), 4.85–4.95 (m,1H), 7.5–7.6 (d,1H), 8.4–8.5 (dd,1H).

EXAMPLE 15 i) In an analogous manner to that described in Example 1i), but using 3(RS)-(tert-butoxyformamido)-5,5,5-trifluoro-N-(α(S)-methylbenzyl)-2-oxovaleramide in place of 3(RS)-(tert-butoxyformamido)-5,5,5-trifluoro-2',4'-dimethyl-2-oxovaleranilide there was obtained 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5- trifluoro-N-(α(S)-methylbenzyl)-2-oxovaleramide, $^1$H NMR (400 MHz, DMSO) δ: 0.75–0.9 (m, 15H), 1.35 (s,27H), 1.35–1.8 (m,4H), 2.05–2.15, (m,2H), 2.25 (s,3H), 2.3–2.45 (m,6H), 2.5–3.0 (m,6H), 4.15–4.45 (m,3H), 4.45–4.55 (q 1H), 4.6–4.7 (m,1H) 4.8–5.0 (m,1H), 7.0–7.35 (m,9H), 7.7–7.85 (m,3H), 7.95–8.0 (m 1H), 8.05–8.1 (d,1H), 8.2 (d,1H), 8.7 (d,0.5H), 9.15 (d,0.5H).

ii) In an analogous manner to that described in Example 1ii), from 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-N-(α(S)-methylbenzyl)-2-oxovaleramide there was obtained 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-N-(α(S)-methylbenzyl)-2-oxovaleramide, MS: m/e 1020.5 [M+H]$^+$.

The 3(RS)-(tert-butoxyformamido)-5,5,5-trifluoro-N-(α(S)-methylbenzyl)-2-oxovaleramide used as the starting material was prepared as follows:

a) In an analogous manner to that described in Example 1b), from 3(RS)-(tert-butoxyformamido)-5,5,5-trifluoro-2(RS)-hydroxyvaleric acid and (S)-α-methylbenzylamine there was obtained 3(RS)-(tert-butoxyformamido)-5,5,5-trifluoro-2(RS)-hydroxy-N-(α(S)-methylbenzyl)valeramide, $^1$H NMR (400 MHz, DMSO) δ: 1.3–1.4 (m, 12H), 1.8–1.95 (m,0.5H), 2.1–2.5 (m, 1.5H), 3.85–3.95 (m,1H), 4.05–4.2 (m,1H), 4.85– 4.95 (m,1H), 5.6 (d,0.25H), 6.8 (d,0.25H), 5.95 (t,0.5H), 6.4–6.5 (m,0.5H), 6.8–6.9 (dd, 0.5H), 7.15–7.35 (m,5H), 8.05–8.25 (m,1H).

b) In an analogous manner to that described in Example 1c), from 3(RS)-(tert-butoxyformamido)-5,5,5-trifluoro-2(RS)-hydroxy-N-(α(S)-methylbenzyl)valeramide there was obtained 3(RS)-(tert-butoxyformamido)-5,5,5-trifluoro-N-(α(S)-methylbenzyl)-2-oxovaleramide, $^1$H NMR (400 MHz, DMSO) δ: 1.3–1.45 (m, 12H), 2.45–2.85 (m,2H), 4.8–5.0 (m,2H), 7.2–7.4 (m,5H), 7.55 (d,0.5H), 7.6 (d,0.5H), 9.1–9.2 (t,1H).

EXAMPLE 16 i) In an analogous manner to that described in Example 1i), but using 3(RS)-(tert-butoxyformamido)-5,5,5-trifluoro-2-oxo-N-(α(S)-phenylpropyl)valeramide in place of 3(RS)-(tert-butoxyformamido)-5,5,5-trifluoro-2',4'-dimethyl-2-oxovaleranilide there was obtained 3(RS)-[[N-[N-[N-[N-[N-[3-(tert-butoxycarbonyl)propionyl]-O-tert-butyl-L-α-aspartyl]-O-tert-butyl-L-αglutamyl]-2-methyl-L-phenylalanyl]-3-methyl-L-valyl]-L-leucyl]amino]-5,5,5-trifluoro-2-oxo-N-(1(S)-phenylpropyl)valeramide, MS: m/e 1202.8 [M+H]$^+$.

ii) In an analogous manner to that described in Example 1ii), from 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-2-oxo-N-(1(S)-phenylpropyl)valeramide there was obtained 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-2-oxo-N-(1(S)-phenylpropyl)valeramide, MS: m/e 1034.4 [M+H]$^+$.

The 3(RS)-(tert-butoxyformamido)-5,5,5-trifluoro-2-oxo-N-(1(S)-phenylpropyl)valeramide used as the starting material was prepared as follows:

a) In an analogous manner to that described in Example 1b), from 3(RS)-(tert-butoxyformamido)-5,5,5-trifluoro-2(RS)-hydroxyvaleric acid and (S)-α-ethylbenzylamine there was obtained 3(RS)-(tert-butoxyformamido)-5,5,5-trifluoro-2(RS)-hydroxy-N-(1(S)-phenylpropyl)valeramide, MS: m/e 405.1 [M+H]$^+$.

b) In an analogous manner to that described in Example 1c), from 3(RS)-(tert-butoxyformamido)-5,5,5-trifluoro-2(RS)-hydroxy-N-(1(S)-phenylpropyl)valeramide there was obtained 3(RS)-(tert-butoxyformamido)-5,5,5-trifluoro-2-oxo-N-(1(S)-phenylpropyl)valeramide, $^1$H NMR (400 MHz, DMSO) δ: 0.75–0.85 (t,3H), 1.25–1.35 (d,9H), 1.65–1.85 (m,2H), 2.45–2.8 (m,2H), 4.6–4.7 (m,1H), 4.8–4.9 (m,1H), 7.15–7.4 (m,5H), 7.55 (d,0.5H), 7.65 (d,0.5H), 9.1 (d,1H).

EXAMPLE 17 i) In an analogous manner to that described in Example 1i), but using 3(RS)-(tert-butoxyformamido)-5,5,5-trifluoro-2-oxo-N-(1(R)-phenylpropyl)valeramide in place of 3(RS)-(tert-butoxyformamido)-5,5,5-trifluoro-2',4'-dimethyl-2-oxovaleranilide there was obtained 3(RS)-[[N-[N-[N-[N-[N-[3-(tert-butoxycarbonyl)propionyl]-O-tert-butyl-L-α-aspartyl]-O-tert-butyl-L-αglutamyl]-2-methyl-L-phenylalanyl]-3-methyl-L-valyl]-L-leucyl]amino]-5,5,5-trifluoro-2-oxo-N-(1(R)-phenylpropyl)valeramide, MS: m/e 1203.0 [M+H]$^+$.

ii) In an analogous manner to that described in Example 1ii), from 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro- 2-oxo-N-(1(R)-phenylpropyl)valeramide there was obtained 3(RS)-[[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-2-oxo-N-(1(R)-phenypropyl)valeramide, MS: m/e 1034.4 [M+H]$^+$.

The 3(RS)-(tert-butoxyformamido)-5,5,5-trifluoro-2-oxo-N-(1(R)-phenylpropyl)valeramide used as the starting material was prepared as follows:

a) In an analogous manner to that described in Example 1b), from 3(RS)-(tert-butoxyformamido)-5,5,5-trifluoro-2(RS)-hydroxyvaleric acid and (R)-α-methylbenzylamine there was obtained 3(RS)-(tert-butoxyformamido)-5,5,5-trifluoro-2(RS)-hydroxy-N-(1(R)-phenylpropyl)valeramide, MS: m/e 405.1 [M+H]$^+$.

b) In an analogous manner to that described in Example 1c), from 3(RS)-(tert-butoxyformamido)-5,5,5-trifluoro-2(RS)-hydroxy-N-(1(R)-phenylpropyl)valeramide there was obtained 3(RS)-(tert-butoxyformamido)-5,5,5-trifluoro-2-oxo-N-(1(R)-phenylpropyl)valeramide, $^1$H NMR (400 MHz, DMSO) δ: 0.75–0.85 (t,3H), 1.25–1.35 (d,9H), 1.65–1.85 (m,2H), 2.45–2.8 (m,2H), 4.6–4.7 (m,1H), 4.8–4.9 (m,1H), 7.15–7.4 (m,5H), 7.55 (d,0.5H), 7.65 (d,0.5H), 9.1 (d,1H).

EXAMPLE 18 i) In an analogous manner to that described in Example 1i), but using 3(RS)-(tert-butoxyformamido)-5,5,5-trifluoro-2-oxo-N-(1(S)-phenylbutyl)valeramide in place of 3(RS)-(tert-butoxyformamido)-5,5,5-trifluoro-2',4'-dimethyl-2-oxovaleranilide there was obtained 3(RS)-[[N-[N-[N-[N-[N-[3-(tert-butoxycarbonyl)propionyl]-O-tert-butyl-L-α-aspartyl]-O-tert-butyl-L-αglutamyl]-2-methyl-L-phenylalanyl]-3-methyl-L-valyl]-L-leucyl]amino]- 5,5,5-trifluoro-2-oxo-N-(1(S)-phenylbutyl)valeramide, MS: m/e 1216.9 [M+H]$^+$.

ii) In an analogous manner to that described in Example 1ii), from 3(RS)-[[N-[N-[N-[N-[N-[3-(tert-butoxycarbonyl)

propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-2-oxo-N-(1(S)-phenylbutyl) valeramide there was obtained 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-2-oxo-N-(1(S)-phenylbutyl)valeramide, MS: m/e 1048.6 [M+H]$^+$.

The 3(RS)-(tert-butoxyformamido)-5,5,5-trifluoro-2-oxo-N-(1(S)-phenylbutyl)valeramide used as the starting material was prepared as follows:

a) In an analogous manner to that described in Example 1b), from 3(RS)-(tert-butoxyformamido)-5,5,5-trifluoro-2(RS)-hydroxyvaleric acid and (S)-α-propylbenzylamine there was obtained 3(RS)-(tert-butoxyformamido)-5,5,5-trifluoro-2(RS)-hydroxy-N-(1(S)-phenylbutyl)valeramide, MS: m/e 419.1 [M+H]$^+$.

b) In an analogous manner to that described in Example 1c), from 3(RS)-(tert-butoxyformamido)-5,5,5-trifluoro-2(RS)-hydroxy-N-(1(S)-phenylbutyl)valeramide there was obtained 3(RS)-(tert-butoxyformamido)-5,5,5-trifluoro-2-oxo-N-(1(S)-phenylbutyl)valeramide, MS: m/e 361.1 [M+H—C$_4$H$_8$]$^+$.

EXAMPLE 19 i) In an analogous manner to that described in Example 1i), but using 3(RS)-(tert-butoxyformamido)-5,5,5-trifluoro-2-oxo-N-(1(R)-phenylbutyl)valeramide in place of 3(RS)-(tert-butoxyformamido)-5,5,5-trifluoro-2',4'-dimethyl-2-oxovaleranilide there was obtained 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]-amino]-5,5,5-trifluoro-2-oxo-N-(1(R)-phenylbutyl)valeramide, MS: m/e 1217.0 [M+H]$^+$.

ii) In an analogous manner to that described in Example 1ii), from 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-2-oxo-N-(1(R)-phenylbutyl) valeramide there was obtained 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-2-oxo-N-(1(R)-phenylbutyl)valeramide, MS: m/e 1048.6 ]M+H]$^+$.

The 3(RS)-(tert-butoxyformamido)-5,5,5-trifluoro-2-oxo-N-(1(R)-phenylbutyl)valeramide used as the starting material was prepared as follows:

a) In an analogous manner to that described in Example 1b), from 3(RS)-(tert-butoxyformamido)-5,5,5-trifluoro-2(RS)-hydroxyvaleric acid and (R)-α-propylbenzlamine there was obtained 3(RS)-(tert-butoxyformamido)-5,5,5-trifluoro-2(RS)-hydroxy-N-(1(R)-phenylbutyl)valeramide, MS: m/e 419.1 [M+H]$^+$.

b) In an analogous manner to that described in Example 1c), from 3(RS)-(tert-butoxy-formamido)-5,5,5-trifluoro-2(RS)-hydroxy-N-(1(R)-phenylbutyl)valeramide there was obtained 3(RS)-(tert-butoxyformamido)-5,5,5-trifluoro-2-oxo-N-(1(R)-phenylbutyl)valeramide, MS: m/e 361.0 [M+H—C$_4$H$_8$]$^+$.

EXAMPLE 20 i) In an analogous manner to that described in Example 1i), but using 3(RS)-(tert-butoxyformamido)-5,5,5-trifluoro-2-oxo-N-(1(S)-phenyl-2-methylpropyl)valeramide in place of 3(RS)-(tert-butoxyformamido)-5,5,5-trifluoro-2',4'-dimethyl-2-oxovaleranilide there was obtained 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl] amino]-5,5,5-trifluoro-N-(2-methyl-1(S)-phenylpropyl)-2-oxovaleramide, MS: m/e 1216.9 [M+H]$^+$.

ii) In an analogous manner to that described in Example 1ii), from 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-N-(2-methyl-1(S)-phenylpropyl)-2-oxovaleramide there was obtained 3(RS)-[[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-N-(2-methyl-1(S)-phenylpropyl)-2-oxovaleramide, MS: m/e 1048.4 [M+H]$^+$.

The 3(RS)-(tert-butoxyformamido)-5,5,5-trifluoro-2-oxo-N-(1(S)-phenyl-2-methylpropyl)valeramide used as the starting material was prepared as follows:

a) In an analogous manner to that described in Example 1b), from 3(RS)-(tert-butoxyformamido)-5,5,5-trifluoro-2(RS)-hydroxyvaleric acid and (S)-α-isopropylbenzylamine there was obtained 3(RS)-(tert-butoxyformamido)- 5,5,5-trifluoro-2(RS)-hydroxy-N-(1(S)-phenyl-2-methylpropyl) valeramide, MS: m/e 419.1 [M+H]$^+$.

b) In an analogous manner to that described in Example 1c), from 3(RS)-(tert-butoxyformamido)-5,5,5-trifluoro-2(RS)-hydroxy-N-(1(S)-phenyl-2-methylpropyl)-valeramide there was obtained 3(RS)-(tert-butoxyformamido)-5,5,5-trifluoro-2-oxo-N-(1(S)-phenyl-2-methylpropyl) valeramide, MS: m/e 361.0 [M+H—C$_4$H$_8$]$^+$.

EXAMPLE 21 i) In an analogous manner to that described in Example 1i), but using 3(RS)-(tert-butoxyformamido)-5,5,5-trifluoro-N-[1(S)-(2-naphthyl)ethyl]-2-oxovaleramide in place of 3(RS)-(tert-butoxyformamido)-5,5,5-trifluoro-2',4'-dimethyl-2-oxovaleranilide there was obtained 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-N-[1(S)-(2-naphthyl)ethyl]-2-oxovaleramide, MS: m/e 1238.8 [M+H]$^+$.

ii) In an analogous manner to that described in Example 1ii), from 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-N-[1(S)-(2-naphthyl)ethyl]-2-oxovaleramide there was obtained 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-N-[1(S)-2-naphthyl)ethyl]-2-oxovaleramide, MS: m/e 1070.4 [M+H]$^+$.

The 3(RS)-(tert-butoxyformamido)-5,5,5-trifluoro-N-[1(S)-(2-naphthyl)ethyl]-2-oxovaleramide used as the starting material was prepared as follows:

a) In an analogous manner to that described in Example 1b), from 3(RS)-(tert-butoxyformamido)-5,5,5-trifluoro-2(RS)-hydroxyvaleric acid and (S)-1-(2-naphthyl)ethylamine there was obtained 3(RS)-(tert-butoxyformamido)-5,5,5-trifluoro-2(RS)-hydroxy-N-[1(S)-(2-naphthyl)ethyl] valeramide, MS: m/e 441.1 [M+H]$^+$.

b) In an analogous manner to that described in Example 1c), from 3(RS)-(tert-butoxyformamido)-5,5,5-trifluoro-2

(RS)-hydroxy-N-[1(S)-(2-naphthyl)ethyl]valeramide there was obtained 3(RS)-(tert-butoxyformamido)-5,5,5-trifluoro-N-[1(S)-(2-naphthyl)ethyl]-2-oxovaleramide, MS: m/e 383.0 [M+H—C$_4$H$_8$]$^+$.

EXAMPLE 22 i) In an analogous manner to that described in Example 1i), but using 3(RS)-(tert-butoxyformamido)-5,5,5-trifluoro-N-[(1(S)-(2-naphthyl)propyl]-2-oxovaleramide in place of 3(RS)-(tert-butoxyformamido)-5,5,5-trifluoro-2',4'-dimethyl-2-oxovaleranilide there was obtained 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-N-[1(S)-(2-naphthyl)propyl]-2-oxovaleramide, MS: m/e 1253.5 [M+H]$^+$.

ii) In an analogous manner to that described in Example 1ii), from 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-N-[1(S)-(2-naphthyl)propyl]-2-oxovaleramide there was obtained 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-N-[1(S)-(2-naphthyl)propyl]-2-oxovaleramide, MS: m/e 1084.4 [M+H]$^+$.

The 3(RS)-(tert-butoxyformamido)-5,5,5-trifluoro-N-[(1(S)-(2-naphthyl)propyl]-2-oxovaleramide used as the starting material was prepared as follows:

a) In an analogous manner to that described in Example 1b), from 3(RS)-(tert-butoxyformamido)-5,5,5-trifluoro-2(RS)-hydroxyvaleric acid and α(S)-ethyl-2-naphthalenemethylamine there was obtained 3(RS)-(tert-butoxyformamido)-5,5,5-trifluoro-2(RS)-hydroxy-N-[1(S)-(2-naphthyl)propyl]valeramide.

b) In an analogous manner to that described in Example 1c), from 3(RS)-(tert-butoxyformamido)-5,5,5-trifluoro-2(RS)-hydroxy-N-[1(S)-(2-naphthyl)propyl]valeramide there was obtained 3(RS)-(tert-butoxyformamido)-5,5,5-trifluoro-N-[1(S)-(2-naphthyl)propyl]-2-oxoaleramide, $^1$H NMR (400 MHz, CDCl$_3$) δ: 0.9–1.0 (t,3H), 1.35 (s,4.5H), 1.45 (s,4.5H), 1.9–2.0(m,2H), 2.75–3.1 (m,2H), 4.9–5.0 (m,1H) 5.1–5.2 (m,1H), 5.35–5.45 (m,1H), 7.2 (d,1H), 7.3–7.4 (m,1H), 7.45–7.55 (m,2H), 7.7 (d 1H), 7.8–7.9 (m,3H).

The α(S)-ethyl-2-naphthalenemethylamine used in paragraph a) was prepared as follows:

i) A solution of 10 g (58.14 mmol) of 2-naphthoic acid, 16.7 g (87.21 mmol) of 1-(3-dimethylaminopropyl)-3-ethylcarbodiimide, 13.4 g (116.5 mmol) of N-ethylmorpholine, 13.3 g (98.52 mmol) of 1-hydroxybenzotriazole and 8.5 g (87.18 mmol) of N,O-dimethylhydroxylamine in 100 ml of dichloromethane was stirred at room temperature until the reaction had finished according to thin layer chromatography. The solution was extracted with 2M hydrochloric acid and saturated sodium bicarbonate solution, dried over magnesium sulphate, filtered and evaporated to dryness. There were obtained 13 g of N,O-dimethyl 2-naphthalenecarbohydroxamate, $^1$H NMR (250 MHz, CDCl$_3$) δ: 3.4 (s,3H), 3.5 (s,3H), 7.45–7.6 (m,2H), 7.7–7.95 (m,4H) 8.2 (s,1H).

ii) 58 ml (58 mmol) of a 1 M solution of ethylmagnesium bromide in tetrahydrofuran were added dropwise to a stirred solution of 12.5 g (58 mmol) of N,O-dimethyl 2-naphthalenecarbohydroxamate in 50 ml of tetrahydrofuran under a nitrogen atmosphere. The mixture was stirred overnight and then the reaction was quenched by the addition of water and diethyl ether. The ethereal layer was separated, dried over magnesium sulphate, filtered and evaporated to dryness. The residue was purified by chromatography on silica gel using 33% ethyl acetate in petroleum ether for the elution to give 2.1 g of 1-(2-naphthyl)-1-propanone, NMR: (250 MHz, CDCl$_3$) δ: 1.2–1.3 (t,3H), 3.1–3.2 (q,2H), 7.5–7.6 (m,2H), 7.8–8.1 (m,4H), 8.45 (s,1H).

iii) A mixture of 2.1 g (11.41 mmol) of 1-(2-naphthyl)-1-propanone and 2.1 g (30.22 mmol) of hydroxylamine hydrochloride was heated under reflux in 30 ml of pyridine for 1 hour. The solution was evaporated to dryness and the residue was partitioned between water and diethyl ether. The organic layer was washed twice with 2M hydrochloric acid, dried over magnesium sulphate, filtered and evaporated to dryness to give 2.04 g of 1-(2-naphthyl)-1-propanone oxime as a pink solid, $^1$H NMR (400 MHz, CDCL$_3$) δ: 1.2–1.3 (t,3H), 2.9–3.0 (q,2H), 7.45–7.55 (m,2H), 7.8–7.9 (m,4H), 8.02 (s,1H).

iv) A mixture of 2 g (10 mmol) of 1-(2-naphthyl)-1-propanone oxime, 3.6 g (55.1 mmol) of zinc, 0.4 g (6 mmol) of ammonium acetate, 50 ml of aqueous ammonia, 12 ml of ethanol and 5 ml of dimethylformamide was stirred and heated at 85° C. for 1 hour. The mixture was cooled to room temperature, diluted with diethyl ether and basified with 35% aqueous sodium hydroxide solution. The ethereal layer was separated, dried over magnesium sulphate, filtered and evaporated to dryness to give 1.8 g of α(RS)-ethyl-2-naphthalenemethylamine as a colorless oil, $^1$H NMR (400 MHz, CDCL$_3$) δ: 0.9 (t,3H), 1.7–1.8 (br,s,2H), 3.9–4.0 (t,1H), 4.1–4.2 (q,2H), 7.4–7.5 (m,3H), 7.75 (s,1H), 7.8–7.9 (m,3H).

v) A mixture of 1.3 g (7.03 mmol) of (RS)-ethyl-2-naphthalenemethylamine, 1 g (6.02 mmol) of (S)-(+)-α-methoxyphenylacetic acid, 1.1 g (8.15 mmol) of 1-hydroxybenzotriazole and 1.4 g (7.31 mmol) of 1-(3-dimethylaminopropyl)-3-ethylcarbodiimide was stirred in 20 ml of dichloromethane for 18 hours. The solution was extracted with 2M hydrochloric acid and saturated sodium bicarbonate solution, then dried over magnesium sulphate, filtered and evaporated to dryness. The residue was chromatographed on silica gel using 25% ethyl acetate in petroleum ether and then 33% ethyl acetate in petroleum ether for the elution. After trituration with 50% diethyl ether in petroleum ether there were obtained 950 mg of 2(S)-methoxy-N[1(S)-(2-naphthyl)propyl]-2-phenylacetamide, $^1$H NMR (400 MHz, DMSO) δ: 0.8–0.85 (t,3H), 1.8–1.9 (m,2H), 3.3 (s,3H), 4.7 (s,1H), 4.8–4.9 (q,1H),7.25–7.5 (m,8H), 7.68 (s,1H), 7.75–7.9 (m,3H), 8.5–8.6 (d,1H), which was eluted first, and 850 mg of 2(S)methoxy-N-[1(R)-(2-naphthyl)propyl]-2-phenylacetamide, $^1$H NMR (400 MHz, DMSO) δ: 0.8–0.9 (t,3H), 1.75–1.9 (m,2H), 3.3 (s,3H), 4.7 (s,1H), 4.8–4.9 (q,1H), 7.25–7.5 (m,8H), 7.7 (s,1H), 7.75–7.9 (m,3H), 8.5–8.6 (d,1H), which was eluted subsequently.

vi) 950 mg (2.85 mmol) of 2(S)methoxy-N-[1(S)-(2-naphthyl)propyl]-2-phenylacetamide were stirred and refluxed in a mixture of 10 ml of ethanol and 10 ml of concentrated hydrochloric acid for 48 hours. The solution was evaporated to dryness and the residue was dissolved in water and washed twice with diethyl ether. The aqueous solution was separated, basified with sodium bicarbonate and extracted twice with ethyl acetate. The combined ethyl acetate solutions were dried over magnesium sulphate, filtered and evaporated to dryness to give α(S)-ethyl-2-naphthalenemethylamine as a colorless oil, $^1$H NMR (400 MHz, CDCl$_3$) δ: 0.8–0.9 (t,3H), 1.6–1.7 (br,s,2H), 1.65–1.75 (m,2H), 3.9 (t,1H), 7.35–7.45 (m,3H), 7.67 (s,1H), 7.7–7.8 (m,3H).

EXAMPLE 23 i) In an analogous manner to that described in Example 1i), but using 3(RS)-(tert-butoxyformamido)-5,5,5-trifluoro-N-[(2-naphthyl)propyl]-2-oxovaleramide in place of 3(RS)-(tert-butoxyformamido)-5,5,5-trifluoro-2',4'-dimethyl-2-oxovaleranilide there was obtained 3(RS)-[[N-[N-[N-[N-[3-(tert-butoxycarbonyl)propionyl]-O-tert-butyl-L-α-aspartyl]-O-tert-butyl-L-αglutamyl]-2-methyl-L-phenylalanyl]-3-methyl-L-valyl]-L-leucyl]amino]-5,5,5-trifluoro-N-[(2-naphthyl)propyl]-2-oxovaleramide, MS: m/e 1252.9 [M+H]$^+$.

ii) In an analogous manner to that described in Example 1ii), from 3(RS)-[[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-N-[(2-naphthyl)propyl]-2-oxovaleramide there was obtained 3(RS)-[[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-N-[(2-naphthyl)propyl]-2-oxovaleramide, MS: m/e 1084.4 [M+H]$^+$.

The 3(RS)-(tert-butoxyformamido)-5,5,5-trifluoro-N-[(1R)-(2-naphthyl)propyl]-2-oxovaleramide used as the starting material was prepared as follows:

a) In an analogous manner to that described in Example 1b), from 3(RS)-(tert-butoxyformamido)-5,5,5-trifluoro-2(RS)-hydroxyvaleric acid and α(R)-ethyl-2-naphthalenemethylamine there was obtained 3(RS)-(tert-butoxyformamido)-5,5,5-trifluoro-2(RS)-hydroxy-N-[(2-naphthyl)propyl]valeramide.

b) In an analogous manner to that described in Example 1c), from 3(RS)-(tert-butoxyformamido)-5,5,5-trifluoro-2(RS)-hydroxy-N-[(2-naphthyl)propyl]valeramide there was obtained 3(RS)-(tert-butoxyformamido)-5,5,5-trifluoro-N-[1(R)-(2-naphthyl)propyl]-2-oxovaleramide, $^1$H NMR (400 MHz, CDCl$_3$) δ: 0.9–1.0 (t,3H), 1.35 (s,4.5H)), 1.45 (s,4.5H), 1.9–2.0 (m,2H), 2.75–3.1 (m,2H), 4.9–5.0 (m,1H), 5.1–5.2 (m,1H), 5.35–5.45 (m,1H), 7.2 (d,1H), 7.3–7.4 (m,1H), 7.45–7.55 (m,2H), 7.7 (d,1H), 7.8–7.9 (m,3H).

The ethyl-2-naphthalenemethylamine, $^1$H NMR (400 MHz, CDCl$_3$) δ: 0.8–0.9 (t,3H), 1.75–1.85 (m,2H), 1.75–2.0 (br. s, 2H), 3.95–4.0 (t,1H), 7.4–7.5 (m,3H), 7.75 (s,1H), 7.8–7.85 (m,3H), used in paragraph a) was prepared as described in Example 22vi) from 2(S)-methoxy-N-[(2-naphthyl)propyl]-2-phenylacetamide (prepared as described in Example 22v)).

EXAMPLE 24 i) In an analogous manner to that described in Example 1i), but using 3(RS)-(tert-butoxyformamido)-2-oxo-N-propylheptanamide in place of 3(RS)-(tert-butoxyformamido)-5,5,5-trifluoro-2',4'-dimethyl-2-oxovaleranilide there was obtained 3(RS)-[[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-2-oxo-N-propylheptanamide, MS: m/e 1100.7 [M+H]$^+$.

ii) In an analogous manner to that described in Example 1ii), from 3(RS)-[[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-2-oxo-N-propylheptanamide there was obtained 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-2-oxo-N-propylheptanamide, MS: m/e 932.4 [M+H]$^+$.

The 3(RS)-(tert-butoxyformamido)-2-oxo-N-propylheptanamide used as the starting material was prepared as follows:

a) In an analogous manner to that described in Example 1a), but using N,O-dimethyl 2(RS)-(tert-butoxyformamido)hexanohydroxamate in place of N,O-dimethyl 2(RS)-(tert-butoxyformamido)-4,4,4-trifluorobutyrohydroxamate there was obtained 3(RS)-tert-butoxyformamido)-2(RS)-hydroxyheptanoic acid, $^1$H NMR (250 MHz, CDCl$_3$) δ: 0.75–0.9 (m,3H), 1.2–1.7 (m, 15H), 3.85–4.05 (m,1H), 4.15–4.35 (m,1H), 4.85–5.0 (dd,1H), 5.8–6.0 (m,1H).

b) In an analogous manner to that described in Example 1b), from 3(RS)-(tert-butoxyformamido)-2(RS)-hydroxyheptanoic acid and n-propylamine there was obtained 3(RS)-(tert-butoxyformamido)-2(RS)-hydroxy-N-propylheptanamide, MS: m/e 303.2 [M+H]$^+$.

c) In an analogous manner to that described in Example 1c), from 3(RS)-(tert-butoxyformamido)-2(RS)-hydroxy-N-propylheptanamide there was obtained 3(RS)-(tert-butoxyformamido)-2-oxo-N-propylheptanamide, $^1$H NMR (250 MHz, CDCl$_3$) δ: 0.8–0.95 (m,6H), 1.2–1.7 (m, 15H), 3.15–3.35 (q,2H), 4.95–5.1 (m,1H), 6.8–7.0 (m,1H).

EXAMPLE 25 i) In an analogous manner to that described in Example 1i), but using 3(RS)-(tert-butoxyformamido)-5,5,5-trifluoro-2-oxovaleramide in place of 3(RS)-(tert-butoxyformamido)-5,5,5-trifluoro-2',4'-dimethyl-2-oxovaleranilide there was obtained 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-2-oxovaleramide.

ii) 80 mg (0.074 mmol) of 3(RS)-[[N-[N-[N-[N-[N-[3-(tert-butoxycarbonyl)propionyl]-O-tert-butyl-L-αaspartyl]-O-tert-butyl-L-α-glutamyl]-2-methyl-L-phenylalanyl]-3-methyl-L-valyl]-L-leucyl]amino]-5,5,5-trifluoro-2-oxovaleramide were dissolved in 3 ml of trifluoroacetic acid and the solution was stirred at room temperature for 30 minutes. The solution was then diluted with 10 ml of toluene and the solvent was removed by evaporation. The residue was purified by reverse-phase high-pressure liquid chromatography on a Dynamax C18 column (5 micron, 300A, 21.4×50 mm). The elution gradient comprised 90% SSA 10% SSB to 95% SSB 5% SSA over 8.5 minutes (SSA is 0.1% trifluoroacetic acid in water; SSB is 0.1% trifluoroacetic acid in 70% acetonitrile and 30% water). After lyophilization overnight there were obtained 12 mg of 3(R or S)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-2-oxo-valeramide (diastereoisomer A); MS: m/e 916.3 [M+H]$^+$, which was eluted first, and 8 mg of 3(R or S)-[[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-2-oxo-valeramide (diastereoisomer B); MS: m/e 916.2 [M+H]$^+$, which was eluted subsequently.

The 3(RS)-(tert-butoxyformamido)-5,5,5-trifluoro-2-oxovaleramide used as the starting material can be prepared as follows:

a) In an analogous manner to that described in Example 1b), from 3(RS)-(tert-butoxyformamido)-5,5,5-trifluoro-2(RS)-hydroxyvaleric acid and ammonia there was obtained 3(RS)-(tert-butoxyformamido)-5,5,5-trifluoro-2(RS)-hydroxyvaleramide, $^1$H NMR (250 MHz, DMSO) δ: 1.35–1.45 (d,9H), 2.0–2.5 (m,2H), 3.95–4.1 (m,1H), 4.15–4.4 (m,1H), 5.5 (d,0.5H), 5.7 (d,0.5H), 5.85 (d,1H), 6.5–6.6 (m,1H), 6.9–7.0 (m,1H).

b) In an analogous manner to that described in Example 1c), from 3(RS)-(tert-butoxyformamido)-5,5,5-trifluoro-2 (RS)-hydroxyvaleramide there was obtained 3(RS)-(tert-butoxyformamido)-5,5,5-trifluoro-2-oxovaleramide, $^1$H NMR (250 MHz, DMSO) δ: 1.4 (s,9H), 2.6–2.9 (m,2H), 5.0–5.1 (m,1H), 6.5 (d,1H), 7.3–7.4 (s,2H).

Alternatively, the starting material can be prepared as follows:

c) A solution of 580 mg (2.03 mmol) of 3(RS)-(tert-butoxyformamido)-5,5,5-trifluoro-2(RS)-hydroxyvaleramide and 1.16 g (6.11 mmol) of 4-toluenesulphonic acid monohydrate in 10 ml of acetonitrile was stirred until the reaction had finished according to thin-layer chromatography. 10 ml of diethyl ether were added and the 3(RS)-amino-5,5,5-trifluoro-2(RS)-hydroxyvaleramide p-toluenesulphonate (1:1) which formed was removed by filtration and added to a solution of 1.06 g (1.156 mmol) of N-[N-[N-[N-[N-[3-(tert-butoxycarbonyl) propionyl]-O-tert-butyl-L-α-aspartyl]-O-tert-butyl-L-α-glutamyl]-2-methyl-L-phenylalanyl]-3-methyl-L-valyl]-L-leucine (prepared as described in Example 1), 321 mg (2.79 mmol) of N-ethylmorpholine, 268 mg (1.4 mmol) of 1-(3-dimethylaminopropyl)-3-ethylcarbodiimide hydrochloride and 190 mg (1.4 mmol) of 1-hydroxy-7-azabenzotriazole in 20 ml of dichloromethane. The mixture was stirred at room temperature until the reaction had finished according to thin-layer chromatography. The solution was washed with 2M hydrochloric acid and saturated sodium bicarbonate solution, then dried over anhydrous magnesium sulphate, filtered and evaporated to dryness. The residue was triturated with diethyl ether/petroleum ether (1:1) and the solid was removed by filtration to give 0.7 g of 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-2(RS)-hydroxyvaleramide as a white solid, MS: m/e 1086.6 [M+H]$^+$.

d) A solution of 0.7 g (0.645 mmol) of 3(RS)-[[N-[N-[N-[N-[N-[3-(tert-butoxycarbonyl)-propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-2(RS)-hydroxyvaleramide and 328 mg (0.773 mmol) of 1,1,1-triacetoxy-1,1-dihydro-1,2-benziodoxol-3 (1H)-one in 20 ml of dichloromethane was stirred under a nitrogen atmosphere at room temperature for 30 minutes. A further 328 mg. (0.773 mmol) of 1,1,1-triacetoxy-1,1-dihydro-1,2-benziodoxol-3(1H)-one were added and the mixture was stirred for 1 hour. The solution was extracted with a solution of 10 g of sodium thiosulphate in 40 ml of saturated sodium bicarbonate solution then dried over anhydrous magnesium sulphate, filtered and evaporated to dryness. The residue was triturated with diethyl ether/petroleum ether (1:1) and the solid was removed by filtration to give 660 mg of 3(RS)-[[N-[N-[N-[N-[N-[3-(tert-butoxycarbonyl) propionyl]-O-tert-butyl-L-α-aspartyl]-O-tert-butyl-L-α-glutamyl]- 2-methyl-L-phenylalanyl]-3-methyl-L-valyl]-L-leucyl]amino]-5,5,5-trifluoro-2-oxovaleramide as a white solid. MS: m/e 1084.5 [M+H]$^+$.

EXAMPLE 26 i) In an analogous manner to that described in Example 1i), from 3(RS)-(tert-butoxyformamido)-5,5,5-trifluoro-N-(4-nitrobenzyl)-2-oxovaleramide via 3(RS)-amino-5,5,5-trifluoro-N-(4-nitrobenzyl)-2-oxovaleramide p-toluenesulphonate (1:1), $^1$H NMR (400 MHz, DMSO) δ: 2.28 (m,3H), 2.85–2.9 (m,1H), 3.05–3.15, m,1H)), 4.4–4.6, (m,2H), 5.0–5.1 (m,1H) 7.1 (d,2H), 7.45–7.6 (m,4H), 8.15–8.25 (m,2H), 8.5 (br,s,1H), there was obtained 3(RS)-[[N-[N-[N-[N-[N-[3-(tert-butoxycarbonyl)propionyl]-O-tert-butyl-L-α-aspartyl]-O-tert-butyl-L-αglutamyl]-2-methyl-L-phenylalanyl]-3-methyl-L-valyl]-L-leucyl] amino]-5,5,5-trifluoro-N-(4-nitrobenzyl)-2-oxovaleramide; MS: mle 1219.5 [M+H].

ii) In an analogous manner to that described in Example 1ii), from 3(RS)-[[N-[N-[N-[N-[N-[3-(tert-butoxycarbonyl) propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-N-(4-nitrobenzyl)-2-oxovaleramide there was obtained 3(RS)-[[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-N-(4-nitrobenzyl)-2-oxovaleramide, map. 142–144° C., as a white solid.

The 3(RS)-(tert-butoxyformamido)-5,5,5-trifluoro-N-(4-nitrobenzyl)-2-oxovaleramide used as the starting material was prepared as follows:

a) In an analogous manner to that described in Example 1b), from 3(RS)-(tert-butoxyformamido)-5,5,5-trifluoro-2 (RS)-hydroxyvaleric acid and 4-nitrobenzylamine there was obtained 3(RS)-(tert-butoxyformamido)-5,5,5-trifluoro-2 (RS)-hydroxy-N-(4-nitrobenzyl)-valeramide, MS: m/e 422 [M+H].

b) In an analogous manner to that described in Example 1c), from 3(RS)-(tert-butoxyformamido)-5,5,5-trifluoro-2 (RS)-hydroxy-N-(4-nitrobenzyl)-valeramide there was obtained 3(RS)-(tert-butoxyformamido)-5,5,5-trifluoro-N-(4-nitrobenzyl)-2-oxovaleramide, $^1$H NMR (400 MHz, DMSO) δ: 1.35 (s, 9H), 2.55 (m, 1H), 2.8 (m, 1H), 4.45 (d, 2H), 4.95 (m, 1H), 7.55 (d, 2H), 7.65 (m, 1H), 8.2 (d, 2H), 9.45 (m, 1H).

EXAMPLE 27 i) In an analogous manner to that described in Example 1i), from 3(RS)-(tert-butoxyformamido)-5,5,5-trifluoro-N-(3-methoxybenzyl)-2-oxovaleramide via 3(RS)-amino-5,5, 5-trifluoro-N-(3-methoxybenzyl)-2-oxovaleramide p-toluenesulphonate (1:1), $^1$H NMR (400 MHz, DMSO) δ: 2.3 (s,3H), 2.85–3.15 (m,2H), 3.7 (s,3H), 4.25–4.45 (m,2H), 5.1 (s,1H), 6.8–6.9 (m,3H), 7.1 (d,2H), 7.25 (m,1H), 7.45–7.55 (m,3H), 8.15 (br,s,1H) there was obtained 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl] amino]-5,5,5-trifluoro-N-(3-methoxybenzyl)-2-oxovaleramide, MS: m/e 1205.3 [M+H].

ii) In an analogous manner to that described in Example 1ii), from 3(RS)-[[N-[N-[N-[N-[N-[3-(tert-butoxycarbonyl) propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-N-(3-methoxybenzyl)-2-oxovaleramide there was obtained 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl] amino]-5,5,5-trifluoro-N-(3-methoxybenzyl)-2-oxovaleramide as a white solid; MS: m/e 1036.4 [M+H]

The 3(RS)-(tert-butoxyformamido)-5,5,5-trifluoro-N-(3-methoxybenzyl)2-oxovaleramide used as the starting material was prepared as follows:

a) In an analogous manner to that described in Example 1b), from 3(RS)-(tert-butoxyformamido)-5,5,5-trifluoro-2

(RS)-hydroxyvaleric acid and 3-methoxybenzylamine there was obtained 3(RS)-(tert-butoxyformamido)-5,5,5-trifluoro-2(RS)-hydroxy-N-(3-methoxybenzyl)-valeramide, MS m/e 407 [M+H].

b) In an analogous manner to that described in Example 1c), from 3(RS)-(tert-butoxyformamido)-5,5,5-trifluoro-2(RS)-hydroxy-N-(3-methoxybenzyl)-valeramide there was obtained 3(RS)-(tert-butoxyformamido)-5,5,5-trifluoro-N-(3-methoxybenzyl)-2-oxovaleramide, $^1$H NMR (400 MHz, DMSO) δ: 1.35 (s, 9H), 2.5–2.65 (m, 1H), 2.7–2.85 (m, 1H), 3.7 (s, 3H), 4.25–4.4 (m, 2H), 4.9–5.0 (m, 1H), 6.75–6.85 (m, 3H), 7.2 (t, 1H), 7.6 (d, 1H), 9.25 (t, 1H).

EXAMPLE 28 i) In an analogous manner to that described in Example 1i), from 3(RS)-(tert-butoxyformamido)-5,5,5-trifluoro-N-(3-nitrobenzyl)-2-oxovaleramide via 3(RS)-amino-5,5,5-trifluoro-N-(3-nitrobenzyl)-2-oxovaleramide p-toluenesulphonate (1:1), $^1$H NMR (400 MHz, DMSO) δ: 2.25 (s,3H), 2.85–3.0 (m,1H), 3.05–3.15 (m,1H) 4.35–4.55 (m,2H), 5.0–5.1 (m,1H), 7.10 (d,2H), 7.45 (d,2H), 7.55–7.80 (m,2H), 8.1–8.2 (m,2H), 8.5 (s,1H), 9.0 (s,1H), 9.75 (m,1H), there was obtained 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-N-(3-nitrobenzyl)-2-oxovaleramide, MS: m/e 1219.8 [M+H].

ii) In an analogous manner to that described in Example 1ii), from 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-N-(3-nitrobenzyl)-2-oxovaleramide there was obtained 3(RS)-[[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-N-(3-nitrobenzyl)-2-oxovaleramide, MS: m/e 1051.4 [M+H].

The 3(RS)-(tert-butoxyformamido)-5,5,5-trifluoro-N-(3-nitrobenzyl)-2-oxovaleramide used as the starting material was prepared as follows:

a) In an analogous manner to that described in Example 1b), from 3(RS)-(tert-butoxyformamido)-5,5,5-trifluoro-2(RS)-hydroxyvaleric acid and 3-nitrobenzylamine there was obtained 3(RS)-(tert-butoxyformamido)-5,5,5-trifluoro-2(RS)-hydroxy-N-(3-nitrobenzyl)-valeramide, 1H NMR (400 MHz, DMSO) δ: 1.3, 1.35 (2s, 9H), 2.2–2.5 (m, 2H), 3.95–4.05 (m, 1H), 4.1–4.2 (m, 1H), 4.3–4.45 (m, 2H), 6.0, 6.15 (2d, 1H), 6.40, 6.95 (2d, 1H), 7.58 (m, 1H) 7.7 (m, 1H), 8.1 (m, 2H), 8.65, 8.70 (2t, 1H).

b) In an analogous manner to that described in Example 1c), from 3(RS)-(tert-butoxyformamido)-5,5,5-trifluoro-2(RS)-hydroxy-N-(3-nitrobenzyl)-valeramide there was obtained 3(RS)-(tert-butoxyformamido)-5,5,5-trifluoro-N-(3-nitrobenzyl)-2-oxovaleramide; $^1$H NMR (400 MHz, DMSO) δ: 1.30 (s, 9H), 2.50–2.65 (m, 1H), 2.70–2.85 (m, 1H), 4.4–4.5 (m, 2H), 4.90–4.95 (m, 1H), 7.6–7.65, m, 2H), 7.7 (d, 1H), 8.10–8.20 (m, 2H), 9.4–9.50 (m, 1H)

EXAMPLE 29 i) In an analogous manner to that described in Example 1i), from 3(RS)-(tert-butoxyformamido)-5,5,5-trifluoro-N-[(4-tert-butoxymethyl)benzyl]-2-oxovaleramide via 3(RS)-amino-5,5,5-trifluoro-N-[4-(tert-butoxymethyl)benzyl]-2-oxovaleramide p-toluenesulphonate (1:1), $^1$H NMR (400 MHz, DMSO) δ: 1.20 (s,9H), 2.27 (s,3H), 2.85–2.95 (m,1H), 3.05–3.15 (m,1H), 4.3–4.4 (m,4H), 5.05–5.10 (m,1H), 7.10 (d,2H), 7.15–7.25 (m,4H), 7.45 (d,2H), 8.5 (br,s,3H), 9.6 (t,1H), there was obtained 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-N-[4-(tert-butoxymethyl)benzyl]-5,5,5-trifluoro-2-oxovaleramide, MS: m/e 1260.9 [M+H].

ii) In an analogous manner to that described in Example 1ii), from 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-N-[4-(tert-butoxymethyl)benzyl]-5,5,5-trifluoro-2-oxovaleramide there was obtained 3(RS)-[[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-N-[4-(hydroxymethyl)benzyl]-2-oxovaleramide as a white solid, MS: m/e 1036.3 [M+H].

The 3(RS)-(tert-butoxyformamido)-5,5,5-trifluoro-N-[(4-tert-butoxymethyl)benzyl]2-oxovaleramide used as the starting material was prepared as follows:

a) In an analogous manner to that described in Example 1b), from 3(RS)-(tert-butoxyformamido)-5,5,5-trifluoro-2(RS)-hydroxyvaleric acid and 4-(tert-butoxymethyl) benzylamine there was obtained 3(RS)-(tert-butoxyformamido)-5,5,5-trifluoro-2(RS)-hydroxy-N-[4-(tert-butoxymethyl)benzyl]-valeramide, MS: m/e 463 [M+H].

b) In an analogous manner to that described in Example 1c), from 3(RS)-(tert-butoxyformamido)-5,5,5-trifluoro-2(RS)-hydroxy-N-[4-(tert-butoxymethyl)benzyl]-valeramide there was obtained 3(RS)-(tert-butoxyformamido)-5,5,5-trifluoro-N-[4-(tert-butoxymethyl)benzyl]-2-oxovaleramide, $^1$H NMR (400 MHz, DMSO) δ: 1.25 (s, 9H), 1.4 (s, 9H), 2.55–2.7 (m, 1H), 2.8–2.90 (m, 1H), 4.3–4.45 (m, 4H), 4.95–5.05 (m, 1H), 7.25–7.30 (m, 4H), 7.65 (d, 1H), 9.30 (t, 1H).

EXAMPLE 30 i) In an analogous manner to that described in Example 1i), from 3(RS)-(tert-butoxyformamido)-5,5,5-trifluoro-N-(4-tert-butoxybenzyl)-2-oxovaleramide via 3(RS)-amino-5,5,5-trifluoro-N-(4-hydroxybenzyl)-2-oxovaleramide p-toluenesulphonate (1:1), MS: m/e 291.1 [M+H], there was obtained 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-N-(4-hydroxybenzyl)-2-oxovaleramide, MS: m/e 1190.8 [M+H].

ii) In an analogous manner to that described in Example 1ii), from 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-N-(4-tert-butoxybenzyl)-2-oxovaleramide there was obtained 3(RS)-[[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-N-(4-hydroxybenzyl)-2-oxovaleramide as a white solid, MS: m/e 1022.3 [M+H].

The 3(RS)-(tert-butoxyformamido)-5,5,5-trifluoro-N-(4-tert-butoxybenzyl)-2-oxovaleramide used as the starting material was prepared as follows:

a) In an analogous manner to that described in Example 1b), from 3(RS)-(tert-butoxyformamido)-5,5,5-trifluoro-2

(RS)-hydroxyvaleric acid and tert-butoxybenzylamine there was obtained 3(RS)-(tert-butoxyformamido)-5,5,5-trifluoro-2(RS)-hydroxy-N-(4-tert-butoxybenzyl)-valeramide, $^1$H NMR (400 MHz, DMSO) δ: 1.25 (s, 9H), 1.35 (s, 9H), 2.25–2.5 (m, 2H), 3.95–4.0 (m, 1H0, 4.1–4.30 (m, 3H), 5.83 (d, 1H), 6.45 (d, 1H), 6.85 (d, 2H), 7.15 (d, 1H), 8.35 (t, 1H).

b) In an analogous manner to that described in Example 1c), from 3(RS)-(tert-butoxyformamido)-5,5,5-trifluoro-2(RS)-hydroxy-N-(4-tert-butoxybenzyl)-valeramide there was obtained 3(RS)-(tert-butoxyformamido)-5,5,5-trifluoro-N-(4-tert-butoxybenzyl)-2-oxovaleramide, MS: m/e 447 [M+H].

EXAMPLE 31 i) In an analogous manner to that described in Example 1i), from 3(RS)-(tert-butoxyformamido)-5,5,5-trifluoro-2-oxo-N-(2-thienl)valeramide via 3(RS)-amino-5,5,5-trifluoro-2-oxo-N-(2-thienl)valeramide p-toluenesulphonate (1:1), MS: m/e 281 [M+H], there was obtained 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-2-oxo N-(2-thienl)valeramide, $^1$H NMR (400 MHz, DMSO) δ: (0.7–0.9 (m, 15H), 1.2 (s, 3H), 1.35 (s, 27H), 1.5–1.8 (m, 4H), 2.05–2.15 (m, 2H), 2.22 (m, 2H), 2.3–2.45 (m, 6H), 2.5–3.0 (m, 4H), 4.1–4.6 (m, 6H), 4.6–4.7 (m, 1H), 6.90–7.10 (m, 6H), 7.3–7.4 (m, 1H), 7.7–8.2 (m, 5H).

ii) In an analogous manner to that described in Example 1ii), from 3(RS)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-5,5,5-trifluoro-2-oxo N-(2-thienl)valeramide there was obtained 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-2-oxo-N-(2-thienl)valeramide as a white solid, MS: m/e 1012.2 [M+H].

The 3(RS)-(tert-butoxyformamido)-5,5,5-trifluoro-2-oxo-N-(2-thienl)valeramide used as the starting material was prepared as follows:

a) In an analogous manner to that described in Example 1b), from 3(RS)-(tert-butoxyformamido)-5,5,5-trifluoro-2(RS)-hydroxyvaleric acid and 2-thienl)valeramide there was obtained 3(RS)-(tert-butoxyformamido)-5,5,5-trifluoro-2(RS)-hydroxy-N-(2-thienl)valeramide, MS: m/e 383 [M+H].

b) In an analogous manner to that described in Example 1c), from 3(RS)-(tert-butoxyformamido)-5,5,5-trifluoro-2(RS)-hydroxy-N-(2-thienl)valeramide there was obtained 3(RS)-(tert-butoxyformamido)-5,5,5-trifluoro-2-oxo-N-(2-thienl)valeramide, MS: m/e 207.3 [M+H].

EXAMPLE 32 i) 300 mg of p-toluenesulphonic acid were added to a solution of 200 mg of 3(S)-(tert-butoxyformamido)-2-oxo-N-(1(S)-phenylpropyl)heptanamide in 4 ml of acetonitrile and the mixture was heated briefly (about 15 seconds) until all components had passed into solution. The mixture was then stirred at room temperature for 20 minutes. The solvent was removed and the crude 3(S)-amino-2-oxo-N-(1(S)-phenylpropyl)hexanamide p-toluenesulphonate (1:1) was used immediately without further purification.

87 mg of 1-hydroxy-7-azabenzotriazole, 122 mg of 1-(3-dimethylaminopropyl)-3-ethylcarbodiimide hydrochloride and 0.2 ml of 4-ethylmorpholine were added to a suspension of 250 mg of N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucine (prepared as described in Example 1) in 10 ml of dichloromethane. A solution of the crude 3(S)-amino-2-oxo-N-(1(S)-phenylpropyl)hexanamide p-toluenesulphonate (1:1) in 10 ml of dichloromethane was added and the mixture was stirred overnight at room temperature. The mixture was then diluted with dichloromethane and washed in sequence with 5% citric acid solution, saturated sodium bicarbonate solution and saturated brine. The organic phase was dried over anhydrous magnesium sulphate and the solvent was evaporated. The crude product was then purified by chromatography on silica gel using 3.5% methanol in dichloromethane for the elution to give 200 mg of 3(S)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-2-oxo-N-(1(S)-phenylpropyl)heptanamide, MS: m/e 1176 [M+H]+.

ii) 20 mg of 3(S)-[[N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucyl]amino]-2-oxo-N-(1S)-phenylpropyl)heptanamide were treated with 2 ml of trifluoroacetic acid for 30 minutes. The trifluoroacetic acid was evaporated and the crude mixture was purified by chromatography on silica gel using dichloromethane/methanol/acetic acid/water (120:15:3:2) for the elution. Trituration gave 3(S)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-2-oxo-N-(1(S)-phenylpropyl)heptanamide, as a white solid. MS: m/e 1008.4 [M+H]+.

The 3(S)-(tert-butoxyformamido)-2-oxo-N-(1(S)-phenylpropyl)heptanamide used as the starting material was prepared as follows:

a) 1 g of (E)-2-heptenoic acid was dissolved in 20 ml of toluene and the resulting solution was heated to 80° C. A solution of 11.2 ml of N,N-dimethylformamide di-tert-butyl acetal in 10 ml of toluene was added and the mixture was stirred at 80° C. for 30 minutes. The mixture was cooled and washed in sequence with water, saturated sodium bicarbonate solution and saturated brine. The organic phase was dried over anhydrous magnesium sulphate and evaporated. The residue was purified by chromatography on silica gel using 10% ethyl acetate in hexane for the elution to give 0.85 g of tert-butyl (E)-2-heptenoate as a colorless oil, $^1$H NMR (400 MHz, CDCl$_3$) δ: 0.85 (t,3H), 1.2–1.4 (m,4H), 1.45 (s,9H), 2.1 (m,2H), 5.65 (dt,1H), 6.8 (d,1H).

b) A solution of 0.66 ml of (S)-(–)-N-benzyl-α-methylbenzylamine in 10 ml of tetrahydrofuran was cooled to 0° C. and 1.88 ml of a 1.6M solution of n-butyllithium in hexane were added dropwise via a syringe. The resulting dark pink solution was stirred at 0° C. for 45 minutes and then cooled to –78° C. A solution of 0.184 g of tert-butyl (E)-2-heptenoate in 2 ml of anhydrous diethyl ether was added and the mixture was stirred for 2 hours at –78° C. 0.37 g of solid (1S)-(+)-(10-camphorsulphonyl)oxaziridine was added and the mixture was stirred at –78° C. for 1 hour. The mixture was warmed to 0° C. and a saturated ammonium chloride solution was added. The tetrahydrofuran was evaporated and the aqueous phase was diluted with water and extracted with dichloromethane. The organic phase was dried over magnesium sulphate, evaporated and purified by chromatography on silica gel using a 10% solution of diethyl ether in hexane for the elution to give 0.35 g of tert-butyl 3(S)-[N-benzyl-N-(α(S)-methylbenzyl)amino]-2(S)-hydroxyheptanoate as a colorless oil, MS: m/e 412.2 [M+H]+.

c) A solution of 0.5 g of tert-butyl 3(S)-[N-benzyl-N-(α(S)-methylbenzyl)amino]-2(S)-hydroxyheptanoate in acetic acid containing 0.2 g of palladium-on-charcoal was hydrogenolyzed overnight at 0.5 MPa. The catalyst was removed by filtration and the acetic acid was evaporated. The crude product was dissolved in dichloromethane and washed with saturated sodium bicarbonate solution. The aqueous phase was extracted with dichloromethane and the combined organic layers were washed with saturated sodium bicarbonate solution, dried over magnesium sulphate and evaporated to give 0.26 g of tert-butyl 3(S)-amino-2(S)-hydroxyheptanoate, MS: m/e 218.3 [M+H]+.

d) 0.26 g of tert-butyl 3(S)-amino-2(S)-hydroxyheptanoate was treated with 2 ml of trifluoroacetic acid for 30 minutes. The trifluoroacetic acid was evaporated and the residue was evaporated twice with toluene. Trituration with diethyl ether gave 0.155 g of 3(S)-amino-2(S)-hydroxyheptanoic acid trifluoroacetate as a white solid, MS: m/e 162 [M+H]+.

e) A solution of 2.2 g of di-tert-butyl dicarbonate in 20 ml of saturated sodium bicarbonate solution was added to a solution 1.43 g. of 3(S)-amino-2(S)-hydroxyheptanoic acid trifluoroacetate in 20 ml of dioxan. The mixture was stirred for 2 hours at room temperature and 0.5 g of di-tert-butyl dicarbonate and 10 ml of saturated sodium bicarbonate solution were added. The mixture was stirred overnight and a further 0.5 g of di-tert-butyl dicarbonate and 10 ml of saturated sodium bicarbonate solution were added. The mixture was stirred until thin layer chromatography using dichloromethane/methanol/acetic acid/water (60:18:2:3) for the elution indicated that the 3(S)-amino-2(S)-hydroxyheptanoic acid trifluoroacetate had been consumed. The dioxan was evaporated and the aqueous layer was extracted with diethyl ether. Ethyl acetate was added to the aqueous layer, which was acidified with 2M hydrochloric acid. The organic phase was separated and the aqueous phase was extracted with ethyl acetate. The combined organic layers were dried over magnesium sulphate and evaporated to give 3(S)-(tert-butoxyformamido)-2(S)-hydroxyheptanoic acid, MS: m/e 262.5 [M+H]+.

f) 229 mg of 1-hydroxybenzotriazole monohydrate, 287 mg of 1-(3-dimethylaminopropyl)-3-ethylcarbodiimide hydrochloride and 148 mg of (S)-(−)-1-phenylpropylamine were added in sequence to a solution of 260 mg of 3(S)-(tert-butoxyformamido)-2(S)-hydroxyheptanoic acid in 10 ml of dichloromethane. The mixture was stirred at room temperature for 3 hours, then diluted with dichloromethane and washed in sequence with 5% citric acid solution, saturated sodium bicarbonate solution and saturated brine. The organic phase was dried over anhydrous magnesium sulphate and the solvent was evaporated to give 285 mg of 3(S)-(tert-butoxyformamido)-2(S)-hydroxy-N-(1(S)-phenylpropyl)heptanamide, MS: m/e 379.1 [M+H]+.

g) 0.383 g of 1,1,1-triacetoxy-1,1-dihydro-1,2-benziodoxol-3(1H)-one was added to a solution of 0.285 g of 3(S)-(tert-butoxyformamido)-2(S)-hydroxy-N-(1(S)-phenylpropyl)heptanamide in 20 ml of dichloromethane. The mixture was stirred at room temperature for 30 minutes and then a further 30 mg of 1,1,1-triacetoxy-1,1-dihydro-1,2-benziodoxol-3(1H)-one were added. The mixture was stirred at room temperature for 30 minutes and then diluted with ethyl acetate. The solution was extracted with a solution of 10 g of sodium thiosulphate in 40 ml of saturated sodium bicarbonate solution. The aqueous layer was extracted with ethyl acetate and the combined organic layers were washed with water, dried over magnesium sulphate and evaporated. The residue was purified by chromatography on silica gel using 20% ethyl acetate in hexane for the elution to give 200 mg of 3(S)-(tert-butoxyformamido)-2-oxo-N-(1(S)-phenylpropyl)heptanamide, MS: m/e 377.1 [M+H]+.

EXAMPLE 33

16 mg of a mixture of (Z)-N-benzyl-3(S)-[[N-[N-[N-[N-[(3-carboxypropionyl)-L-α-aspartyl]-L-α-glutamyl]-2-methyl-L-phenylalanyl]-3-methyl-L-valyl]-L-leucyl]amino]-2(RS)-hydroxy-5-heptenamide and (Z)-N-benzyl-3(S)-[[N-[N-[N-[N-[(3-carboxypropionyl)-L-α-aspartyl]-L-α-glutamyl]-2-methyl-L-phenylalanyl]-3-methyl-L-valyl]-L-leucyl]amino]-2(RS)-formyloxy-5-heptenamide were treated with 0.1 ml of a 2M aqueous solution of ammonia at room temperature for 30 minutes. An additional 0.1 ml of an aqueous solution of ammonia was added and the mixture was stirred for a further 2 hours. The solvent was evaporated and the crude (Z)-N-benzyl-3(S)-[[N-[N-[N-[N-[(3-carboxypropionyl)-L-α-aspartyl]-L-α-glutamyl]-2-methyl-L-phenylalanyl]-3-methyl-L-valyl]-L-leucyl]amino]-2(RS)-hydroxy-5-heptenamide obtained was dissolved in dimethylformamide. 6.3 mg aliquots of 1,1,1-triacetoxy-1,1-dihydro-1,2-benziodoxol-3(1H)-one were added over a period of 3 hours until mass spectroscopy indicated that the majority of the (Z)-N-benzyl-3(S)-[[N-[N-[N-[N-[N-[(3-carboxypropionyl)-L-α-aspartyl]-L-α-glutamyl]-2-methyl-L-phenylalanyl]-3-methyl-L-valyl]-L-leucyl]amino]-2(RS)-hydroxy-5-heptenamide had been consumed. The solvent was evaporated and the crude product was purified by chromatography on silica gel using dichloromethane/methanol/acetic acid/water (120:15:3:2) for the elution followed by mass spectrum controlled reverse-phase high pressure liquid chromatography to give (Z)-N-benzyl-3(RS)-[[N-[N-[N-[N-[N-[(3-carboxypropionyl)-L-α-aspartyl]-L-α-glutamyl]-2-methyl-L-phenylalanyl]-3-methyl-L-valyl]-L-leucyl]amino]-2-oxo-5-heptenamide, MS: m/e 978.8 [M+H]+.

The mixture of (Z)-N-benzyl-3(S)-[[N-[N-[N-[N-[N-[(3-carboxypropionyl)-L-α-aspartyl]-L-α-glutamyl]-2-methyl-L-phenylalanyl]-3-methyl-L-valyl]-L-leucyl]amino]-2(RS)-hydroxy-5-heptenamide and (Z)-N-benzyl-3(S)-[[N-[N-[N-[N-[(3-carboxypropionyl)-L-α-aspartyl]-L-α-glutamyl]-2-methyl-L-phenylalanyl]-3-methyl-L-valyl]-L-leucyl]amino]-2(RS)-formyloxy-5-heptenamide used as the starting material was prepared as follows:

a) 2.26 g (9.87 mmol) of (Z)-N-(tert-butoxycarbonyl)-L-2-(2-butenyl)glycine were dissolved in 50 ml of anhydrous tetrahydrofuran followed by 1.15 g (11.79 mmol) of N,O-dimethylhydroxylamine hydrochloride, 1.6 g (10.46 mmol) of 1-hydroxybenzotriazole monohydrate, 2.27 g (11.88 mmol) of 1-(3-dimethylaminopropyl)-3-ethylcarbodiimide hydrochloride and 5.8 ml of ethyldiisopropylamine and the resulting solution was stirred at room temperature overnight. The solution was washed with saturated sodium hydrogen carbonate solution and then with saturated sodium chloride solution and dried over anhydrous magnesium sulphate. Removal of the solvent by evaporation yielded 2.46 g of N,O-dimethyl (Z)-2(S)-(tert-butoxyformamido)-4-hexeneohydroxamate as a colorless oil which was used without further purification, $^1$H NMR (250 MHz, CDCl$_3$) δ: 1.4 (s,9H), 1.6 (d,3H), 2.35 (m,1H), 2.5 (m,1H), 3.2 (s,3H), 3.75 (s,3H), 4.7 (m,IH), 5.2 (d, 1H), 5.35 (m,1H), 5.6 (m,1H).

b) 1.56 g (5.74 mmol) of N,O-dimethyl (Z)-2(S)-(tert-butoxyformamido)-4-hexeneohydroxamate were dissolved in 10 ml of anhydrous tetrahydrofuran and the solution was cooled to 0° C. 2.6 ml of a 1M solution of lithium aluminum hydride in tetrahydrofuran were added and the resulting solution stirred for 30 minutes. The reaction was quenched by the dropwise addition of 15 ml of saturated potassium hydrogen sulphate solution followed by 30 ml of diethyl ether. The resulting two-phase system was stirred vigorously for 1 hour. The organic phase was extracted with saturated sodium hydrogen carbonate solution followed by saturated sodium chloride solution and then dried over magnesium sulphate. After removal of the solvent by evaporation the aldehyde was used without further purification.

c) 0.79 g (3.71 mmol) of the aldehyde was dissolved in a saturated solution of hydrogen chloride in methanol and the resulting solution was stirred at room temperature for 2 hours. After removal of the solvent by evaporation the dimethyl acetal was used without purification.

d) 0.15 g (0.16 mmol) of [N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucine (prepared as described in Example 1), 0.033 g (0.2 mmol) of 1-hydroxybenzotriazole monohydrate, 0.047 g (0.25 mmol) of 1-(3-dimethylaminopropyl)-3-ethylcarbodiimide hydrochloride and 0.77 g (6.69 mmol) of 4-ethylmorpholine were dissolved in 15 ml of dichloromethane. 0.05 g (0.22 mmol) of the dimethyl acetal dissolved in 5 ml of dichloromethane was added and the resulting solution stirred at room temperature for 3 days. The solution was washed with 5% citric acid solution and then with saturated sodium hydrogen carbonate solution and saturated sodium chloride solution and subsequently dried over magnesium sulphate. After removal of the solvent by evaporation the crude product was purified by chromatography on silica gel using 2% methanol in dichloromethane for the elution to give 0.092 g of (Z)-N2-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[1(S)-(dimethoxymethyl)-3-pentenyl]-L-leucinamide, as a white foam, MS: m/e 1027.9 [M+H]+.

e) 0.05 g (0.04 mmol) of (Z)-N2-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[1(S)-(dimethoxymethyl)-3-pentenyl]-L-leucinamide was dissolved in 4 ml of a 1:1 solution of dichloromethane and trifluoroacetic acid containing 3 drops of water. The resulting solution was stirred for 1 hour at room temperature. After removal of the solvent by evaporation the crude product was triturated in diethyl ether to give 0.03 g of (Z)-2(S)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-4-hexenal as a white solid, MS: m/e 845.7 [M+H]+.

f) A solution of 18 mg of (Z)-2(S)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-4-hexenal in 2 ml of dichloromethane was treated with 0.2 ml of formic acid and 0.02 ml of benzyl isocyanide. The mixture was stirred at room temperature for 1 hour and then evaporated. The crude product was purified by chromatography on silica gel using dichloromethane/methanol/acetic acid/water (240:12:3:2) for the elution to give 16 mg of a mixture of (Z)-N-benzyl-3(S)-[[N-[N-[N-[N-(3-carboxypropionyl)-L-α-aspartyl]-L-α-glutamyl]-2-methyl-L-phenylalanyl]-3-methyl-L-valyl]-L-leucyl]amino]-2(RS)-hydroxy-5-heptenamide and (Z)-N-benzyl-3(S)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-2(RS)-formyloxy-5-heptenamide MS: m/e 980.5 [M1+H]+; 1008.5 [M2+H].

EXAMPLE 34

N-Benzyl-3(RS)-[[N-[N-[N-[N-(3-carboxypropionyl)-L-α-aspartyl]-L-α-glutamyl]-2-methyl-L-phenylalanyl]-3-methyl-L-valyl]-L-leucyl]amino]-amino]-4-cyano-2-oxobutyramide, MS: m/e 963.6 [M+H]+, was prepared in an analogous manner to that described in Example 33 using N2-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[2-cyano-1(S)-dimethoxymethyl) ethyl]-L-leucinamide in place of (Z)-N2-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[1(S)-(dimethoxymethyl)-3-pentenyl]-L-leucinamide.

The following intermediates were obtained:

2(RS)-[[N-[N-[N-[N-(3-carboxypropionyl)-L-α-aspartyl]-L-α-glutamyl]-2-methyl-L-phenylalanyl]-3-methyl-L-valyl]-L-leucyl]amino]-3-cyanopropionaldehyde, MS: m/e 830.4 [M+H]+;

N-benzyl-3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-4-cyano-2(RS)-hydroxybutyramide, MS: m/e 965.4 [M+H]+;

and

N-benzyl-3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-4-cyano-2(RS)-formyloxybutyramide, MS: m/e 993.5 [M+H]+.

The N2-[[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[2-cyano-1(S)-dimethoxymethyl)ethyl]-L-leucinamide was prepared as follows:

A solution of 615 mg of 3-cyano-N-[(9-fluorenyl) methoxycarbonyl]-L-alanine, 576 mg of 1-(3-dimethylaminopropyl)-3-ethylcarbodiimide hydrochloride, 459 mg of 1-hydroxybenzotriazole monohydrate, 345 mg of 4-ethylmorpholine and 293 mg of N,O-dimethylhydroxylamine hydrochloride in 20 ml of dichloromethane was stirred for 3 hours. The mixture was washed with 2M hydrochloric acid and then with saturated sodium hydrogen carbonate solution. The organic layer was dried over anhydrous magnesium sulphate and the solvent was removed by evaporation. Trituration of the residue gave 570 mg of N,O-dimethyl 3-cyano-2(S)-[(9-fluorenyl) methoxyformamido]propionohydroxamate as a white solid that was used without further purification.

1.2 ml of a 1M solution of lithium aluminum hydride in tetrahydrofuran were added to a solution of 570 mg of N,O-dimethyl 3-cyano-2(S)-[(9-fluorenyl) methoxyformamido]propionohydroxamate in 10 ml of anhydrous tetrahydrofuran at 0° C. The mixture was stirred at 0° C. for 30 minutes and then quenched by the dropwise addition of saturated potassium hydrogen sulphate solution followed by diethyl ether. The resulting two-phase system was stirred vigorously for 1 hour. The organic phase was washed with saturated sodium hydrogen carbonate solution and then with saturated sodium chloride solution and subsequently dried over magnesium sulphate. Removal of the solvent by evaporation gave 450 mg of 3-cyano-2(S)-[(9-fluorenyl)methoxyformamido]propionaldehyde as a white solid that was used without further purification.

A solution of 440 mg of 3-cyano-2(S)-[(9-fluorenyl)methoxyformamido]propionaldehyde in 4 ml of dry methanol containing 0.5 ml of trimethyl orthoformate and 20 mg of p-toluenesulphonic acid was stirred overnight at room temperature. The solvent was evaporated and the crude product was dissolved in ethyl acetate and washed with water. The organic layer was dried over magnesium sulphate and purified by chromatography on silica gel using 40% ethyl acetate in hexane for the elution to give 430 mg of 9-fluorenyl [3-cyano-1(S)-(dimethoxymethyl)ethyl] carbamate as a white solid, MS: m/e 367 [M+H]$^+$.

410 mg of 9-fluorenyl [3-cyano-1(S)-(dimethoxymethyl)ethyl]carbamate were dissolved in 10 ml of dichloromethane/piperidine (4:1) and the mixture obtained was stirred at room temperature for 30 minutes. The solvents were evaporated and the crude product was purified by chromatography on silica gel using a 50% solution of ethyl acetate in hexane followed by 10% methanol in dichloromethane for the elution to give 130 mg of amine. The amine was dissolved in 5 ml of dichloromethane and 183 mg of N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucine (prepared as described in Example 1), 30 mg of 1-hydroxybenzotriazole monohydrate and 58 mg of 1-(3-dimethylaminopropyl)-3-ethylcarbodiimide hydrochloride were added. The mixture was stirred overnight at room temperature and then washed with 2M hydrochloric acid and then with saturated sodium hydrogen carbonate solution. The organic layer was dried over anhydrous magnesium sulphate and the solvent was removed by evaporation. Purification by chromatography on silica gel using 4% methanol in dichloromethane for the elution gave 120 mg of N2-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[2-cyano-1(S)-(dimethoxymethyl)ethyl]-L-leucinamide as a white solid, MS: m/e 1044.5 [M+H]$^+$.

EXAMPLE 35

N-Benzyl-3(RS)-[[N-[N-[N-[N-(3-carboxypropionyl)-L-α-aspartyl]-L-α-glutamyl]-2-methyl-L-phenylalanyl]-3-methyl-L-valyl]-L-leucyl]amino]-2-oxo-5-heptynamide, MS: m/e 976.6 [M+H]$^+$, was prepared in an analogous manner to that described in Example 33 using 2(S)-(tert-butoxyformamido)-6-hexynoic acid in place of (Z)-N-(tert-butoxycarbonyl)-L-2-(2-butenyl)glycine.

The following intermediates were obtained:

N,O-dimethyl 2(S)-(tert-butoxyformamido)-4-hexynohydroxamate, $^1$H NMR (250 MHz, CDCl$_3$) δ: 1.4 (s,9H), 1.75 (m,3H), 2.55 (m,2H), 3.2 (s,3H), 3.55 (s,3H), 4.75 (m,1H), 5.35 (m,1H);

N2-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[1(S)-(dimethoxymethyl)-3-pentynyl]-L-leucinamide, MS: m/e 1079.8 [M$^+$Na]$^+$;

2(S)-[[N-[N-[N-[N-(3-carboxypropionyl)-L-α-aspartyl]-L-α-glutamyl]-2-methyl-L-phenylalanyl]-3-methyl-L-valyl]-L-leucyl]amino]-4-hexynal, MS: m/e 843.6 [M+H]+;

N-benzyl-3(S)-[[N-[N-[N-[N-(3-carboxypropionyl)-L-α-aspartyl]-L-α-glutamyl]-2-methyl-L-phenylalanyl]-3-methyl-L-valyl]-L-leucyl]amino]-2(RS)-hydroxy-5-heptynamide, MS: m/e 978.5 [M+H]$^+$;

and

N-benzyl-3(S)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-2(RS)-formyloxy-5-heptynamide, MS: m/e 1006.5 [M+H]$^+$.

EXAMPLE 36

N-Benzyl-3(S)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-2-oxo-4-phenylbutyramide, MS: m/e 1014.4 [M+H]$^+$, was prepared in an analogous manner to that described in Example 33 using N-(tert-butoxycarbonyl)-L-phenylalanine in place of (Z)-N-(tert-butoxycarbonyl)-L-2-(2-butenyl)glycine.

The following intermediates were obtained:

N,O-dimethyl 2(S)-(tert-butoxyformamido)-3-phenylpropionohydroxamate, $^1$H NMR (250 MHz, CDCl$_3$) δ: 1.35 (s,9H), 2.8–3.1 (m,2H), 3.15 (s,3H), 3.6 (s,3H), 4.9 (m,1H), 5.1 (m,1H), 7.1–7.3 (m,5H);

N2-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[1(S)-(dimethoxymethyl)-2-phenylethyl]-L-leucinamide, MS: m/e 1118.0 [M+Na]$^+$;

2(S)-[[N-[N-[N-[N-(3-carboxypropionyl)-L-α-aspartyl]-L-α-glutamyl]-2-methyl-L-phenylalanyl]-3-methyl-L-valyl]amino]-3-phenylpropionaldehyde, MS: m/e 881.7 [M+H]$^+$;

N-benzyl-3(S)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-2(RS)-hydroxy-4-phenylbutyramide, MS: m/e 1016.5 [M+H]$^+$;

and

N-benzyl-3(S)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-2(RS)-formyloxy-4-phenylbutyramide, MS: m/e 1044.6 [M+H]$^+$.

EXAMPLE 37

N-Benzyl-4-butylthio-3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-2-oxobutyramide, MS: m/e 1026.6 [M+H]$^+$, was prepared in an analogous manner to that described in Example 33 using S-butylthio-N-(tert-butoxycarbonyl)-L-cysteine in place of (Z)-N-(tert-butoxycarbonyl)-L-2-(2-butenyl)glycine.

The following intermediates were obtained:

N,O-dimethyl 2(R)-(tert-butoxyformamido)-3-(butylthio)propionohydroxamate, $^1$H NMR (250 MHz, CDCl$_3$) δ: 0.9 (t,3H), 1.3–1.6 (m,4H), 1.45 (s,9H), 2.55 (t,2H), 2.75 (dd, 1H), 2.9 (dd,1H), 3.2 (s,3H), 3.8 (s,3H), 4.85 (m,1H), 5.35 (m,1H);

N2-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[2-(butylthio)-1(R)-(dimethoxymethyl)ethyl]-L-leucinamide, MS: m/e 1129.6 [M+Na]$^+$;

2(R)-[[N-[N-[N-[N-(3-carboxypropionyl)-L-α-aspartyl]-L-α-glutamyl]-2-methyl-L-phenylalanyl]-3- methyl-L-valyl]-L-leucyl]amino]-3-(butylthio) propionaldehyde, MS: m/e 893.4 [M+H]$^+$;

N-benzyl-4-butylthio-3(R)-[[N-[N-[N-[N-[3-carboxypropionyl)-L-α-aspartyl]-L-α-glutamyl]-2-methyl-L-phenylalanyl]-3-methyl-L-valyl]-L-leucyl] amino]-2(RS)-hydroxybutyramide, MS: m/e 1028.5 [M+H]$^+$;

and

N-benzyl-4-butylthio-3(R)-[[N-[N-[N-[N-[3-carboxypropionyl)-L-α-aspartyl]-L-α-glutamyl]-2-methyl-L-phenylalanyl]-3-methyl-L-valyl]-L-leucyl] amino]-2(RS)-formyloxybutyramide, MS: m/e 1056.5 [M+H]$^+$.

EXAMPLE 38

N-Benzyl-4-benzylthio-3(RS)-[[N-[N-[N-[N-[N-[3-carboxypropionyl)-L-α-aspartyl]-O-tert-butyl-L-α-glutamyl]-2-methyl-L-phenylalanyl]-3-methyl-L-valyl]-L-leucyl]amino]-2-oxobutyramide, MS: m/e 1060.8 [M+H]$^+$, was prepared in an analogous manner to that described in Example 33 using S-benzyl-N-(tert-butoxycarbonyl)-L-cysteine in place of (Z)-N-(tert-butoxycarbonyl)-L-2-(2-butenyl)glycine.

The following intermediates were obtained:

N,O-dimethyl 3-benzylthio-2(R)-(tert-butoxyformamido) propionohydroxamate, $^1$H NMR (250 MHz, CDCl$_3$) δ: 1.45 (s,9H), 2.6 (dd,1H), 2.8 (dd,1H), 3.2 (s,3H), 3.7 (m,5H), 4.9 (m,1H), 5.3 (m,1H) 7.2–7.35 (m,5H);

N1-[2-benzylthio-1(R)-(dimethoxymethyl)ethyl]-N2-[N-[N-[N-[N-[3-(tert-butoxycarbonyl)-propionyl]-O-tert-butyl-L-α-aspartyl]-O-tert-butyl-L-α-glutamyl]-2-methyl-L-phenylalanyl]-3-methyl-L-valyl]-L-leucinamide, MS: 1163.9 [M+Na]$^+$;

3-benzylthio-2(R)-[[N-[N-[N-[N-[N-[3-carboxypropionyl)-L-α-aspartyl]-L-α-glutamyl]-2-methyl-L-phenylalanyl]-3-methyl-L-valyl]-L-leucyl] amino]propionaldehyde, MS: m/e 927.6 [M+H]$^+$;

N-benzyl-4-benzylthio-3(R)-[[N-[N-[N-[N-[3-carboxypropionyl)-L-α-aspartyl]-L-α-glutamyl]-2-methyl-L-phenylalanyl]-3-methyl-L-valyl]-L-leucyl] amino]-2(RS)-hydroxybutyramide, MS: m/e 1062.5 [M+H]$^+$;

and

N-benzyl-4-benzylthio-3(R)-[[N-[N-[N-[N-[3-carboxypropionyl)-L-α-aspartyl]-L-α-glutamyl]-2-methyl-L-phenylalanyl]-3-methyl-L-valyl]-L-leucyl] amino]-2(RS)-formyloxybutyramide, MS: mle 1090.7 [M+H]$^+$.

EXAMPLE 39

N-Benzyl-3(RS)-[[N-[N-[N-[N-[N-[3-carboxypropionyl)-L-α-aspartyl]-L-α-glutamyl]-2-methyl-L-phenylalanyl]-3-methyl-L-valyl]-L-leucyl]amino]-4-(5-oxazolyl)-2-oxobutyramide, MS: m/e 1005.8 [M+H]$^+$, was prepared in an analogous manner to that described in Example 33 using (N-(tert-butoxy)-3,(5-oxazolyl)-DL-alanine in place of (Z)-N-(tert-butoxycarbonyl)-L-2-(2-butenyl)glycine.

The following intermediates were obtained:

N,O-dimethyl 2(RS)-(tert-butoxyformamido)-3-(5-oxazolyl)propionohydroxamate, $^1$H NMR (250 MHz, CDCl$_3$) δ: 1.35 (s,9H), 2.7–3.1 (m,2H), 3.15 (s,3H), 3.7 (s,3H), 4.9 (m,1H), 5.25 (m,1H), 6.8 (s,1H), 7.75 (s,1H).

N2-[N-[N-[N-[3-(tert.butoxycarbonyl)propionyl]-O-tert-butyl-L-α-aspartyl]-O-tert-butyl-L-α-glutamyl]-2-methyl-L-phenylalanyl]-3-methyl-L-valyl]-N 1-[1 (RS)-(dimethoxymethyl)-2-(5-oxazolyl)ethyl]-L-leucinamide, MS: m/e 1086.8 [M+H]$^+$;

α(RS)-[[N-[N-[N-[N-[N-[3-(carboxypropionyl)-L-α-aspartyl]-L-α-glutamyl]-2-methyl-L-phenylalanyl]-3-methyl-L-valyl]-L-leucyl]amino]-5-oxazolepropionaldehyde, MS: m/e 872.5 [M+H]$^+$;

N-benzyl-3(RS)-[[N-[N-[N-[N-[3-(carboxypropionyl)-L-α-aspartyl]-L-α-glutamyl]-2-methyl-L-phenylalanyl]-3-methyl-L-valyl]-L-leucyl] amino]-2(RS)-hydroxy-4-(5-oxazolyl)butyramide, MS: m/e 1007.5 [M+H]$^+$;

and

N-benzyl-3(RS)-[[N-[N-[N-[N-[3-(carboxypropionyl)-L-α-aspartyl]-L-α-glutamyl]-2-methyl-L-phenylalanyl]-3-methyl-L-valyl]-L-leucyl] amino]-2(RS)-formyloxy-4-(5-oxazolyl)butyramide, MS: m/e 1035.5 [M+H]$^+$.

The N-(tert-butoxycarbonyl)-3-(5-oxazolyl)-DL-alanine was prepared as follows:

301 mg of a 60% dispersion of sodium hydride in mineral oil were added portionwise to 60 ml of anhydrous ethanol at 0° C. and the resulting suspension was stirred at 0° C. for 5 minutes. 1.88 g of diethyl 2-(tert-butoxyformamido) malonate were added and the mixture was warmed to room temperature. After stirring at room temperature for 10 minutes 805 mg of 5-(chloromethyl)oxazole were added. The mixture was stirred at room temperature for 30 minutes and at 60° C. for 1 hour. The solvent was evaporated and the crude product was dissolved in diethyl ether and washed with water. Sodium chloride was added to the aqueous layer, which was then extracted with diethyl ether. The combined organic layers were dried over magnesium sulphate and the solvent was removed by evaporation. Purification of the residue by chromatography on silica gel using ethyl acetate/hexane (1:2) for the elution gave diethyl 2-(tert-butoxyformamido)-2-[(5-oxazolyl)methyl]malonate, $^1$H NMR (250 MHz, CDCl$_3$) δ: 1.3 (t,6H), 1.45 (s,9H), 3.75 (s,2H), 4.2 (m,4H), 5.85 (s,1H), 6.8 (s,1H), 7.75 (s,1H).

1.5 g of diethyl 2-(tert-butoxyformamido)-2-[(5-oxazolyl)methyl]malonate were dissolved in 1.5 ml of water and 1.5 ml of ethanol. 337 mg of sodium hydroxide were added and the mixture was stirred overnight at room temperature. The mixture was then acidified to pH 5 with acetic acid and the solvent was removed by evaporation. The residue was dissolved in 5 ml of toluene and 0.64 ml of triethylamine was added. The mixture was heated at reflux for 2 hours and then the solvents were evaporated. Ethyl acetate was added and the solution was washed with saturated aqueous citric acid solution. The organic layer was dried over magnesium sulphate to give 1.224 g of crude N-(tert-butoxycarbonyl)-3(5-oxazolyl)-DL-alanine, $^1$H NMR (250 MHZ, d6-DMSO) δ: 1.4 (s,9H), 3.0–3.3 (m,2H), 6.95 (s,1H), 7.25 (m, 1H), 8.3 (s,1H).

EXAMPLE 40

0.02 g (0.006 mmol) of 3(S)-[3-(9-fluorenyl) propionamido]-2(S)-hydroxy-N-[4-[[2(S)-(4-methyl-α (RS)-phenylbenzylamino)hexanoyl]methoxy]α(RS)-(2,4-dimethoxypenyl)benzyl]heptanamide polystyrene conjugate polystyrene conjugate was suspended in and agitated with 0.7 ml of dimethylformamide/piperidine (4:1). After 5 minutes the resin was drained and resuspended in and agitated with 0.7 ml of dimethylformamide/piperidine (4:1) for a further 5 minutes. Then, the resin was drained and washed five times with 1 ml of dimethylformamide.

The resin was then suspended in a solution of 0.023 g (0.06 mmol) of N-[(9-fluorenyl)methoxycarbonyl]-L-phenylalanine in 0.34 ml of dimethylformamide and a solution of 0.019 g (0.06 mmol) of 2-(1H-benzotriazol-1-yl)-1,1,3,3-tetramethyluronium tetrafluoraborate and 0.012 g (0.12 mmol) of N-methylmorpholine in 0.34 ml of dimethylformamide was added. After agitating for 1 hour the resin was drained and washed five times with 1 ml of dimethylformamide.

The resin was resuspended in and agitated with 0.7 ml of dimethylformamide/piperidine (4:1). After 5 minutes the resin was drained and resuspended in and agitated with dimethylformamide/piperidine (4:1) for a further 5 minutes. Then, the resin was drained and washed five times with 1 ml of dimethylformamide.

The resin was then suspended in a solution of 0.021 g (0.06 mmol) of N-[(9-fluorenyl)methoxycarbonyl]-3-methyl-L-valine in 0.34 ml of dimethylformamide and treated with a solution of 0.019 g (0.06 mmol) of 2-(1H-benzotriazol-1-yl)-1,1,3,3-tetramethyluronium tetrafluoraborate and 0.012 g (0.12 mmol) of N-methylmorpholine in 0.34 ml of dimethylformamide. After agitating for 2 hours the resin was drained and washed five times with 1 ml of dimethylformamide.

The resin was resuspended in and agitated with 1 ml of dimethylformamide/piperidine (4:1). After 5 minutes the resin was drained and resuspended in and agitated with dimethylformamide/piperidine (4:1) for a further 5 minutes. Then, the resin was drained and washed five times with 1 ml of dimethylformamide.

The resin was then suspended in a solution of 0.024 g (0.06 mmol) of N-[(9-fluorenyl)methoxycarbonyl]-2-methyl-L-phenylalanine in 0.34 ml of dimethylformamide and then a solution of 0.019 g (0.06 mmol) of 2-(1H-benzotriazol-1-yl)-1,1,3,3-tetramethyluronium tetrafluoraborate and 0.012 g (0.12 mmol) of N-methylmorpholine in 0.34 ml of dimethylformamide was added. After agitating for 1 hour the resin was drained and washed five times with 1 ml of dimethylformamide.

The resin was resuspended in and agitated with 0.7 ml of dimethylformamide/piperidine (4:1). After 5 minutes the resin was drained and resuspended in and agitated with dimethylformamide/piperidine (4:1) for a further 5 minutes. Then, the resin was drained and washed five times with 1 ml of dimethylformamide.

The resin was then suspended in a solution of 0.025 g (0.06 mmol) of N-[(9-fluorenyl)methoxycarbonyl]-O-t-butyl-L-α-glutamic acid in 0.34 ml of dimethylformamide and then a solution of 0.019 g (0.06 mmol) of 2-(1H-benzotriazol-1-yl)-1,1,3,3-tetramethyluronium tetrafluoraborate and 0.012 g (0.12 mmol) of N-methylmorpholine in 0.34 ml of dimethylformamide was added. After agitating for 1 hour the resin was drained and washed five times with 1 ml of dimethylformamide.

The resin was resuspended in and agitated with 0.7 ml of dimethylformamide/piperidine (4:1). After 5 minutes the resin was drained and resuspended in and agitated with dimethylformamide/piperidine (4:1) for a further 5 minutes. Then, the resin was drained and washed five times with 1 ml of dimethylformamide.

The resin was then suspended in a solution of 0.024 g (0.06 mmol) of N-[(9-fluorenyl)methoxycarbonyl]-O-t-butyl-L-α-aspartic acid in 0.34 ml of dimethylformamide and then a solution of 0.019 g (0.06 mmol) of 2-(1H-benzotriazol-1-yl)-1,1,3,3-tetramethyluronium tetrafluoraborate and 0.012 g (0.12 mmol) of N-methylmorpholine in 0.34ml of dimethylformamide was added. After agitating for 1 hour the resin was drained and washed five times with 1 ml of dimethylformamide.

The resin was resuspended in and agitated with 0.7 ml of dimethylformamide/piperidine (4:1). After 5 minutes the resin was drained and resuspended in and agitated with dimethylformamide/piperidine (4:1) for a further 1 ml of dimethylformamide.

The resin was then suspended in a solution of 0.01 g (0.06 mmol) of tert-butyl hydrogen succinate in 0.34 ml of dimethylformamide and treated with a solution of 0.019 g (0.06 mmol) of 2-(1H-benzotriazol-1-yl)-1,1,3,3-tetramethyluronium tetrafluoraborate and 0.012 g (0.12 mmol) of N-methylmorpholine in 0.34 ml of dimethylformamide. After agitating for 2 hours the resin was drained and washed five times with 1 ml of dimethylformamide and subsequently five times with 1 ml of dichloromethane.

The resin was then suspended in a solution of 0.025 g (0.06 mmol) of 1,1,1-triacetoxy-1,1-dihydro-1,2-benziodoxol-3(1H)-one in 0.68 ml of dichloromethane. After 1 hour the resin was drained and then resuspended in and agitated with 0.025 g (0.06 mmol)of 1,1,1-triacetoxy-1,1-dihydro-1,2-benziodoxol-3(1H)-one in 0.68 ml of dichloromethane. After agitating for a further 1 hour, the resin was drained and washed five times with 1 ml of dichloromethane, then five times with 1 ml of dimethylformamide and finally five times with 1 ml of dichloromethane. 0.6 ml of trifluoroacetic acid/water (19:1) was added to the resin and the mixture was agitated for 10 minutes. The resin was then filtered from the mixture and agitated for 10 minutes with 0.6 ml of trifluoroacetic acid/water (19:1). The combined trifluoroacetic acid and water mixtures were then evaporated in a vacuum centrifuge and the residue was suspended in 1 ml of acetic acid and evaporated. There were obtained 4.1 mg of 3(S)-[[N-[N-[N-[N-(3-carboxypropionyl)-L-α-aspartyl]-L-α-glutamyl]-2-methyl-L-phenylalanyl]-3-methyl-L-valyl]-L-phenylalanyl]amino]-2-oxoheptanamide as a white solid; MS: m/e 924.8 [M+H].

The starting material was prepared as follows:

i) 74.79 ml (312 mmol) of 1,2-(di-tert-butyl) trimethylamine were added to a stirred mixture of 5 g (39 mmol) of (E)-2-heptenoic acid in 100 ml of toluene at 80° C. The mixture was stirred under reflux for 30 minutes and then cooled to room temperature. The mixture was washed in sequence with water and saturated sodium bicarbonate solution, then dried over anhydrous magnesium sulphate and filtered. The solvent was removed by evaporation. There were obtained 7.5 g of tert-butyl (E)-2-heptenoate as a yellow oil; MS: m/e 185.0 [M+H].

ii) A 1.6M solution of n-butyllithium in hexane (18.29 ml; 29 mmol) was added dropwise to a solution of 8.29 ml (39 mmol) of N-(1(R)-phenylethyl)benzylamine in 100 ml of anhydrous tetrahydrofuran while maintaining the temperature at 0° C. The mixture was stirred at 0° C. for a further 45 minutes, then cooled to −78° C. and a solution of 4.5 g (24 mmol) of tert-butyl (E)-2-heptenoate in 45 ml of anhydrous tetrahydrofuran was then added. The mixture was stirred at −78° C. for 3 hours, treated with 8.94 g (39 mmol) of solid (1S)-(+)-(camphorylsulfonyl)oxaziridine, stirred for a further 1 hour at −78° C., then warmed to 0° C. and quenched by the addition of 50 ml of saturated aqueous ammonium chloride solution. The tetrahydrofuran was removed under a vacuum and the residue was diluted with 200 ml of water and extracted with 300 ml of dichloromethane (three equivalent portions). The dichloromethane extracts were combined, washed with saturated sodium chloride, dried over anhydrous magnesium sulphate, filtered and the solvent was removed by evaporation. The resulting yellow oil was chromatographed on silica gel using 10% diethyl ether in hexane for the elution. There was obtained 3.4 g of tert-butyl 3(S)-[N-benzyl-N-(1(R)-phenylethylamino]-2(S)-hydroxyheptanoate as a colorless oil; MS: m/e 412.2 [M+H].

iii) 0.6 g of 10% palladium-on-carbon was added to a solution of (3.4 g (8.27 mmol) of tert-butyl 3(S)-[N-benzyl-N-(1(R)-phenylethylamino]-2(S)-hydroxyheptanoate in 35 ml of glacial acetic acid and the mixture was shaken in a hydrogen atmosphere. After 17 hours the catalyst was removed by filtration and the solvent was removed by evaporation. There were obtained 1.06 g of tert-butyl 3(S)-amino-2(S)-hydroxyheptanoate as a white solid; MS: m/e 218.2 [M+H].

iv) 1.37 g (4.07 mmol) of N-[(9-fluorenyl)-methoxycarbonyl]-succinimide were added to a solution of 0.93 g (4.3 mmol) of tert-butyl 3(S)-amino-2(S)-hydroxyheptanoate in 40 ml of water/dioxan (1:1). The stirred mixture was adjusted to pH 9–10 with saturated sodium carbonate solution. After 17 hours the dioxan was removed by evaporation under a vacuum. The residual aqueous phase was washed with ethyl acetate, acidified with 2M hydrochloric acid and partitioned in ethyl acetate (three 100 ml aliquots). The three ethyl acetate aliquots were combined and washed with saturated sodium chloride solution, dried over anhydrous magnesium sulphate, filtered and the solvent was removed by evaporation to give crude tert-butyl 3(S)-[(9-fluorenyl)methoxyformamido]-2(S)-hydroxyheptanoate in the form of a pale yellow oil. This oil was chromatographed on silica gel using 20% ethyl acetate in hexane followed by 40% ethyl acetate in hexane for the elution. The chromatographed material was then stirred with 10 ml of trifluoroacetic acid/dichloromethane (1:1). After 30 minutes the solvent was removed by evaporation and the residual oil was triturated with 15 ml of diethyl ether/petroleum ether (1:2). There was obtained 1 g of 3(S)-[(9-fluorenyl)methoxyformamido]-2(S)-hydroxyheptanoic acid as a white solid MS m/e 384.1 [M+H].

v) 1.1 g (0.65 mmol) of rink amide resin (Nova Biochem; 0.59 mmol/g loading) was swollen in 20 ml of N,N-dimethylformamide. After agitating for 10 minutes the resin was drained. The resin was resuspended in and agitated with 20 ml of dimethylformamide/piperidine (4:1). After 10 minutes the resin was drained and resuspended in and agitated with 20 ml of dimethylformamide/piperidine (4:1) for a further 10 minutes. Then, the resin was drained and washed five times with 20 ml of dimethylformamide.

vi) The resin was then suspended in a solution of 0.25 g (0.65 mmol) of 3(S)-[(9-fluorenyl) methoxyformamido]-2(S)-hydroxyheptanoic acid in 7.5 ml of dimethylformamide and the mixture was treated with a solution of 0.31 g (0.98 mmol) of 2-(1H-benzotriazol-1-yl)-1,1,3,3-tetramethyluronium tetrafluoraborate and 0.14 ml (1.3 mmol) of N-methylmorpholine in 7.5 ml of dimethylformamide. After agitating for 1 hour the resin was drained and washed three times with 20 ml of dichloromethane and then three times with 20 ml of N,N-dimethylformamide.

vii) The resin was then suspended in a solution of 0.31 g (6.5 mmol) of acetic acid in 7.5 ml of dimethylformamide and the mixture was treated with 2.1 g (6.5 mmol) of 2-(1H-benzotriazol-1-yl)-1,1,3,3-tetramethyluronium tetrafluoraborate and 1.43 ml (13 mmol) of N-methylmorpholine in 7.5 ml of dimethylformamide. After agitating for 1 hour the resin was drained and washed three times with 20 ml of dichloromethane, three times with 20 ml of N,N-dimethylformamide, three times with 20 ml of dichloromethane and twice with 20 ml of diethyl ether. After drying there were obtained 1.1g of 3(S)-[3-(9-fluorenyl)propionamido]-2(S)-hydroxy-N-[4-[[2(S)-(4-methyl-α(RS)-phenylbenzylamino)hexanoyl]methoxy]-α(RS)-(2,4-dimethoxypenyl)benzyl]heptanamide polystyrene conjugate as a pale brown solid (0.34 mmol/g loading estimated by quantitation of dibenzofulvene at 301 nm).

EXAMPLE 41

The following compounds of formula I were prepared in an analogous manner to that described in Example 40:

3(S)-[[N-[N-[N-[N-[N-(3-Carboxypropionyl)-L-α-aspartyl]-L-α-glutamyl]-2-methyl-L-phenylalanyl]-3-methyl-L-valyl]-L-seryl]amino]-2-oxoheptanamide as a white solid; MS: m/e 864.4 [M+H];

3(S)-[[N2-[N-[N-[N-[N-(3-carboxypropionyl)-L-α-aspartyl]-L-α-glutamyl]-2-methyl-L-phenylalanyl]-3-methyl-L-valyl]-L-glutaminyl]amino]-2-oxoheptanamide as a white solid; MS: m/e 905.4 [M+H];

3(S)-[[N-[N-[N-[N-[N-(3-carboxypropionyl)-L-α-aspartyl]-L-α-glutamyl]-2-methyl-L-phenylalanyl]-3-methyl-L-valyl]-O-(2,6-dichlorobenzyl)-L-tyrosyl]amino]-2-oxoheptanamide as a white solid; MS: m/e 1098.6 [M+H];

3(S)-[[N-[N-[N-[N-[N-(3-carboxypropionyl)-L-α-aspartyl]-L-α-glutamyl]-2-methyl-L-phenylalanyl]-3-methyl-L-valyl]-3-(3-thienyl)-Lalanyl]amino]-2-oxoheptanamide as a white solid; MS: m/e 930.4 [M+H];

3(S)-[[N-[N-[N-[N-[N-(3-carboxypropionyl)-L-α-aspartyl]-L-α-glutamyl]-2-methyl-L-phenylalanyl]-3-methyl-L-valyl]-3-cyclohexyl-L-alanyl]amino]-2-oxoheptanamide as a white solid; MS: m/e 930.6 [M+H];

3(S)-[[N-[N-[N-[N-[N-(3-carboxypropionyl)-L-α-aspartyl]-L-α-glutamyl]-2-methyl-L-phenylalanyl]-L-cyclohexylglycyl]-L-leucyl]amino]-2-oxoheptanamide as a white solid; MS: m/e 916.6 [M+H];

3(S)-[[N-[N-[N-[N-[N-(3-carboxypropionyl)-L-α-aspartyl]-L-α-glutamyl]-2-methyl-L-phenylalanyl]-O-benzyl-L-α-glutamyl]-L-leucyl]amino]-2-oxoheptanamide as a white solid; MS: m/e 996.6 [M+H];

3(S)-[[N-[N-[N-[N-[N-(3-carboxypropionyl)-L-α-aspartyl]-L-α-glutamyl]-2-methyl-L-phenylalanyl]-L-α-glutamyl]-L-leucyl]amino]-2-oxoheptanamide as a white solid; MS: m/e 906.4 [M+H];

3(S)-[[N-[N-[N-[N-[N-(3-carboxypropionyl)-L-α-aspartyl]-L-α-glutamyl]-2-methyl-L-phenylalanyl]-L-phenylalanyl]-L-leucyl]aminol-2-oxoheptanamide as a white solid; MS: m/e 924.6 [M+H];

3(S)-[[N-[N-[N-[N-[N-(3-carboxypropionyl)-L-α-aspartyl]-L-α-glutamyl]-2-methyl-L-phenylalanyl]-3-cyclohexyl-L-alanyl]-L-leucyl]amino]-2-oxoheptanamide as a white solid; MS: m/e 930.6 [M+H];

3(S)-[[N-[N-[N-[N-[N-(3-carboxypropionyl)-L-α-aspartyl]-L-α-glutamyl]-2-methyl-L-phenylalanyl]-O-benzyl-L-tyrosyl]-L-leucyl]amino]-2-oxoheptanamide as a white solid; MS: m/e 1030.6 [M+H];

3(S)-[[N-[N-[N-[N-[N-(3-carboxypropionyl)-L-α-aspartyl]-L-α-glutamyl]-2-methyl-L-phenylalanyl]-L-phenylglycyl]-L-leucyl]amino]-2-oxoheptanamide as a white solid; MS: m/e 910.4 [M+H];

3(S)-[[N-[N2-[N-[N-[N-(3-carboxypropionyl)-L-α-aspartyl]-L-α-glutamyl]-2-methyl-L-phenylalanyl]-N6-(p-toluenesulphonyl)-L-arginyl]-L-leucyl]amino]-2-oxoheptanamide as a white solid; MS: m/e 1088.6 [M+H];

3(S)-[[N-[N-[N-[N-[N-(3-carboxypropionyl)-L-α-aspartyl]-L-α-glutamyl]-2-methyl-L-phenylalanyl]-O-benzyl-L-threonyl]-L-leucyl]amino]-2-oxoheptanamide as a white solid; MS: m/e 968.6 [M+H];

3(S)-[[N-[N2-[N-[N-[N-(3-carboxypropionyl)-L-α-aspartyl]-L-α-glutamyl]-2-methyl-L-phenylalanyl]-N6-acetyl-L-lysyl]-L-leucyl]amino]-2-oxoheptanamide as a white solid; MS: m/e 947.6 [M+H];

3(S)-[[N-[N-[N-[N-[N-(3-carboxypropionyl)-L-α-aspartyl]-L-α-glutamyl]-2-methyl-L-phenylalanyl]-3-(3-thienyl)-L-alanyl]-L-leucyl]amino]-2-oxoheptanamide as a white solid; MS: m/e 930.4 [M+H];

3(S)-[[N-[N-[N-[N-[N-(3-carboxypropionyl)-L-α-aspartyl]-L-α-glutamyl]-2-methyl-L-phenylalanyl]-L-allylglycyl]-L-leucyl]amino]-2-oxoheptanamide as a white solid; MS: m/e 874.8 [M+H];

3(S)-[[N-[N-[N-[N-[N-(3-carboxypropionyl)-L-α-aspartyl]-L-α-glutamyl]-L-valyl]-3-methyl-L-valyl]-L-leucyl]amino]-2-oxoheptanamide as a white solid; MS: m/e 828.6 [M+H];

3(S)-[[N-[N-[N-[N-[N-(3-carboxypropionyl)-L-α-aspartyl]-L-α-glutamyl]-L-seryl]-3-methyl-L-valyl]-L-leucyl]amino]-2-oxoheptanamide as a white solid; MS: m/e 816.4 [M+H];

3(S)-[[N-[N-[N-[N-[N-(3-carboxypropionyl)-L-α-aspartyl]-L-α-glutamyl]-O-benzyl-L-cysteinyl]-3-methyl-L-valyl]-L-leucyl]amino]-2-oxoheptanamide as a white solid; MS: m/e 922.6 [M+H];

3(S)-[[N-[N-[N-[N-[N-(3-carboxypropionyl)-L-α-aspartyl]-L-α-glutamyl]-L-cyclohexylglycyl]-3-methyl-L-valyl]-L-leucyl]amino]-2-oxoheptanamide as a white solid; MS: m/e 868.8 [M+H];

3(S)-[[N-[N-[N-[N-[N-(3-carboxypropionyl)-L-α-aspartyl]-L-α-glutamyl]-3-cyclohexyl-L-alanyl]-3-methyl-L-valyl]-L-leucyl]amino]-2-oxoheptanamide as a white solid; MS: m/e 882.4 [M+H];

3(S)-[[N-[N-[N-[N-[N-(3-carboxypropionyl)-L-α-aspartyl]-L-α-glutamyl]-O-benzyl-L-α-glutamyl]-3-methyl-L-valyl]-L-leucyl]amino]-2-oxoheptanamide as a white solid; MS: m/e 848.8 [M+H];

3(S)-[[N-[N-[N-[N-[N-(3-carboxypropionyl)-L-α-aspartyl]-L-α-glutamyl]-O-benzyl-L-tyrosyl]-3-methyl-L-valyl]-L-leucyl]amino]-2-oxoheptanamide as a white solid; MS: m/e 982.6 [M+H];

3(S)-[[N-[N-[N-[N-[N-(3-carboxypropionyl)-L-α-aspartyl]-L-α-glutamyl]-L-phenyl leucyl]-3-methyl-L-valyl]-L-leucyl]amino]-2-oxoheptanamide as a white solid; MS: m/e 862.6 [M+H];

3(S)-[[N-[N2-[N-[N-[N-(3-carboxypropionyl)-L-α-aspartyl]-L-α-glutamyl]-N6-(p-toluenesulphonyl)-L-arginyl]-3-methyl-L-valyl]-L-leucyl]amino]-2-oxoheptanamide as a white solid; MS: m/e 1039.4 [M+H];

3(S)-[[N-[N-[N-[N-[N-(3-carboxypropionyl)-L-α-aspartyl]-L-α-glutamyl]-O-benzyl-L-threonyl]-3-methyl-L-valyl]-L-leucyl]amino]-2-oxoheptanamide as a white solid; MS: m/e 920.4 [M+H];

3(S)-[[N-[N-[N-[N-[N-(3-carboxypropionyl)-L-α-aspartyl]-L-α-glutamyl]-3-(3-thienyl)-L-alanyl]-3-methyl-L-valyl]-L-leucyl]amino]-2-oxoheptanamide as a white solid; MS: m/e 882.4 [M+H];

3(S)-[[N-[N-[N-[N-[N-(3-carboxypropionyl)-L-α-aspartyl]-L-α-glutamyl]-D-phenylglycyl]-3-methyl-L-valyl]-L-leucyl]amino]-2-oxoheptanamide as a white solid; MS: m/e 862.6 [M+H];

3(S)-[[N-[N-[N-[N-[N-(3-carboxypropionyl)-L-α-aspartyl]-O-benzyl-L-α-glutamyl]-2-methyl-L-phenylalanyl]-3-methyl-L-valyl]-L-leucyl]amino]-2-oxoheptanamide as a white solid; MS: m/e 980.6 [M+H];

3(S)-[[N-[N-[N-[N-[N-(3-carboxypropionyl)-L-α-aspartyl]-O-benzyl-L-tyrosyl]-2-methyl-L-phenylalanyl]-3-methyl-L-valyl]-L-leucyl]amino]-2-oxoheptanamide as a white solid; MS: m/e 1014.1 [M+H];

3(S)-[[N-[N-[N-[N2-[N-(3-carboxypropionyl)-L-α-aspartyl]-N6-nitro-arginyl]-2-methyl-L-phenylalanyl]-3-methyl-L-valyl]-L-leucyl]amino]-2-oxoheptanamide as a white solid; MS: m/e 962.6 [M+H];

3(S)-[[N-[N-[N-[N-[N-(3-carboxypropionyl)-L-α-aspartyl]-3-(benzyloxymethyl)-L-histidyl]-2-methyl-L-phenylalanyl]-3-methyl-L-valyl]-L-leucyl]amino]-2-oxoheptanamide as a white solid; MS: m/e 1018.6 [M+H];

3(S)-[[N-[N-[N-[N2-[N-(3-carboxypropionyl)-L-α-aspartyl]-N6-acetyl-L-lysyl]-2-methyl-L-phenylalanyl]-3-methyl-L-valyl]-L-leucyl]amino]-2-oxoheptanamide as a white solid; MS: m/e 931.6 [M+H];

3(S)-[[N-[N-[N-[N-[N-(3-carboxypropionyl)-L-α-aspartyl]-1-benzyl-L-histidyl]-2-methyl-L-phenylalanyl]-3-methyl-L-valyl]-L-leucyl]amino]-2-oxoheptanamide as a white solid; MS: m/e 988.6 [M+H];

3(S)-[[N-[N-[N-[N-[N-(3-carboxypropionyl)-L-α-aspartyl]-S,S-dioxo-L-methionyl]-2-methyl-L-phenylalanyl]-3-methyl-L-valyl]-L-leucyl]amino]-2-oxoheptanamide as a white solid; MS: m/e 924.5 [M+H];

3(S)-[[N-[N-[N-[N-[N-(3-carboxypropionyl)-L-α-aspartyl]-L-tryptophyl]-2-methyl-L-phenylalanyl]-3-methyl-L-valyl]-L-leucyl]amino]-2-oxoheptanamide as a white solid; MS: m/e 947.5 [M+H];

3(S)-[[N-[N-[N-[N-[N-(3-carboxypropionyl)-L-α-aspartyl]-O-allyl-L-α-aspartyl]-2-methyl-L-phenylalanyl]-3-methyl-L-valyl]-L-leucyl]amino]-2-oxoheptanamide as a white solid; MS: m/e 916.6 [M+H];

3(S)-[[N-[N-[N-[N-[N-(3-carboxypropionyl)-L-α-aspartyl]-D-cyclohexylglycyl]-2-methyl-L- phenylalanyl]-3-methyl-L-valyl]-L-leucyl]amino]-2-oxoheptanamide as a white solid; MS: m/e 900.6 [M+H];

3(S)-[[N-[N-[N-[N-[N-(3-carboxypropionyl)-L-α-aspartyl]-D-phenylglycyl]-2-methyl-L-phenylalanyl]-3-methyl-L-valyl]-L-leucyl]amino]-2-oxoheptanamide as a white solid; MS: m/e 894.5 [M+H];

3(S)-[[N-[N-[N-[N-[N-(3-carboxypropionyl)-L-α-aspartyl]-O-benzyl-D-tyrosyl]-2-methyl-L-phenylalanyl]-3-methyl-L-valyl]-L-leucyl]amino]-2-oxoheptanamide as a white solid; MS: m/e 1014.6 [M+H];

3(S)-[[N-[N-[N-[N2-[N-(3-carboxypropionyl)-L-α-aspartyl]-N6-formyl-L-lysyl]-2-methyl-L-phenylalanyl]-3-methyl-L-valyl]-L-leucyl]amino]-2-oxoheptanamide as a white solid; MS: m/e 917.6 [M+H];

3(S)-[[N-[N-[N-[N-[N-(3-carboxypropionyl)-L-α-aspartyl]-4-nitro-D-phenylalanyl]-2-methyl-L-phenylalanyl]-3-methyl-L-valyl]-L-leucyl]amino]-2-oxoheptanamide as a white solid; MS: m/e 953.6 [M+H];

3(S)-[[N-[N-[N-[N-[N-(3-carboxypropionyl)-L-α-aspartyl]-O-benzyl-D-seryl]-2-methyl-L-phenylalanyl]-3-methyl-L-valyl]-L-leucyl]amino]-2-oxoheptanamide as a white solid; MS: m/e 938.6 [M+H];

3(S)-[[N-[N-[N-[N-[N-(3-carboxypropionyl)-L-α-aspartyl]-D-valyl]-2-methyl-L-phenyl-alanyl]-3-methyl-L-valyl]-L-leucyl]amino]-2-oxoheptanamide as a white solid; MS: m/e 860.6 [M+H];

3(S)-[[N-[N-[N-[N-[N-(3-carboxypropionyl)-L-α-aspartyl]glycyl]-2-methyl-L-phenylalanyl]-3-methyl-L-valyl]-L-leucyl]amino]-2-oxoheptanamide as a white solid; MS: m/e 818.5 [M+H];

3(S)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-2-oxoheptanamide as a white solid; MS: m/e 890.6 [M+H];

3(S)-[[N-[N-[N-[N-[N-(3-carboxypropionyl)-3-cyclohexyl-L-alanyl]-L-α-glutamyl]-2-methyl-L-phenylalanyl]-3-methyl-L-valyl]-L-leucyl]amino]-2-oxoheptanamide as a white solid; MS: m/e 928.6 [M+H];

3(S)-[[N-[N-[N-[N-[N-(3-carboxypropionyl)-L-cyclohexylglycyl]-L-α-glutamyl]-2-methyl-L-phenylalanyl]-3-methyl-L-valyl]-L-leucyl]amino]-2-oxoheptanamide as a white solid; MS: m/e 914.6 [M+H];

3(S)-[[N-[N-[N-[N-[N-(3-carboxypropionyl)-L-prolyl]-L-α-glutamyl]-2-methyl-L-phenylalanyl]-3-methyl-L-valyl]-L-leucyl]amino]-2-oxoheptanamide as a white solid; MS: m/e 972.6 [M+H];

3(S)-[[N-[N-[N-[N-[N-(3-carboxypropionyl)-L-seryl]-L-α-glutamyl]-2-methyl-L-phenylalanyl]-3-methyl-L-valyl]-L-leucyl]amino]-2-oxoheptanamide as a white solid; MS: m/e 862.6 [M+H];

3(S)-[[N-[N-[N-[N-[O-benzyl-N-(3-carboxypropionyl)-L-tyrosyl]-L-α-glutamyl]-2-methyl-L-phenylalanyl]-3-methyl-L-valyl]-L-leucyl]amino]-2-oxoheptanamide as a white solid; MS: m/e 1028.6 [M+H];

3(S)-[[N-[N-[N-[N-[N2-(3-carboxypropionyl)-N6-nitro-L-arginyl]-L-α-glutamyl]-2-methyl-L-phenylalanyl]-3-methyl-L-valyl]-L-leucyl]amino]-2-oxoheptanamide as a white solid; MS: m/e 976.6 [M+H];

3(S)-[[N-[N-[N-[N-[N-(3-carboxypropionyl)-L-phenylglycyl]-L-α-glutamyl]-2-methyl-L-phenylalanyl]-3-methyl-L-valyl]-L-leucyl]amino]-2-oxoheptanamide as a white solid; MS: m/e 908.5 [M+H];

3(S)-[[N-[N-[N-[N-[N-(3-carboxypropionyl)-L-tyrosyl]-L-α-glutamyl]-2-methyl-L-phenylalanyl]-3-methyl-L-valyl]-L-leucyl]amino]-2-oxoheptanamide as a white solid; MS: m/e 938.6 [M+H];

3(S)-[[N-[N-[N-[N-[N2-(3-carboxypropionyl)-N6-(p-toluenesulphonyl)-L-arginyl]-L-α-glutamyl]-2-methyl-L-phenylalanyl]-3-methyl-L-valyl]-L-leucyl]amino]-2-oxoheptanamide as a white solid; MS: m/e 1085.6 [M+H];

3(S)-[[N-[N-[N-[N-[O-benzyl-N-(3-carboxypropionyl)-L-seryl]-L-α-glutamyl]-2-methyl-L-phenylalanyl]-3-methyl-L-valyl]-L-leucyl]amino]-2-oxoheptanamide as a white solid; MS: m/e 952.7 [M+H];

3(S)-[[N-[N-[N-[N-[N2-(3-carboxypropionyl)-L-glutaminyl]-L-α-glutamyl]-2-methyl-L-phenylalanyl]-3-methyl-L-valyl]-L-leucyl]amino]-2-oxoheptanamide as a white solid; MS: m/e 903.6 [M+H];

3(S)-[[N-[N-[N-[N-[3-(benzyloxymethyl)-N-(3-carboxypropionyl)-L-histidyl]-L-α-glutamyl]-2-methyl-L-phenylalanyl]-3-methyl-L-valyl]-L-leucyl]amino]-2-oxoheptanamide as a white solid; MS: m/e 1032.1 [M+H];

3(S)-[[N-[N-[N-[N-[N-(3-carboxypropionyl)-1-(2,4-dinitrophenyl)-L-histidyl]-L-α-glutamyl]-2-methyl-L-phenylalanyl]-3-methyl-L-valyl]-L-leucyl]amino]-2-oxoheptanamide as a white solid; MS: m/e 1078.5 [M+H];

3(S)-[[N-[N-[N-[N-[N-(3-carboxypropionyl)-S-oxo-L-methionyl]-L-α-glutamyl]-2-methyl-L-phenylalanyl]-3-methyl-L-valyl]-L-leucyl]amino]-2-oxoheptanamide as a white solid; MS: m/e 922.5 [M+H];

3(S)-[[N-[N-[N-[N-[N6-acetyl-N2-(3-carboxypropionyl)-L-lysyl]-L-α-glutamyl]-2-methyl-L-phenylalanyl]-3-methyl-L-valyl]-L-leucyl]amino]-2-oxoheptanamide as a white solid; MS: m/e 945.6 [M+H];

3(S)-[[N-[N-[N-[N-[N-(3-carboxypropionyl)-S,S-dioxo-L-methionyl]-L-α-glutamyl]-2-methyl-L-phenylalanyl]-3-methyl-L-valyl]-L-leucyl]amino]-2-oxoheptanamide as a white solid; MS: m/e 938.6 [M+H];

3(S)-[[N-[N-[N-[N-[N-(3-carboxypropionyl)-L-tryptophyl]-L-α-glutamyl]-2-methyl-L-phenylalanyl]-3-methyl-L-valyl]-L-leucyl]amino]-2-oxoheptanamide as a white solid; MS: m/e 961.5 [M+H];

3(S)-[[N-[N-[N-[[3-(3-carboxypropionyl)-4(S)-oxazolidinyl]carbonyl]-L-α-glutamyl]-2-methyl-L-phenylalanyl]-3-methyl-L-valyl]-L-leucyl]amino]-2-oxoheptanamide as a white solid; MS: m/e 890.1 [M+H];

3(S)-[[N-[N-[N-[N-[N2-(3-carboxypropionyl)-N6-formyl-L-lysyl]-L-α-glutamyl]-2-methyl-L-phenylalanyl]-3-methyl-L-valyl]-L-leucyl]amino]-2-oxoheptanamide as a white solid; MS: m/e 931.6 [M+H];

3(S)-[[N-[N-[N-[N-[N-(3-carboxypropionyl)-D-valyl]-L-α-glutamyl]-2-methyl-L-phenylalanyl]-3-methyl-L-valyl]-L-leucyl]amino]-2-oxoheptanamide as a white solid; MS: m/e 874.6 [M+H];

3(S)-[[N-[N-[N-[N-[N2-(3-carboxypropionyl)-L-glutaminyl]-L-α-glutamyl]-2-methyl-L-phenylalanyl]-

3-methyl-L-valyl]-L-leucyl]amino]-2-oxoheptanamide as a white solid; MS: m/e 903.6 [M+H];

3(S)-[[N-[N-[N-[N-[N-(N,N-dimethylglycyl)-L-seryl]-O-benzyl-D-seryl]-2-methyl-L-phenylalanyl]-3-methyl-L-valyl]-L-leucyl]amino]-2-oxoheptanamide as a white solid; MS: m/e 895.8 [M+H];

3(S)-[[N-[N-[N-[N-[N-(3-acetylpropionyl)-L-seryl]-O-benzyl-D-seryl]-2-methyl-L-phenylalanyl]-3-methyl-L-valyl]-L-leucyl]amino]-2-oxoheptanamide as a white solid; MS: m/e 808.6 [M+H];

3(S)-[[N-[N-[N-[N-[N-[(5-benzotriazolyl)carbonyl]-L-seryl]-O-benzyl-D-seryl]-2-methyl-L-phenylalanyl]-3-methyl-L-valyl]-L-leucyl]amino]-2-oxoheptanamide as a white solid; MS: m/e 955.6 [M+H];

3(S)-[[N-[N-[N-[N-[N-[(9-hydroxy-9-fluorenyl)carbonyl]-L-seryl]-O-benzyl-D-seryl]-2-methyl-L-phenylalanyl]-3-methyl-L-valyl]-L-leucyl]amino]-2-oxoheptanamide as a white solid; MS: m/e 1018.6 [M+H];

3(S)-[[N-[N-[N-[N-[N-[(hexahydro-2,6-dioxo-4(S)-pyrimidinyl)carbonyl]-L-seryl]-O-benzyl-D-seryl]-2-methyl-L-phenylalanyl]-3-methyl-L-valyl]-L-leucyl]amino]-2-oxoheptanamide as a white solid; MS: m/e 950.8 [M+H];

3(S)-[[N-[N-[N-[N-[N-[(2-chloro-3-pyridyl)carbonyl]-L-seryl]-O-benzyl-D-seryl]-2-methyl-L-phenylalanyl]-3-methyl-L-valyl]-L-leucyl]amino]-2-oxoheptanamide as a white solid; MS: m/e 949.5 [M+H];

3(S)-[[N-[N-[N-[N-[N-[2-(dimethylamino)benzoyl]-L-seryl]-O-benzyl-D-seryl]-2-methyl-L-phenylalanyl]-3-methyl-L-valyl]-L-leucyl]amino]-2-oxoheptanamide as a white solid; MS: m/e 957.8 [M+H];

3(S)-[[N-[N-[N-[N-[N-[(3-methoxy-3(RS)-cyclohexyl)carbonyl]-L-seryl]-O-benzyl-D-seryl]-2-methyl-L-phenylaanyl]-3-methyl-L-valyl]-L-leucyl]amino]-2-oxoheptanamide as a white solid; MS: m/e 950.6 [M+H];

3(S)-[[N-[N-[N-[N -[N-[4-(benzyloxyformamido)butyryl]-L-seryl]-O-benzyl-D-seryl]-2-methyl-L-phenylalanyl]-3-methyl-L-valyl]-L-leucyl]amino]-2-oxoheptanamide as a white solid; MS: m/e 1029.8 [M+H];

3(S)-[[N-[N-[N-[N-[N-[2-(ethoxy)acetyl]-L-seryl]-O-benzyl-D-seryl]-2-methyl-L-phenylalanyl]-3-methyl-L-valyl]-L-leucyl]amino]-2-oxoheptanamide as a white solid; MS: m/e 896.8 [M+H];

3(S)-[[N-[N-[N-[N-[N-(N-acetyl-DL-allylglycyl)-L-seryl]-O-benzyl-D-seryl]-2-methyl-L-phenylalanyl]-3-methyl-L-valyl]-L-leucyl]amino]-2-oxoheptanamide as a white solid; MS: m/e 949.6 [M+H];

3(S)-[[N-[N-[N-[N-[N-(N-acetyl-4(S)-hydroxy-L-prolyl)-L-seryl]-O-benzyl-D-seryl]-2-methyl-L-phenylalanyl]-3-methyl-L-valyl]-L-leucyl]amino]-2-oxoheptanamide as a white solid; MS: m/e 965.6 [M+H];

3(S)-[[N-[N-[N-[N-[N-(5-oxo-L-prolyl)-L-seryl]-O-benzyl-D-seryl]-2-methyl-L-phenylalanyl]-3-methyl-L-valyl]-L-leucyl]amino]-2-oxoheptanamide as a white solid; MS: m/e 921.8 [M+H];

(E)-3(S)-[[N-[N-[N-[N-[N-(4-phenyl-3-butenoyl)-L-seryl]-O-benzyl-D-seryl]-2-methyl-L-phenylalanyl]-3-methyl-L-valyl]-L-leucyl]amino]-2-oxoheptanamide as a white solid; MS: m/e 954.8 [M+H];

3(S)-[[N-[N-[N-[N-[N-[4-(methoxycarbonyl)butyryl]-L-seryl]-O-benzyl-D-seryl]-2-methyl-L-phenylalanyl]-3-methyl-L-valyl]-L-leucyl]amino]-2-oxoheptanamide as a white solid; MS: m/e 938.8 [M+H];

3(S)-[[N-[N-[N-[N-[N-[3-(2-thenoyl)propionyl]-L-seryl]-O-benzyl-D-seryl]-2-methyl-L-phenylalanyl]-3-methyl-L-valyl]-L-leucyl]amino]-2-oxoheptanamide as a white solid; MS: m/e 976.6 [M+H];

3(S)-[[N-[N-[N-[N-[N-(4,4,4-trifluoro-3-hydroxy-3-methylbutyryl)-L-seryl]-O-benzyl-D-seryl]-2-methyl-L-phenylalanyl]-3-methyl-L-valyl]-L-leucyl]amino]-2-oxoheptanamide as a white solid; MS: m/e 965.8 [M+H];

3(S)-[[N-[N-[N-[N-[N-[3-(dimethylcarbamoyl)propionyl]-L-seryl]-O-benzyl-D-seryl]-2-methyl-L-phenylalanyl]-3-methyl-L-valyl]-L-leucyl]amino]-2-oxoheptanamide as a white solid; MS: m/e 937.8 [M+H];

3(S)-[[N-[N-[N-[N-[N-[((−)-camphanyl)carbonyl]-L-seryl]-O-benzyl-L-α-glutamyl]-2-methyl-L-phenylalanyl]-3-methyl-L-valyl]-L-leucyl]amino]-2-oxoheptanamide as a white solid; MS: m/e 990.6 [M+H];

3(S)-[[N-[N-[N-[N-[N-[(4-tert-butylcyclohexyl)carbonyl]-L-α-aspartyl]-L-α-glutamyl]-2-methyl-L-phenylalanyl]-3-methyl-L-valyl]-L-leucyl]amino]-2-oxoheptanamide as a white solid; MS: m/e 956.8 [M+H];

3(S)-[[N-[N-[N-[N-[N-(3-pentenoyl)-L-α-aspartyl]-L-α-glutamyl]-2-methyl-L-phenylalanyl]-3-methyl-L-valyl]-L-leucyl]amino]-2-oxoheptanamide as a white solid; MS: m/e 873 [M+H];

3(S)-[[N-[N-[N-[N-[N-(4-benzoylbutyryl)-L-α-aspartyl]-L-α-glutamyl]-2-methyl-L-phenylalanyl]-3-methyl-L-valyl]-L-leucyl]amino]-2-oxoheptanamide as a white solid; MS: m/e 964.8 [M+H];

3(S)-[[N-[N-[N-[N-[N-[3-(4-methylbenzoyl)propionyl]-L-α-aspartyl]-L-α-glutamyl]-2-methyl-L-phenylalanyl]-3-methyl-L-valyl]-L-leucyl]amino]-2-oxoheptanamide as a white solid; MS: m/e 964.8 [M+H];

3(S)-[[N-[N-[N-[N-[N-(cyclopropylcarbonyl)-L-α-aspartyl]-L-α-glutamyl]-2-methyl-L-phenylalanyl]-3-methyl-L-valyl]-L-leucyl]amino]-2-oxoheptanamide as a white solid; MS: m/e 858.8 [M+H];

3(S)-[[N-[N-[N-[N-[N-[2-[2-(2-methoxyethoxy)ethoxy]acetyl]-L-α-aspartyl]-L-α-glutamyl]-2-methyl-L-phenylalanyl]-3-methyl-L-valyl]-L-leucyl]amino]-2-oxoheptanamide as a white solid; MS: m/e 950.6 [M+H];

3(S)-[[N-[N-[N-[N-[N-[2-(diethoxyphosphinyl)acetyl]-L-α-aspartyl]-L-α-glutamyl]-2-methyl-L-phenylalanyl]-3-methyl-L-valyl]-L-leucyl]amino]-2-oxoheptanamide as a white solid; MS: m/e 968.6 [M+H];

3(S)-[[N-[N-[N-[N-[N-[(1-acetyl-4-piperidinyl)carbonyl]-L-α-aspartyl]-L-α-glutamyl]-2-methyl-L-phenylalanyl]-3-methyl-L-valyl]-L-leucyl]amino]-2-oxoheptanamide as a white solid; MS: m/e 943.8 [M+H];

3(S)-[[N-[N-[N-[N-[N-[(1-adamantyl)carbonyl]-L-α-aspartyl]-L-α-glutamyl]-2-methyl-L-phenylalanyl]-3-methyl-L-valyl]-L-leucyl]amino]-2-oxoheptanamide as a white solid; MS: m/e 953 [M+H];

3(S)-[[N-[N-[N-[N-[N-[3-(2-methyl-4-nitro-1-imidazolyl)propionyl]-L-α-aspartyl]-L-α-glutamyl]-2-methyl-L-phenylalanyl]-3-methyl-L-valyl]-L-leucyl]

amino]-2-oxoheptanamide as a white solid; MS: m/e 971.8 [M+H];

3(S)-[[N-[N-[N-[N-[N-(4-hexynoyl)-L-α-aspartyl]-L-α-glutamyl]-2-methyl-L-phenylalanyl]-3-methyl-L-valyl]-L-leucyl]amino]-2-oxoheptanamide as a white solid; MS: m/e 884.6 [M+H];

3(S)-[[N-[N-[N-[N-[N-[(2,2-dichloro-1-methyl-1-cyclopropyl)carbonyl]-L-α-aspartyl]-L-α-glutamyl]-2-methyl-L-phenylalanyl]-3-methyl-L-valyl]-L-leucyl]amino]-2-oxoheptanamide as a white solid; MS: m/e 940.8 [M+H];

3(S)-[[N-[N-[N-[N-[N-[2-(4-methylphenoxy)acetyl]-L-α-aspartyl]-L-α-glutamyl]-2-methyl-L-phenylalanyl]-3-methyl-L-valyl]-L-leucyl]amino]-2-oxoheptanamide as a white solid; MS: m/e 938.8 [M+H];

3(S)-[[N-[N-[N-[N-[N-[2-(3-acetyl-2,2-dimethyl-1-cyclobutyl)acetyl]-L-α-aspartyl]-L-α-glutamyl]-2-methyl-L-phenylaanyl]-3-methyl-L-valyl]-L-leucyl]amino]-2-oxoheptanamide as a white solid; MS: m/e 956.8 [M+H];

3(S)-[[N-[N-[N-[N-[N-[(6-oxo-6H-pyran-3-yl)carbonyl]-L-α-aspartyl]-L-α-glutamyl]-2-methyl-L-phenylalanyl]-3-methyl-L-valyl]-L-leucyl]amino]-2-oxoheptanamide as a white solid; MS: m/e 912.8 [M+H];

3(S)-[[N-[N-[N-[N-[N-[(4,5-dihydro-6,6-dimethyl-4-oxo-6H-pyran-2-yl)carbonyl]-L-α-aspartyl]-L-α-glutamyl]-2-methyl-L-phenylalanyl]-3-methyl-L-valyl]-L-leucyl]amino]-2-oxoheptanamide as a white solid; MS: m/e 942.5 [M+H];

3(S)-[[N-[N-[N-[N-[N-[2-(methanesulphonyl)acetyl]-L-α-aspartyl]-L-α-glutamyl]-2-methyl-L-phenylalanyl]-3-methyl-L-valyl]-L-leucyl]amino]-2-oxoheptanamide as a white solid; MS: m/e 910.4 [M+H];

3(S)-[[N-[N-[N-[N-[N-(4,4,4-trifluoro-3(RS)-methylbutyryl)-L-α-aspartyl]-L-α-glutamyl]-2-methyl-L-phenylalanyl]-3-methyl-L-valyl]-L-leucyl]amino]-2-oxoheptanamide as a white solid; MS: m/e 928.6 [M+H];

3(S)-[[N-[N-[N-[N-[N-[(bicyclo[2.2.1]-5-heptenyl)carbonyl]-L-α-aspartyl]-L-α-glutamyl]-2-methyl-L-phenylalanyl]-3-methyl-L-valyl]-L-leucyl]amino]-2-oxoheptanamide as a white solid; MS: m/e 910.4 [M+H];

3(S)-[[N-[N-[N-[N-[N-[2-(2-naphthyl)acetyl]-L-α-aspartyl]-L-α-glutamyl]-2-methyl-L-phenylalanyl]-3-methyl-L-valyl]-L-leucyl]amino]-2-oxoheptanamide as a white solid; MS: m/e 958.6 [M+H];

3(S)-[[N-[N-[N-[N-[N-[(2,6-dioxo-4-pyrimidinyl)carbonyl]-L-α-aspartyl]-L-α-glutamyl]-2-methyl-L-phenylalanyl]-3-methyl-L-valyl]-L-leucyl]amino]-2-oxoheptanamide as a white solid; MS: m/e 928.6 [M+H];

3(S)-[[N-[N-[N-[N-[N-(N-benzoyl-β-alanyl)-L-α-aspartyl]-L-α-glutamyl]-2-methyl-L-phenylalanyl]-3-methyl-L-valyl]-L-leucyl]amino]-2-oxoheptanamide as a white solid; MS: m/e 965.8 [M+H];

3(S)-[[N-[N-[N-[N-[N-[(2,4-dioxo-5-pyrimidinyl)carbonyl]-L-α-aspartyl]-L-α-glutamyl]-2-methyl-L-phenylalanyl]-3-methyl-L-valyl]-L-leucyl]amino]-2-oxoheptanamide as a white solid; MS: m/e 928.8 [M+H];

3(S)-[[N-[N-[N-[N-[N-[4-(acetamido)butyryl]-L-α-aspartyl]-L-α-glutamyl]-2-methyl-L-phenylalanyl]-3-methyl-L-valyl]-L-leucyl]amino]-2-oxoheptanamide as a white solid; MS: m/e 917.6 [M+H];

3(S)-[[N-[N-[N-[N-[N-[4-(phenylcarbamoyl)butyryl]-L-α-aspartyl]-L-α-glutamyl]-2-methyl-L-phenylalanyl]-3-methyl-L-valyl]-L-leucyl]amino]-2-oxoheptanamide as a white solid; MS: m/e 979.8 [M+H];

3(S)-[[N-[N-[N-[N-[N-[2-[(4,6-dimethyl-2-pyrimidinyl)thio]acetyl]-L-α-aspartyl]-L-α-glutamyl]-2-methyl-L-phenylalanyl]-3-methyl-L-valyl]-L-leucyl]amino]-2-oxoheptanamide as a white solid; MS: m/e 970.5 [M+H];

3(S)-[[N-[N-[N-[N-[N-(4-nitrobenzoyl)-β-alanyl]-L-α-aspartyl]-L-α-glutamyl]-2-methyl-L-phenylalanyl]-3-methyl-L-valyl]-L-leucyl]amino]-2-oxoheptanamide as a white solid; MS: m/e 1010.6 [M+H];

3(S)-[[N-[N-[N-[N-[N-[2(S)-[(phenylcarbamoyl)oxy]propionyl]-L-α-aspartyl]-L-α-glutamyl]-2-methyl-L-phenylalanyl]-3-methyl-L-valyl]-L-leucyl]amino]-2-oxoheptanamide as a white solid; MS: m/e 981.6 [M+H];

3(S)-[[N-[N-[N-[N-[N-(3-methyl-2-thenoyl)-L-α-aspartyl]-L-α-glutamyl]-2-methyl-L-phenylalanyl]-3-methyl-L-valyl]-L-leucyl]amino]-2-oxoheptanamide as a white solid; MS: m/e 914.6 [M+H];

3(S)-[[N-[N-[N-[N-[N-[(1-oxido-2-pyridyl)carbonyl]-L-α-aspartyl]-L-α-glutamyl]-2-methyl-L-phenylalanyl]-3-methyl-L-valyl]-L-leucyl]amino]-2-oxoheptanamide as a white solid; MS: m/e 911.6 [M+H];

3(S)-[[N-[N-[N-[N-[N-[(1-phenyl-1-cyclopropyl)carbonyl]-L-α-aspartyl]-L-α-glutamyl]-2-methyl-L-phenylalanyl]-3-methyl-L-valyl]-L-leucyl]amino]-2-oxoheptanamide as a white solid; MS: m/e 934.6 [M+H];

3(S)-[[N-[N-[N-[N-[N-(2-cyclohexylacetyl)-L-α-aspartyl]-L-α-glutamyl]-2-methyl-L-phenylalanyl]-3-methyl-L-valyl]-L-leucyl]amino]-2-oxoheptanamide as a white solid; MS: m/e 914.8 [M+H];

3(S)-[[N-[N-[N-[N-[N-(tetrahydro-3-furoyl)-L-α-aspartyl]-L-α-glutamyl]-2-methyl-L-phenylalanyl]-3-methyl-L-valyl]-L-leucyl]amino]-2-oxoheptanamide as a white solid; MS: m/e 888.6 [M+H];

3(S)-[[N-[N-[N-[N-[N-[2(RS)-(4-nitrophenyl)propionyl]-L-α-aspartyl]-L-α-glutamyl]-2-methyl-L-phenylalanyl]-3-methyl-L-valyl]-L-leucyl]amino]-2-oxoheptanamide as a white solid; MS: m/e 967.8 [M+H];

3(S)-[[N-[N-[N-[N-[N-[4-(2-thenoyl)butyryl]-L-α-aspartyl]-L-α-glutamyl]-2-methyl-L-phenylalanyl]-3-methyl-L-valyl]-L-leucyl]amino]-2-oxoheptanamide as a white solid; MS: m/e 970.6 [M+H];

3(S)-[[N-[N-[N-[N-[N-[[(2-(ethylthio)-3-pyridyl]carbonyl]-L-α-aspartyl]-L-α-glutamyl]-2-methyl-L-phenylalanyl]-3-methyl-L-valyl]-L-leucyl]amino]-2-oxoheptanamide as a white solid; MS: m/e 955.6 [M+H];

3(S)-[[N-[N-[N-[N-[N-(methylcarbonyl)-L-α-aspartyl]-L-α-glutamyl]-2-methyl-L-phenylalanyl]-3-methyl-L-valyl]-L-leucyl]amino]-2-oxoheptanamide as a white solid; MS: m/e 932.6 [M+H]; and 3(S)-[[N-[N-[N-[N-[N-(benzyloxycarbonyl)-L-α-aspartyl]-L-α-glutamyl]-2-methyl-L-phenylalanyl]-3-methyl-L-valyl]-L-leucyl]amino]-2-oxoheptanamide as a white solid; MS: m/e 924.2 [M+H].

What is claimed is:

1. A compound of the general formula I

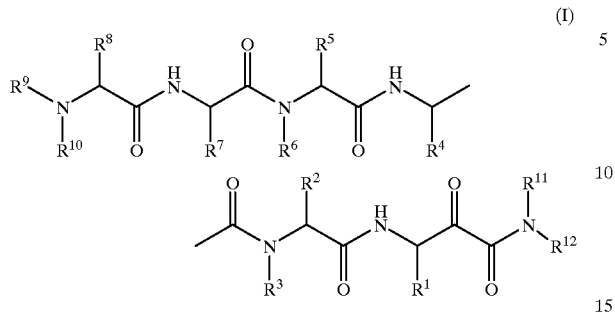

wherein $R^1$ represents lower alkyl, halo-lower alkyl, cyano-lower alkyl, lower alkylthio-lower alkyl, aryl-lower alkylthio-lower alkyl, aryl-lower alkyl, heteroaryl-lower alkyl, lower alkenyl, or lower alkynyl;

$R^2$ represents lower alkyl, hydroxy-lower alkyl, carboxy-lower alkyl, aryl-lower alkyl, aminocarbonyl-lower alkyl, lower cycloalkyl-lower alkyl, aryl-lower alkoxy-aryl-lower alkyl, heteroaryl-lower alkyl, or dihalo aryl lower alkoxy aryl-lower alkyl;

$R^3$ represents hydrogen or lower alkyl; or $R^2$ and $R^3$ together form a cyclic bridge selected from the group consisting of —CH$_2$—CH$_2$—, —CH$_2$—CH$_2$—CH$_2$—, —CHOH—CH$_2$—, —CH$_2$—CHOH—, —CH$_2$—CH$_2$—CHOH—, —CH$_2$—CHOH—CH$_2$—, and —CHOH—CH$_2$—CH$_2$—;

$R^4$ represents lower alkyl, hydroxy-lower alkyl, lower cycloalkyl-lower alkyl, carboxy-lower alkyl, aryl-lower alkyl, aryl-lower alkoxy-aryl-lower alkyl, aryl-lower alkoxy-lower alkyl, aryl-lower alkoxycarbonyl-lower alkyl, lower alkylthio-lower alkyl, cyano-lower alkylthio-lower alkyl, aryl-lower alkylthio-lower alkyl, lower alkenyl, aryl, heteroaryl-lower alkyl, arylsulphonyl-guanidino-lower alkyl, acetamidothio-lower alkyl, lower alkylcarbonylamino-lower alkyl, formamido-lower alkyl, or lower cycloalkyl;

$R^5$ represents lower alkyl, hydroxy-lower alkyl, lower alkylthio-lower alkyl, aryl-lower alkyl, aryl-lower alkylthio-lower alkyl, cyano-lower alkylthio-lower alkyl, lower cycloalkyl, lower cycloalkyl-lower alkyl, aryl-lower alkoxycarbonyl-lower alkyl, aryl-lower alkoxy-aryl-lower alkyl, aryl, arylsulphonyl-guanidino-lower alkyl, aryl-lower alkoxy-lower alkyl, heteroaryl-lower alkyl, or formamido-lower alkyl;

$R^6$ represents hydrogen or lower alkyl;

$R^7$ represents hydrogen, lower alkyl, carboxy-lower alkyl, hydroxy-lower alkyl, aryl-lower alkyl, lower cycloalkyl-lower alkyl, lower cycloalkyl, aryl, heteroaryl-lower alkyl, nitroguanidino-lower alkyl, aryl-lower alkoxy-lower alkyl, aryl-lower alkylthio-lower alkyl, aryl-lower alkoxycarbonyl-lower alkyl, arylsulphonylguanidino-lower alkyl, acetamidothio-lower alkyl, lower alkylsulphonyl-lower alkyl, heteroaryl-lower alkyl, aryl-lower alkoxy-aryl-lower alkyl, aryl-lower alkoxy-heteroaryl-lower alkyl, lower alkylcarbonyloxy-lower alkyl, lower alkylcarbonylamino-lower alkyl, aryl-lower alkyl-heteroaryl-lower alkyl, lower alkenyloxycarbonyl-lower alkyl, lower alkylthio-lower alkyl, formamido-lower alkyl, or nitro substituted aryl-lower alkyl;

$R^8$ represents lower alkyl, lower cycloalkyl, lower cycloalkyl-lower alkyl, carboxy-lower alkyl, hydroxy-lower alkyl, hydroxy substituted aryl-lower alkyl, aryl-lower alkyl, mercapto-lower alkyl, lower alkylsulphonyl-lower alkyl, aryl-lower alkoxy-lower alkyl, aryl-heteroaryl-lower alkyl, aryl-lower alkoxy-aryl-lower alkyl, nitroguanidino-lower alkyl, aryl, acetamidothio-lower alkyl, aryl-sulphonylguanidino-lower alkyl, aminocarbonyl-lower alkyl, aryl-lower alkoxy-lower alkyl-heteroaryl-lower alkyl, lower alkylsulphinyl-lower alkyl, lower alkylaminocarbonyl-lower alkyl, heteroaryl-lower alkyl, lower alkylthio-lower alkyl or formamido-lower alkyl; and $R^9$ represents hydrogen or lower alkyl; or $R^8$ and $R^9$ together form a cyclic bridge selected from the group consisting of —CH$_2$—CH$_2$—CH$_2$—, —CH$_2$—S—CH$_2$—, —CH$_2$—CH$_2$—S—, and —S—CH$_2$—CH$_2$—;

$R^{10}$ represents lower alkylcarbonyl, carboxy-lower alkylcarbonyl, arylcarbonyl, lower alkoxycarbonyl, aryl-lower alkoxycarbonyl, aryl-lower alkylcarbonyl, heteroaryl-lower alkylcarbonyl, arylamino-carbonyl-lower alkylcarbonyl, heteroarylthio-lower alkylcarbonyl, heteroarylcarbonyl, hydroxyfluorenylcarbonyl, heteroarylcarbonyl-lower alkylcarbonyl, lower alkoxy-lower alkylcarbonyl, arylcarbonyl-lower alkylcarbonyl, lower alkoxy-lower alkoxy-lower-alkoxy-lower alkylcarbonyl, arylcarbonyl-amino-lower alkylcarbonyl, heterocyclylcarbonyl, lower alkyl-carbonyloxy-lower alkylcarbonyl, aryloxy-lower alkylcarbonyl, lower alkynylcarbonyl, lower cyclo alkylcarbonyl, di(lower alkyl)amino-lower alkylcarbonyl, aryl-lower alkoxycarbonylamino-lower alkylcarbonyl, lower alkoxy-lower alkylcarbonyl, lower alkylcarbonylamino-lower alkenylcarbonyl, heterocyclyl-lower alkylcarbonyl, lower alkylthio-lower alkylcarbonyl, lower alkoxycarbonyl-lower alkylcarbonyl, aryl-lower alkenylcarbonyl, lower cycloalkenylcarbonyl, di(lower alkyl)aminocarbonyl-lower alkylcarbonyl, halo-lower alkylcarbonyl, lower alkenylcarbonyl, lower alkylcarbonylamino-lower alkylcarbonyl, lower cycloalkyl-lower alkylcarbonyl, lower alkylsulphonyl, arylsulphonyl arylaminocarbonyloxy-lower alkylcarbonyl, lower alkylsulphonyl-lower alkylcarbonyl, lower alkylcarbonyl-lower alkylcarbonyl, hydroxy-halo-lower alkylcarbonyl, di(lower alkoxy)phosphinyl-lower alkylcarbonyl, mono or di (lower alkylamino) lower alkyl carbonyl, mono or di (lower alkyl) amino substituted arylcarbonyl, lower alkoxy lower cycloalkylcarbonyl, lower alkyl substituted arylcarbonyl lower alkylcarbonyl, cyclo lower alkylcarbonyl, aryl substituted cyclo lower alkyl carbonyl, or nitro substituted aryl-lower alkylcarbonyl; and $R^{11}$ and $R^{12}$ each individually represent hydrogen, lower alkyl, aryl, heteroaryl, aryl-lower alkyl, diaryl-lower alkyl, lower cycloalkyl-lower alkyl, lower alkylaminocarbonyl-lower alkyl, lower alkylthio-lower alkyl, lower alkoxy, hydroxy, lower alkoxy substituted aryl lower alkyl, nitro substituted aryl lower alkyl, hydroxy substituted aryl lower alkyl or hydroxylower alkyl substituted aryl lower alkyl or heteroaryl-lower alkyl;

and salts thereof.

2. The compound of claim 1 wherein $R^3$=H; $R^6$=H; $R^9$=H; and $R^{11}$=H.

3. The compound of claim 1, which is

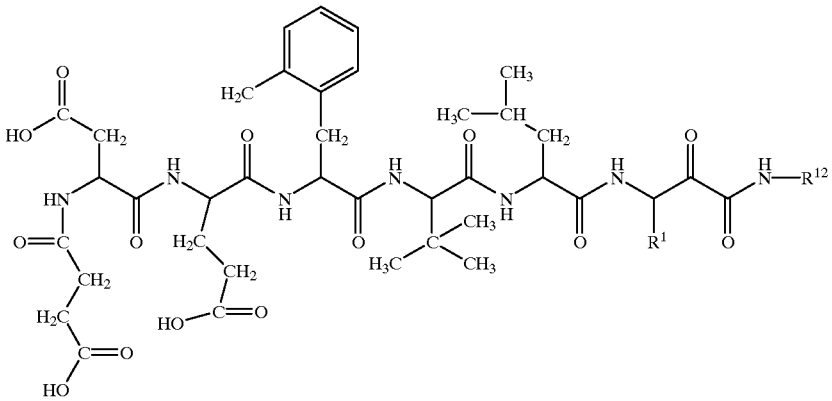

(XXIX)

wherein R¹ is selected from the group consisting of lower alkyl and halo-lower alkyl and R¹² is selected from the group consisting of hydrogen, lower alkyl, aryl-lower alkyl, diaryl-lower alkyl, lower cycloalkyl-lower alkyl, lower alkylaminocarbonyl-lower alkyl, lower alkylthio-lower alkyl, aryl-lower alkyl-lower alkoxy, aryl-lower alkyl-nitro, aryl-lower alkyl-hydroxy-lower alkyl, aryl-hydroxy-lower alkyl, and a five or six member heteroaryl ring-lower alkyl, wherein the five or six member heteroaryl ring contains one or two heteroatoms independently selected from the group consisting of N, O, and S.

4. The compound of claim 3 wherein R¹=trifluoroethyl.

5. The compound of claim 4 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]l-5,5,5-trifluoro-2-oxovaleramide.

6. The compound of claim 4 wherein R¹² is selected from the group consisting of lower alkyl, phenyl, phenyl substituted with one or two substituents independently selected from the group consisting of lower alkyl and lower alkoxy, lower alkyl-naphthyl, nitro-benzyl, phenyl-lower alkyl-hydroxy, hydroxybenzyl, diphenyl-lower alkyl, lower alkylaminocarbonyl, lower alkylthio, lower alkyl-lower cycloalkyl, and lower alkyl-thienyl.

7. The compound of claim 6 wherein R¹² is lower alkyl.

8. The compound of claim 7 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-N-methyl-2-oxovaleranilide.

9. The compound of claim 7 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-2-oxo-N-propylvaleramide.

10. The compound of claim 7 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-N-butyl-5,5,5-trifluoro-2-oxovaleramide.

11. The compound of claim 7 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]l-5,5,5-trifluoro-N-hexyl-2-oxovaleramide.

12. The compound of claim 7 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]l-5,5,5-trifluoro-N-isopropyl-2-oxovaleramide.

13. The compound of claim 7 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]l-5,5,5-trifluoro-N-(1-isopropyl-2-methylpropyl)-2-oxovaleramide.

14. The compound of claim 7 which is N-tert-butyl-3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]l-5,5,5-trifluoro-2-oxovaleramide.

15. The compound of claim 6 wherein R¹² is phenyl or phenyl substituted with one or two substituents independently selected from the group consisting of lower alkyl and lower alkoxy.

16. The compound of claim 15 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-2',4'-dimethyl-2-oxovaleranilide.

17. The compound of claim 15 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-4'-methoxy-2'-methyl-2-oxovaleranilide.

18. The compound of claim 15 which is N-benzyl-3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]l-5,5,5-trifluoro-2-oxovaleramide.

19. The compound of claim 15 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]l-5,5,5-trifluoro-N-(α(S)-methylbenzyl)-2-oxovaleramide.

20. The compound of claim 15 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]l-5,5,5-trifluoro-2-oxo-N-(1(S)-phenylpropyl)valeramide.

21. The compound of claim 15 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]1-5,5,5-trifluoro-2-oxo-N-(1(R)-phenylpropyl)valeramide.

22. The compound of claim 15 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]1-5,5,5-trifluoro-2-oxo-N-(1(S)-phenylbutyl)valeramide.

23. The compound of claim 15 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]1-5,5,5-trifluoro-2-oxo-N-(1(R)-phenylbutyl)valeramide.

24. The compound of claim 15 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]1-5,5,5-trifluoro-N-(2-methyl-1(S)-phenylpropyl)-2-oxovaleramide.

25. The compound of claim 15 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]1-5,5,5-trifluoro-N-(3-methoxybenzyl)-2-oxovaleramide.

26. The compound of claim 6 wherein $R^{12}$ is lower alkyl-naphthyl.

27. The compound of claim 26 wherein lower alkyl contains from 1 to 7 carbon atoms.

28. The compound of claim 27 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]1-5,5,5-trifluoro-N-[1(S)-2-naphthyl)ethyl]-2-oxovaleramide.

29. The compound of claim 27 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]1-5,5,5-trifluoro-N-[1(R)-2-naphthyl)ethyl]-2-oxovaleramide.

30. The compound of claim 27 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]1-5,5,5-trifluoro-N-[(2-naphthyl)propyl]-2-oxovaleramide.

31. The compound of claim 6 wherein $R^{12}$ is nitro-benzyl.

32. The compound of claim 31 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]1-5,5,5-trifluoro-N-(4-nitrobenzyl)-2-oxovaleramide.

33. The compound of claim 31 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]1-5,5,5-trifluoro-N-(3-nitrobenzyl)-2-oxovaleramide.

34. The compound of claim 6 wherein $R^{12}$ is phenyl-lower alkyl-hydroxy-lower alkyl.

35. The compound of claim 34 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino-5,5,5-trifluoro-N-[4-(hydroxymethyl)benzyl)]-2-oxovaleramide.

36. The compound of claim 6 wherein $R^{12}$ is hydroxybenzyl.

37. The compound of claim 36 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]1-5,5,5-trifluoro-N-(4-hydroxybenzyl)-2-oxovaleramide.

38. The compound of claim 6 wherein $R^{12}$ is diphenyl-lower alkyl.

39. The compound of claim 38 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]1-5,5,5-trifluoro-2-oxo-N-(diphenylmethyl)valeramide.

40. The compound of claim 6 wherein $R^{12}$ is lower alkylaminocarbonyl.

41. The compound of claim 40 which is N2-[3(RS)-[[N-[N-[N-[N-(3-carboxypropionyl)-L-α-aspartyl]-L-α-glutamyl]-2-methyl-L-phenylalanyl]-3-methyl-L-valyl]-L-leucyl]amino]-5,5,5-trifluoro-2-oxo-valeryl]N1-methylglycinamide.

42. The compound of claim 6 wherein $R^{12}$ is lower alkylthio.

43. The compound of claim 42 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]1-5,5,5-trifluoro-N-[2-(methylthio)ethyl]-2-oxovaleramide.

44. The compound of claim 6 wherein $R^{12}$ is lower alkyl-lower cycloalkyl.

45. The compound of claim 44 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino-N-(1(S)-cyclohexylethyl)]-5,5,5-trifluoro-2-oxovaleramide.

46. The compound of claim 6 wherein $R^{12}$ is lower alkyl-thienyl.

47. The compound of claim 46 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]1-5,5,5-trifluoro-2-oxo-N-(2-thienl)valeramide.

48. The compound of claim 1 wherein $R^1$ is lower alkyl.

49. The compound of claim 48 wherein $R^{12}$ is lower alkyl.

50. The compound of claim 49 which is 3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]1-2-oxo-N-propylheptanamide.

51. The compound of claim 1 wherein $R^{12}$ is lower alkyl-phenyl.

52. The compound of claim 51 wherein $R^1$ is n-butyl.

53. The compound of claim 52 which is 3(S)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]1-2-oxo-N-)1(S)-phenylpropyl)heptanamide.

54. The compound of claim 1, which is (XXX)

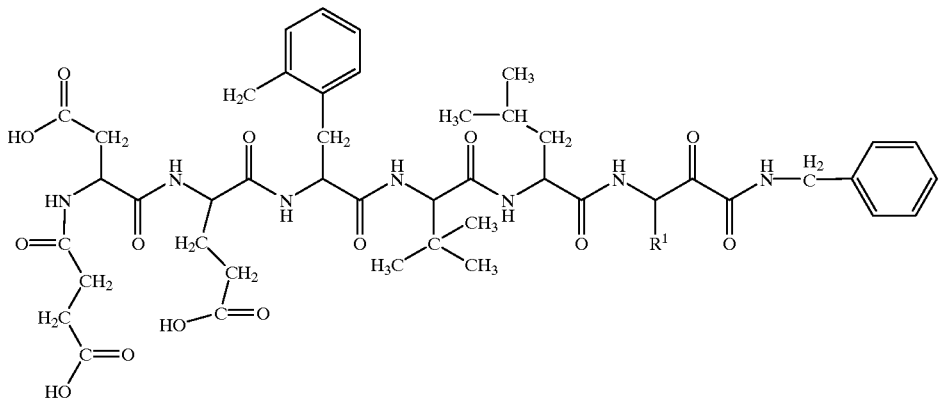

wherein R¹ is selected from the group consisting of lower alkenyl, cyano-lower alkyl, lower alkynyl, aryl-lower alkyl, lower alkylthio-lower alkyl, aryl-lower alkylthio-lower alkyl, and a five or six member heteroaryl ring-lower alkyl, wherein the five or six member heteroaryl ring contains one or two heteroatoms independently selected from the group consisting of N, O, and S.

55. The compound of claim 54 wherein R¹ is selected from the group consisting of lower alkenyl, cyano-lower alkyl, lower alkynyl, phenyl-lower alkyl lower alkylthio-lower alkyl, phenyl-lower alkylthio-lower alkyl, oxazolyl-lower alkyl.

56. The compound of claim 55 wherein R¹ is lower alkenyl.

57. The compound of claim 56 which is N-benzyl-3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-2-oxo-5-heptenamide.

58. The compound of claim 55 wherein R¹ is cyano-lower alkyl.

59. The compound of claim 58 which is N-benzyl-3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-amino]-4-cyano-2-oxobutyramide.

60. The compound of claim 55 wherein R¹ is lower alkynyl.

61. The compound of claim 60 which is N-benzyl-3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-2-oxo-5-heptynamide.

62. The compound of claim 55 wherein R¹ is phenyl-lower alkyl.

63. The compound of claim 62 which is N-benzyl-3(S)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-2-oxo-4-phenylbutyramide.

64. The compound of claim 55 wherein R¹ is lower alkylthio-lower alkyl.

65. The compound of claim 64 which is N-benzyl-4-butylthio-3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-2-oxobutyramide.

66. The compound of claim 55 wherein R¹ is phenyl-lower alkylthio-lower alkyl.

67. The compound of claim 66 which is N-benzyl-4-benzylthio-3(RS)-[[N-[N-[N-[N-[N-(3-carboxypropionyl)-L-α-aspartyl]-O-tert-butyl-L-α-glutamyl]-2-methyl-L-phenylalanyl]-3-methyl-L-valyl]-L-leucyl]amino]-2-oxobutyramide.

68. The compound of claim 55 wherein R¹ is oxazolyl-lower alkyl.

69. The compound of claim 68 which is N-benzyl-3(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-4-(5-oxazolyl)-2-oxobutyramide.

70. The compound of claim 1, which is (XXXI)

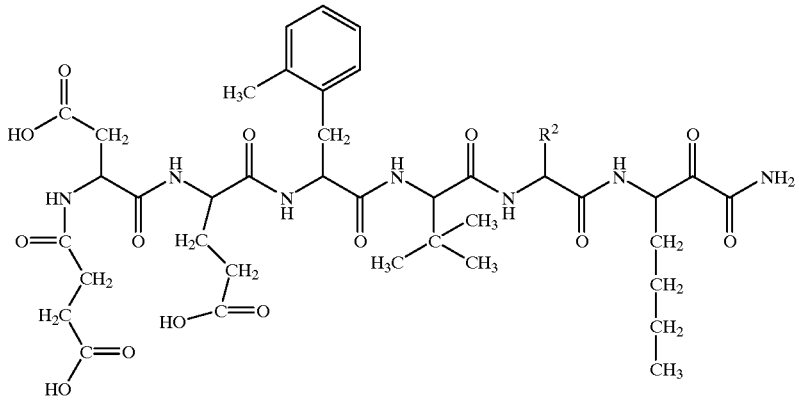

wherein R² is selected from the group consisting of lower alkyl, hydroxy-lower alkyl, aminocarbonyl-lower alkyl, (dihalo substituted aryl-lower alkoxy) substituted aryl lower alkyl, a five or six member heteroaryl ring-lower alkyl, wherein the five or six member heteroaryl ring contains one or two heteroatoms independently selected from the group consisting of N, O, and S, and lower cycloalkyl-lower alkyl.

71. The compound of claim 70 wherein R² is selected from the group consisting of lower alkyl, hydroxy-lower alkyl, aminocarbonyl-lower alkyl, dihalophenyl lower alkoxy phenyl-lower alkyl, thienyl-lower alkyl, and lower cycloalkyl-lower alkyl.

72. The compound of claim 71 wherein R² is lower alkyl.

73. The compound of claim 72 which is 3(S)-[[N-[N-[N-[N-[N-(3-carboxypropionyl)-L-α-aspartyl]-L-α-glutamyl]-2-methyl-L-phenylalanyl]-3-methyl-L-valyl]-L-phenylalanyl]amino]-2-oxoheptanamide.

74. The compound of claim 71 wherein R² is hydroxy-lower alkyl.

75. The compound of claim 74 which is 3(S)-[[N-[N-[N-[N-[N-(3-carboxypropionyl)-L-α-aspartyl]-L-α-glutamyl]-2-methyl-L-phenylalanyl]-3-methyl-L-valyl]-L-seryl]amino]-2-oxoheptanamide.

76. The compound of claim 71 wherein R² is aminocarbonyl-lower alkyl.

77. The compound of claim 76 which is 3(S)-[[N-[N-[N-[N-[N-(3-carboxypropionyl)-L-α-aspartyl]-L-α-glutamyl]-2-methyl-L-phenylalanyl]-3-methyl-L-valyl]-L-glutaminyl]amino]-2-oxoheptanamide.

78. The compound of claim 71 wherein R² is dihalophenyl-lower alkoxy phenyl-lower alkyl.

79. The compound of claim 78 which is 3(S)-[[N-[N-[N-[N-[N-(3-carboxypropionyl)-L-α-aspartyl]-L-α-glutamyl]-2-methyl-L-phenylalanyl]-3-methyl-L-valyl]-O-(2,6-dichlorobenzyl)-L-tyrosyllaminol-2-oxoheptanamide.

80. The compound of claim 71 wherein R² is thienyl-lower alkyl.

81. The compound of claim 80 which is 3(S)-[[N-[N-[N-[N-[N-(3-carboxypropionyl)-L-α-aspartyl]-L-α-glutamyl]-2-methyl-L-phenylalanyl]-3-methyl-L-valyl]-3-(3-thienyl)-L-alanyl]amino]-2-oxoheptanamide.

82. The compound of claim 71 wherein R² is lower cycloalkyl-lower alkyl.

83. The compound of claim 82 which is 3(S)-[[N-[N-[N-[N-[N-(3-carboxypropionyl)-L-α-aspartyl]-L-α-glutamyl]-2-methyl-L-phenylalanyl]-3-methyl-L-valyl]-3-cyclohexyl-L-α-alanyl]amino]-2-oxoheptanamide.

84. The compound of claim 1, which is (XXXII)

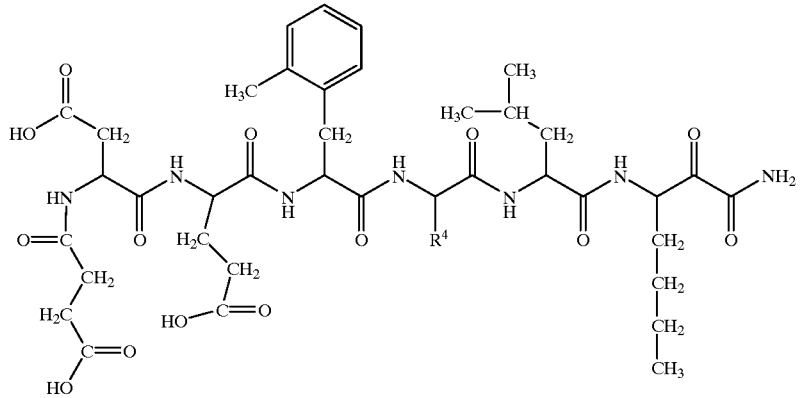

wherein R⁴ is selected from the group consisting of lower cycloalkyl, aryl-lower alkoxycarbonyl-lower alkyl, carboxy-lower alkyl, aryl-lower alkyl, lower cycloalkyl-lower alkyl, hetero aryl lower alkyl wherein said hetero aryl ring contains from four to seven ring members with one of said ring members being a hetero atom selected from the group consisting of N, O and S, aryl-lower alkoxy-aryl-lower alkyl, aryl, aryl-lower alkoxy-lower alkyl, lower alkylcarbonylamino-lower alkyl, lower alkyl-thio-lower alkyl, lower alkenyl, and —(CH$_2$)$_3$—NH—C(NH)—NH-(p-tosyl).

85. The compound of claim 84 wherein R$^4$ is selected from the group consisting of lower cycloalkyl, phenyl-lower alkoxycabonyl-lower alkyl, carboxy-lower alkyl, phenyl-lower alkyl, lower cycloalkyl-lower alkyl, phenyl-lower alkyl-lower alkoxy-phenyl-lower alkyl, phenyl, phenyl-lower alkoxy-lower alkyl, lower alkylcarbonylaminio-lower alkyl, hetero-aryl lower alkyl, lower alkyl-thio-lower alkyl, lower alkenyl, and —(CH$_2$)$_3$—NH—C(NH)—NH-(p-tosyl).

86. The compound of claim 85 which is 3(S)-[[N-[N-[N-[N-[N-(3-carboxypropionyl)-L-α-aspartyl]-L-α-glutamyl]-2-methyl-L-phenylalanyl]N6-(p-toluenesulphonyl)L-arginyl]-L-leucyl]amino]-2-oxoheptanamide.

87. The compound of claim 85 wherein R$^4$ is lower cycloalkyl.

88. The compound of claim 87 which is 3(S)-[[N-[N-[N-[N-[N-(3-carboxypropionyl)-L-α-aspartyl]-L-α-glutamyl]-2-methyl-L-phenylalanyl]-L-cyclohexylglycyl]-L-leucyl]amino]-2-oxoheptanamide.

89. The compound of claim 85 wherein R$^4$ is phenyl-lower alkoxycabonyl-lower alkyl.

90. The compound of claim 89 which is 3(S)-[[N-[N-[N-[N-[N-(3-carboxypropionyl)-L-α-aspartyl]-L-α-glutamyl]-2-methyl-L-phenylalanyl]-O-benzyl-L-α-glutamyl]-L-leucyl]amino]-2-oxoheptanamide.

91. The compound of claim 85 wherein R$^4$ is carboxy-lower alkyl.

92. The compound of claim 91 which is 3(S)-[[N-[N-[N-[N-[N-(3-carboxypropionyl)-L-α-aspartyl]-L-α-glutamyl]-2-methyl-L-phenylalanyl]-L-α-glutamyl]-L-leucyl]amino]-2-oxoheptanamide.

93. The compound of claim 85 wherein R$^4$ is phenyl-lower alkyl.

94. The compound of claim 93 which is 3(S)-[[N-[N-[N-[N-[N-(3-carboxypropionyl)-L-α-aspartyl]-L-α-glutamyl]-2-methyl-L-phenylalanyl]-L-phenylalanyl]-L-leucyl]amino]-2-oxoheptanamide.

95. The compound of claim 85 wherein R$^4$ is lower cycloalkyl-lower alkyl.

96. The compound of claim 95 which is 3(S)-[[N-[N-[N-[N-[N-(3-carboxypropionyl)-L-α-aspartyl]-L-α-glutamyl]-2-methyl-L-phenylalanyl]-3-cyclohexyl-L-alanyl]-L-leucyl]amino]-2-oxoheptanamide.

97. The compound of claim 85 wherein R$^4$ is phenyl-lower alkyl lower alkoxy-phenyl-lower alkyl.

98. The compound of claim 97 which is 3(S)-[[N-[N-[N-[N-[N-(3-carboxypropionyl)-L-α-aspartyl]-L-α-glutamyl]-2-methyl-L-phenylalanyl]-O-benzyl-L-tyrosyl]-L-leucyl]amino]-2-oxoheptanamide.

99. The compound of claim 85 wherein R$^4$ is phenyl.

100. The compound of claim 99 which is 3(S)-[[N-[N-[N-[N-[N-(3-carboxypropionyl)-L-α-aspartyl]-L-α-glutamyl]-2-methyl-L-phenylalanyl]-L-phenylglycyl]-L-leucyl]amino]-2-oxoheptanamide.

101. The compound of claim 85 wherein R$^4$ is phenyl-lower alkoxy-lower alkyl.

102. The compound of claim 101 which is 3(S)-[[N-[N-[N-[N-[N-(3-carboxypropionyl)-L-α-aspartyl]-L-α-glutamyl]-2-methyl-L-phenylalanyl]-O-benzyl-L-threonyl]-L-leucyl]amino]-2-oxoheptanamide.

103. The compound of claim 85 wherein R$^4$ is lower alkylcarbonylaminio-lower alkyl.

104. The compound of claim 103 which is 3(S)-[[N-[N-[N-[N-[N-(3-carboxypropionyl)-L-α-aspartyl]-L-α-glutamyl]-2-methyl-L-phenylalanyl]-N6-acetyl-L-lysyl]-L-leucyl]amino]-2-oxoheptanamide.

105. The compound of claim 85 wherein R$^4$ is hetero aryl-lower alkyl.

106. The compound of claim 105 which is 3(S)-[[N-[N-[N-[N-[N-(3-carboxypropionyl)-L-α-aspartyl]-L-α-glutamyl]-2-methyl-L-phenylalanyl]-3-(3-thienyl)-L-alanyl]-L-leucyl]amino]-2-oxoheptanamide.

107. The compound of claim 85 wherein R$^4$ is lower alkenyl.

108. The compound of claim 107 which is 3(S)-[[N-[N-[N-[N-[N-(3-carboxypropionyl)-L-α-aspartyl]-L-α-glutamyl]-2-methyl-L-phenylalanyl]-L-allylglycyl]-L-leucyl]amino]-2-oxoheptanamide.

109. The compound of claim 1, which is (XXXIII)

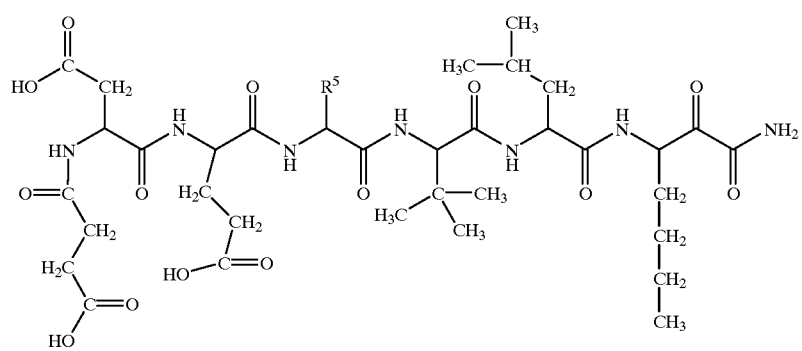

wherein R$^5$ is selected from the group consisting of lower alkyl, hydroxy-lower alkyl, aryl-lower alkyl-thio-lower alkyl, lower cycloalkyl, lower cycloalkyl-lower alkyl, aryl-lower alkoxycarbonyl-lower alkyl, aryl-lower alkoxy-aryl-lower alkyl, aryl, (CH$_2$)$_3$—NH—C(NH)—NH-(p-tosyl), aryl-lower alkoxy-lower alkyl, and a five or six member heteroaryl ring-lower alkyl, wherein the five or six member heteroaryl ring contains one or two heteroatoms independently selected from the group consisting of N, O, and S.

110. The compound of claim 109 wherein R$^5$ is selected from the group consisting of lower alkyl, hydroxy-lower alkyl, phenyl-lower alkyl-thio-lower alkyl, lower cycloalkyl, lower cycloalkyl-lower alkyl, phenyl-lower alkoxycarbonyl-lower alkyl, phenyl-lower alkoxy-phenyl-lower alkyl, phenyl, (CH$_2$)$_3$—NH—C(NH)—NH-(p-tosyl), phenyl-lower alkoxy-lower alkyl, and thienyl-lower alkyl.

111. The compound of claim 110 which is 3(S)-[[N-[N-[N-[N-[N-(3-carboxypropionyl)-L-α-aspartyl]-L-α-glutamyl]-N6-(p-toluenesulphonyl)-L-arginyl]-3-methyl-L-valyl]-L-leucyl]amino]-2-oxoheptanamide.

112. The compound of claim 110 wherein R$^5$ is lower alkyl.

113. The compound of claim 112 which is 3(S)-[[N-[N-[N-[N-[N-(3-carboxypropionyl)-L-α-aspartyl]-L-α-glutamyl]-L-valyl]-3-methyl-L-valyl]-L-leucyl]amino]-2-oxoheptanamide.

114. The compound of claim 110 wherein R$^5$ is hydroxy-lower alkyl.

115. The compound of claim 114 which is 3(S)-[[N-[N-[N-[N-[N-(3-carboxypropionyl)-L-α-aspartyl]-L-α-glutamyl]-L-seryl]-3-methyl-L-valyl]-L-leucyl]amino]-2-oxoheptanamide.

116. The compound of claim 110 wherein R$^5$ is phenyl-lower alkyl-thio-lower alkyl.

117. The compound of claim 116 which is 3(S)-[[N-[N-[N-[N-[N-(3-carboxypropionyl)-L-α-aspartyl]-L-α-glutamyl]-S-benzyl-L-cysteinyl]-3-methyl-L-valyl]-L-leucyl]amino]-2-oxoheptanamide.

118. The compound of claim 110 wherein R$^5$ is lower cycloalkyl.

119. The compound of claim 118 which is 3(S)-[[N-[N-[N-[N-[N-(3-carboxypropionyl)-L-α-aspartyl]-L-α-glutamyl]-L-cyclohexylglycyl]-3-methyl-L-valyl]-L-leucyl]amino]-2-oxoheptanamide.

120. The compound of claim 110 wherein R$^1$ is lower cycloalkyl-lower alkyl.

121. The compound of claim 120 which is 3(S)-[[N-[N-[N-[N-[N-(3-carboxypropionyl)-L-α-aspartyl]-L-α-glutamyl]-3-cyclohexyl-L-alanyl]-3-methyl-L-valyl]-L-leucyl]amino]-2-oxoheptanamide.

122. The compound of claim 110 wherein R$^1$ is phenyl-lower alkoxycarbonyl-lower alkyl.

123. The compound of claim 122 which is 3(S)-[[N-[N-[N-[N-[N-(3-carboxypropionyl)-L-α-aspartyl]-L-α-glutamyl]-O-benzyl-L-α-glutamyl]-3-methyl-L-valyl]-L-leucyl]amino]-2-oxoheptanamide.

124. The compound of claim 110 wherein R$^5$ is phenyl-lower alkoxy-phenyl-lower alkyl.

125. The compound of claim 124 which is 3(S)-[[N-[N-[N-[N-[N-(3-carboxypropionyl)-L-α-aspartyl]-L-α-glutamyl]-O-benzyl-L-tyrosyl]-3-methyl-L-valyl]-L-leucyl]amino]-2-oxoheptanamide.

126. The compound of claim 110 wherein R$^5$ is phenyl.

127. The compound of claim 126 which is 3(S)-[[N-[N-[N-[N-[N-(3-carboxypropionyl)-L-α-aspartyl]-L-α-glutamyl]-L-phenylglycyl]-3-methyl-L-valyl]-L-leucyl]amino]-2-oxoheptanamide.

128. The compound of claim 126 which is 3(S)-[[N-[N-[N-[N-[N-(3-carboxypropionyl)-L-α-aspartyl]-L-α-glutamyl]-D-phenylglycyl]-3-methyl-L-valyl]-L-leucyl]amino]-2-oxoheptanamide.

129. The compound of claim 110 wherein R$^5$ is phenyl-lower alkoxy-lower alkyl.

130. The compound of claim 129 which is 3(S)-[[N-[N-[N-[N-[N-(3-carboxypropionyl)-L-α-aspartyl]-L-α-glutamyl]-O-benzyl-L-threonyl]-3-methyl-L-valyl]-L-leucyl]amino]-2-oxoheptanamide.

131. The compound of claim 110 wherein R$^5$ is thienyl-lower alkyl.

132. The compound of claim 131 which is 3(S)-[[N-[N-[N-[N-[N-(3-carboxypropionyl)-L-α-aspartyl]-L-α-glutamyl]-3-(3-thienyl)-L-alanyl]-3-methyl-L-valyl]-L-leucyl]amino]-2-oxoheptanamide.

133. The compound of claim 1, which is (XXXIV)

wherein R$^7$ is selected from the group consisting of aryl-lower alkoxycarbonyl-lower alkyl, aryl-lower alkoxy-aryl-lower alkyl, nitroguanidino-lower alkyl, aryl-lower alkoxy-a five or six member heteroaryl ring-lower alkyl, wherein the five or six member heteroaryl ring contains one or two heteroatoms independently selected from the group consisting of N, O, and S, lower alkylcarbonylamino-lower alkyl, aryl-lower alkyl-a five or six member heteroaryl ring-lower alkyl, wherein the five or six member heteroaryl ring contains one or two heteroatoms independently selected from the group consisting of N, O, and S, lower alkyl-thio-lower alkyl, a five or six member heteroaryl ring-lower alkyl, wherein the five or six member heteroaryl ring contains one or two heteroatoms independently selected from the group consisting of N, O, and S, lower alkenyloxycarbonyl-lower alkyl, lower cycloalkyl, aryl, formidamino-lower alkyl, aryl-nitro-lower alkyl, aryl-lower alkoxy-lower alkyl, lower alkyl, hydrogen, and carboxy-lower alkyl.

134. The compound of claim 133 wherein $R^7$ is selected from the group consisting of phenyl-lower alkoxycarbonyl-lower alkyl, phenyl-lower alkoxy-phenyl-lower alkyl, nitroguanidino lower alkyl, phenyl-lower alkoxy-imidizolyl-lower alkyl, lower alkylcarbonylamino-lower alkyl, phenyl-lower alkyl-imidazolyl-lower alkyl, lower alkyl-thio-lower alkyl, indolyl-lower alkyl, lower alkenyloxycarbonyl-lower alkyl, lower cycloalkyl, phenyl, formidamino-lower alkyl, nitro substituted phenyl-lower alkyl, phenyl-lower alkoxy-lower alkyl, lower alkyl, hydrogen, and carboxy-lower alkyl.

135. The compound of claim 134 which is 3(S)-[[N-[N-[N-[N-[N-(3-carboxypropionyl)-L-α-aspartyl]-glycyl]-2-methyl-L-phenylalanyl]-3-methyl-L-valyl]-L-leucyl]amino]-2-oxoheptanamide.

136. The compound of claim 134 wherein $R^7$ is phenyl-lower alkoxycarbonyl-lower alkyl.

137. The compound of claim 136 which is 3(S)-[[N-[N-[N-[N-[N-(3-carboxypropionyl)-L-α-aspartyl]-O-benzyl-L-α-glutamyl]-2-methyl-L-phenylalanyl]-3-methyl-L-valyl]-L-leucyl]amino]-2-oxoheptanamide.

138. The compound of claim 134 wherein $R^7$ is phenyl-lower alkoxy-phenyl-lower alkyl.

139. The compound of claim 138 which is 3(S)-[[N-[N-[N-[N-(3-carboxypropionyl)-L-α-aspartyl]-O-benzyl-L-tyrosyl]-2-methyl-L-phenylalanyl]-3-methyl-L-valyl]-L-leucyl]amino]-2-oxoheptanamide.

140. The compound of claim 138 which is 3(S)-[[N-[N-[N-[N-(3-carboxypropionyl)-L-α-aspartyl]-O-benzyl-D-tyrosyl]-2-methyl-L-phenylalanyl]-3-methyl-L-valyl]-L-leucyl]amino]-2-oxoheptanamide.

141. The compound of claim 134 wherein $R^7$ is nitroguanidino-lower alkyl.

142. The compound of claim 141 which is 3(S)-[[N-[N-[N-[N-(3-carboxypropionyl)-L-α-aspartyl]-N6-nitro-arginyl]-2-methyl-L-phenylalanyl]-3-methyl-L-valyl]-L-leucyl]amino]-2-oxoheptanamide.

143. The compound of claim 134 wherein $R^7$ is phenyl-lower alkoxy-imidizolyl-lower alkyl.

144. The compound of claim 143 which is 3(S)-[[N-[N-[N-[N-(3-carboxypropionyl)-L-α-aspartyl]-3-(benzyloxymethyl)-L-histadyl]-2-methyl-L-phenylalanyl]-3-methyl-L-valyl]-L-leucyl]aminol-2-oxoheptanamide.

145. The compound of claim 134 wherein $R^7$ is lower alkylcarbonylamino-lower alkyl.

146. The compound of claim 145 which is 3(S)-[[N-[N-[N-[N-(3-carboxypropionyl)-L-α-aspartyl]-N6-acetyl-L-lysyl]-2-methyl-L-phenylalanyl]-3-methyl-L-valyl]-L-leucyl]amino]-2-oxoheptanamide.

147. The compound of claim 134 wherein $R^7$ is phenyl-lower alkyl-imidazolyl-lower alkyl.

148. The compound of claim 147 which is 3(S)-[[N-[N-[N-[N-(3-carboxypropionyl)-L-α-aspartyl]-1-benzyl-L-histidyl]-2-methyl-L-phenylalanyl]-3-methyl-L-valyl]-L-leucyl]amino]-2-oxoheptanamide.

149. The compound of claim 134 wherein $R^7$ is lower alkyl-thio-lower alkyl.

150. The compound of claim 149 which is 3(S)-[[N-[N-[N-[N-(3-carboxypropionyl)-L-α-aspartyl]-S,S-dioxo-L-methionyl]-2-methyl-L-phenylalanyl]-3-methyl-L-valyl]-L-leucyl]amino]-2-oxoheptanamide.

151. The compound of claim 134 wherein $R^7$ is indolyl-lower alkyl.

152. The compound of claim 151 which is 3(S)-[[N-[N-[N-[N-(3-carboxypropionyl)-L-α-aspartyl]-L-tryptophyl]-2-methyl-L-phenylalanyl]-3-methyl-L-valyl]-L-leucyl]amino]-2-oxoheptanamide.

153. The compound of claim 134 wherein $R^7$ is lower alkenyloxycarbonyl-lower alkyl.

154. The compound of claim 153 which is 3(S)-[[N-[N-[N-[N-(3-carboxypropionyl)-L-α-aspartyl]-O-allyl-L-α-aspartyl]-2-methyl-L-phenylalanyl]-3-methyl-L-valyl]-L-leucyl]amino]-2-oxoheptanamide.

155. The compound of claim 134 wherein $R^7$ is lower cycloalkyl.

156. The compound of claim 155 which is 3(S)-[[N-[N-[N-[N-(3-carboxypropionyl)-L-α-aspartyl]-D-cyclohexylglycyl]-2-methyl-L-phenylalanyl]-3-methyl-L-valyl]-L-leucyl]amino]-2-oxoheptanamide.

157. The compound of claim 134 wherein $R^7$ is phenyl.

158. The compound of claim 157 which is 3(S)-[[N-[N-[N-[N-(3-carboxypropionyl)-L-α-aspartyl]-D-phenylglycyl]-2-methyl-L-phenylalanyl]-3-methyl-L-valyl]-L-leucyl]amino]-2-oxoheptanamide.

159. The compound of claim 134 wherein $R^7$ is formamido-lower alkyl.

160. The compound of claim 159 which is 3(S)-[[N-[N-[N-[N-(3-carboxypropionyl)-L-α-aspartyl]-N6-formyl-L-lysyl]-2-methyl-L-phenylalanyl]-3-methyl-L-valyl]-L-leucyl]amino]-2-oxoheptanamide.

161. The compound of claim 134 wherein $R^7$ is nitro substituted phenyl-lower alkyl.

162. The compound of claim 161 which is 3(S)-[[N-[N-[N-[N-(3-carboxypropionyl)-L-α-aspartyl]-4-nitro-D-phenylalanyl]-2-methyl-L-phenylalanyl]-3-methyl-L-valyl]-L-leucyl]amino]-2-oxoheptanamide.

163. The compound of claim 134 wherein $R^7$ is phenyl-lower alkoxy-lower alkyl.

164. The compound of claim 163 which is 3(S)-[[N-[N-[N-[N-(3-carboxypropionyl)-L-α-aspartyl]-O-benzyl-D-seryl]-2-methyl-L-phenylalanyl]-3-methyl-L-valyl]-L-leucyl]amino]-2-oxoheptanamide.

165. The compound of claim 134 wherein $R^7$ is lower alkyl.

166. The compound of claim 165 which is 3(S)-[[N-[N-[N-[N-(3-carboxypropionyl)-L-α-aspartyl]-D-valyl]-2-methyl-L-phenylalanyl]-3-methyl-L-valyl]-L-leucyl]amino]-2-oxoheptanamide.

167. The compound of claim 134 wherein $R^7$ is carboxy-lower alkyl.

168. The compound of claim 167 which is 3(S)-[[N-[N-[N-[N-(3-carboxypropionyl)-L-α-aspartyl]-L-α-glutamyl]-2-methyl-L-phenylalanyl]-3-methyl-L-valyl]-L-leucyl]amino]-2-oxoheptanamide.

169. The compound of claim 1, which is (XXXV)

wherein R⁸ is selected from the group consisting of lower cycloalkyl-lower alkyl, lower cycloalkyl, hydroxy-lower alkyl, aryl-lower alkoxy-aryl-lower alkyl, nitroguanidino-lower alkyl, aryl, amino-lower alkyl, arylsulfonylguanidino-lower alkyl, carboxy-lower alkyl, aryl-lower alkoxy-lower alkyl, -a five or six member heteroaryl ring-lower alkyl, wherein the five or six member heteroaryl ring contains one or two heteroatoms independently selected from the group consisting of N, O, and S, aryl imidazolyl wherein said aryl is unsubstituted or mono or di nitro or halo substituted, lower alkylsulfinyl-lower alkyl, lower alkylaminocarbonyl-lower alkyl, lower alkylsufonyl-lower alkyl, aryl-lower alkyl, formamido-lower alkyl, lower alkyl, aminocarbonyl-lower alkyl and hydroxy phenyl lower alkyl.

170. The compound of claim 169 wherein R⁸ is selected from the group consisting of lower cycloalkyl-lower alkyl, lower cycloalkyl, hydroxy-lower alkyl, phenyl-lower alkoxy-phenyl-lower alkyl, nitroguanidino-lower alkyl, phenyl, amino-lower alkyl, tosylsufonylguanidino-lower alkyl, carboxy-lower alkyl, phenyl-lower alkoxy-lower alkyl-imidazolyl-lower alkyl, dinitrophenyl imidazolyl-lower alkyl, lower alkylsulfinyl-lower alkyl, lower alkyl-aminocarbonyl-lower alkyl, lower alkylsulfonyl, indolyl-lower alkyl, formamido-lower alkyl, lower alkyl, naminocarbonyl-lower alkyl and hydroxyphenyl lower alkyl.

171. The compound of claim 170 which is 3(S)-[[N-[N-[N-[N-[N-(3-carboxypropionyl)-L-phenylglycyl]-L-α-glutamyl]-2-methyl-L-phenylalanyl]-3-methyl-L-valyl]-L-leucyl]amino]-2-oxoheptanamide.

172. The compound of claim 170 wherein R⁸ is lower cycloalkyl-lower alkyl.

173. The compound of claim 172 which is 3(S)-[[N-[N-[N-[N-[N-(3-carboxypropionyl)-3-cyclohexyl-L-alanyl]-L-α-glutamyl]-2-methyl-L-phenylalanyl]-3-methyl-L-valyl]-L-leucyl]amino]-2-oxoheptanamide.

174. The compound of claim 170 wherein R⁸ is lower cycloalkyl.

175. The compound of claim 174 which is 3(S)-[[N-[N-[N-[N-[N-(3-carboxypropionyl)-L-cyclohexylglycyl]-L-α-glutamyl]-2-methyl-L-phenylalanyl]-3-methyl-L-valyl]-L-leucyl]amino]-2-oxoheptanamide.

176. The compound of claim 170 wherein R⁸ is hydroxy-lower alkyl.

177. The compound of claim 176 which is 3(S)-[[N-[N-[N-[N-[N-(3-carboxypropionyl)-L-seryl]-L-α-glutamyl]-2-methyl-L-phenylalanyl]-3-methyl-L-valyl]-L-leucyl]amino]-2-oxoheptanamide.

178. The compound of claim 170 wherein R⁸ is phenyl-lower alkoxy-phenyl-lower alkyl.

179. The compound of claim 178 which is 3(S)-[[N-[N-[N-[N-[O-benzyl-N-(3-carboxypropionyl)-L-tyrosyl]-L-α-glutamyl]-2-methyl-L-phenylalanyl]-3-methyl-L-valyl]-L-leucyl]amino]-2-oxoheptanamide.

180. The compound of claim 170 wherein R⁸ is nitroguanidino-lower alkyl.

181. The compound of claim 180 which is 3(S)-[[N-[N-[N-[N-[N2-(3-carboxypropionyl)-N6-nitro-L-arginyl]-L-α-glutamyl]-2-methyl-L-phenylalanyl]-3-methyl-L-valyl]-L-leucyl]amino]-2-oxoheptanamide.

182. The compound of claim 170 wherein R⁸ is hydroxyphenyl-lower alkyl.

183. The compound of claim 182 which is 3(S)-[[N-[N-[N-[N-[N-(3-carboxypropionyl)-L-tyrosyl]-L-α-glutamyl]-2-methyl-L-phenylalanyl]-3-methyl-L-valyl]-L-leucyl]amino]-2-oxoheptanamide.

184. The compound of claim 170 wherein R⁸ is tosylsufonylguanidino-lower alkyl.

185. The compound of claim 184 which is 3(S)-[[N-[N-[N-[N-[N2-(3-carboxypropionyl)-N6-(p-toluenesulphonyl-L-arginyl]-L-α-glutamyl]-2-methyl-L-phenylalanyl]-3-methyl-L-valyl]-L-leucyl]amino]-2-oxoheptanamide.

186. The compound of claim 170 wherein R⁸ is phenyl-lower alkoxy-lower alkyl-imidazolyl-lower alkyl.

187. The compound of claim 186 which is 3(S)-[[N-[N-[N-[N-3-benzyloxymethyl-N-(3-carboxypropionyl)-L-histidyl]-L-α-g lutamyl]-2-methyl-L-phenylalanyl]-3-methyl-L-valyl]-L-leucyl]amino]-2-oxoheptanamide.

188. The compound of claim 170 wherein R⁸ is dinitrophenyl imidazolyl-lower alkyl.

189. The compound of claim 188 which is 3(S)-[[N-[N-[N-[N-[N-(3-carboxypropionyl)-1-(2,4-dinitrophenyl)-L-histidyl]-L-α-glutamyl]-2-methyl-L-phenylalanyl]-3-methyl-L-valyl]-L-leucyl]amino]-2-oxoheptanamide.

190. The compound of claim 170 wherein R⁸ is lower alkylsulfinyl-lower alkyl.

191. The compound of claim 190 which is 3(S)-[[N-[N-[N-[N-[N-(3-carboxypropionyl)-S-oxo-L-methionyl]-L-α-glutamyl]-2-methyl-L-phenylalanyl]-3-methyl-L-valyl]-L-leucyl]amino]-2-oxoheptanamide.

192. The compound of claim 170 wherein R⁸ is lower alkyl-aminocarbonyl-lower alkyl.

193. The compound of claim 192 which is 3(S)-[[N-[N-[N-[N-[N6-acetyl-N2-(3-carboxypropionyl)-L-lysyl]-L-α- glutamyl]-2-methyl-L-phenylalanyl]-3-methyl-L-valyl]-L-leucyl]amino]-2-oxoheptanamide.

194. The compound of claim 170 wherein $R^8$ is lower alkylsulfonyl.

195. The compound of claim 194 which is 3(S)-[[N-[N-[N-[N-[N-(3-carboxypropionyl)-S,S-dioxo-L-methionyl]-L-α-glutamyl]-2-methyl-L-phenylalanyl]-3-methyl-L-valyl]-L-leucyl]amino]-2-oxoheptanamide.

196. The compound of claim 170 wherein $R^8$ is indolyl-lower alkyl.

197. The compound of claim 196 which is 3(S)-[[N-[N-[N-[N-[N-(3-carboxypropionyl)-L-tryptophyl]-L-α-glutamyl]-2-methyl-L-phenylalanyl]-3-methyl-L-valyl]-L-leucyl]amino]-2-oxoheptanamide.

198. The compound of claim 170 wherein $R^8$ is formamido-lower alkyl.

199. The compound of claim 198 which is 3(S)-[[N-[N-[N-[N-[N2-(3-carboxypropionyl)-N6-formyl-L-lysyl]-L-α-glutamyl]-2-methyl-L-phenylalanyl]-3-methyl-L-valyl]-L-leucyl]amino]-2-oxoheptanamide.

200. The compound of claim 170 wherein $R^8$ is lower alkyl.

201. The compound of claim 200 which is 3(S)-[[N-[N-[N-[N-[N-(3-carboxypropionyl)-D-valyl]-L-α-glutamyl]-2-methyl-L-phenylalanyl]-3-methyl-L-valyl]-L-leucyl]amino]-2-oxoheptanamide.

202. The compound of claim 170 wherein $R^8$ is aminocarbonyl-lower alkyl.

203. The compound of claim 202 which is 3(S)-[[N-[N-[N-[N-[N2-(3-carboxypropionyl)-L-glutaminyl]-L-α-glutamyl]-2-methyl-L-phenylalanyl]-3-methyl-L-valyl]-L-leucyl]amino]-2-oxoheptanamide.

204. The compound of claim 1, which is alkoxy substituted cycloalkyl carbonyl, aryl-lower alkoxycarbonylamino-lower alkylcarbonyl, lower alkoxy-lower alkylcarbonyl, lower alkylcarbonylamino-lower alkenylcarbonyl, aryl-lower alkenylcarbonyl, lower alkoxycarbonyl-lower alkylcarbonyl, lower alkyl heteroaryl carbonyl wherein said heteroaryl is a five or six member heteroaryl ring containing one or two heteroatoms independently selected from the group consisting of N, O, and S, heteroaryl carbonyl-lower alkylcarbonyl, hydroxy-halo-lower alkylcarbonyl, di(lower alkyl) aminocarbonyl-lower alkylcarbonyl, lower alkylcarbonyl, lower cycloalkyl-lower alkylcarbonyl, lower alkenylcarbonyl, arylcarbonyl-lower alkylcarbonyl, aryl-lower alkylcarbonyl-lower alkylcarbonyl, lower alkoxy-lower alkoxy-lower alkoxy-lower alkylcarbonyl, di(lower alkoxy) phosphinyl-lower alkylcarbonyl, cycloloweralkylcarbonyl, a five or six member heteroaryl ring-lower alkyl or lower alkenyl carbonyl, wherein the five or six member heteroaryl ring contains one or two heteroatoms independently selected from the group consisting of N, O, and S and can be unsubstituted or hydroxy substituted, lower alkynylcarbonyl, (di(halo-lower alkyl-lower cycloalkyl)carbonyl, lower alkylthio-lower alkylcarbonyl, unsubstituted or nitro substituted arylcarbonyl-amino-lower alkylcarbonyl, lower alkylcarbonylamino-lower alkylcarbonyl, arylaminocarbonyl-lower alkylcarbonyl, a five or six member heteroaryl ring-thio-lower alkylcarbonyl, wherein the five or six member heteroaryl ring contains one or two heteroatoms independently selected from (XXXVI)

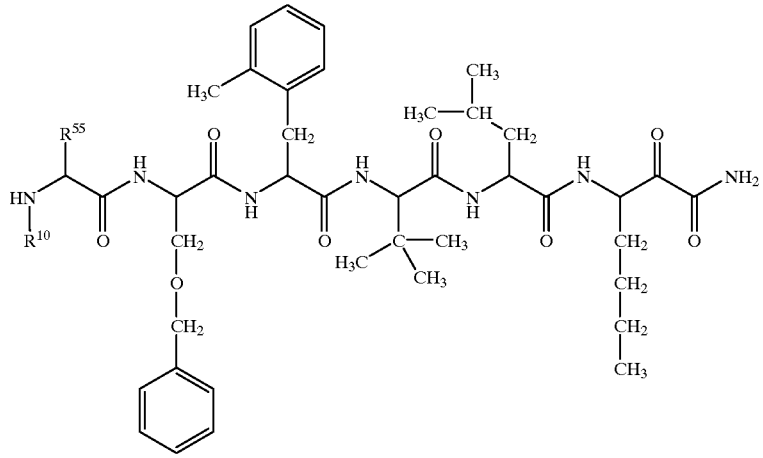

wherein $R^{10}$ is selected from the group consisting of lower alkylamino-lower alkylcarbonyl, lower alkylcarbonyl-lower alkylcarbonyl, heterocyclylcarbonyl wherein the heterocylic ring contains from four to twelve ring atoms with one of said ring atoms being a heteroatom selected from the group consisting of O, S and N, a five or six member heteroaryl ring-carbonyl, wherein the five or six member heteroaryl ring contains one or two heteroatoms independently selected from the group consisting of N, O, and S, hydroxyfluorenylcarbonyl, heterocycylcarbonyl, di(lower alkyl)amino substituted aryl carbonyl, lower the group consisting of N, O, and S, cycloloweralkyl carbonyl wherein the cycloloweralkyl group is unsubstituted or substituted with one to three substituents selected from the group consisting of lower alkyl and lower alkyl carbonyl, aryl lower cycloalkyl-carbonyl, nitroaryl-lower alkylcarbonyl, lower alkylcarbonyl, and lower alkyl substituted phenoxy-lower alkylcarbonyl; and $R^{55}$ is $CH_2COOH$ or $CH_2OH$.

205. The compound of claim 204 wherein $R^{10}$ is selected from the group consisting of lower alkylamino-lower alkylcarbonyl, lower alkylcarbonyl-lower alkylcarbonyl, benzotriazolyl-carbonyl, hydroxyfluorenylcarbonyl, heterocyclylcarbonyl, pyrimidnylcarbonyl, halopyridylcarbonyl, pyridylcarbonyl, di(lower alkyl)amino substituted phenyl carbonyl, lower alkoxysubstituted cycloalkyl-carbonyl, phenyl-lower alkoxycarbonylamine-lower alkylcarbonyl, lower alkoxy-lower alkylcarbonyl, lower alkylcarbonylamino-lower alkenylcarbonyl, pyrrolidinyl-lower alkenylcarbonyl unsubstituted or hydroxy substituted, phenyl-lower alkenylcarbonyl, lower alkoxycarbonyl-lower alkylcarbonyl, thienylcarbonyl-lower alkylcarbonyl, hydroxy-halo-lower alkylcarbonyl, di(lower alkyl)aminocarbonyl-lower alkylcarbonyl, lower alkylcarbonyl, lower cycloalkyl-lower alkylcarbonyl, lower alkenylcarbonyl, phenylcarbonyl-lower alkylcarbonyl, lower alkyl substituted phenyl carbonyl-lower alkylcarbonyl, lower cycloalkylcarbonyl, lower alkoxy-lower alkoxy-lower alkoxy-lower alkylcarbonyl, di(lower alkoxy)phosphinyl-lower alkylcarbonyl, piperidinyl-carbonyl, lower bicycloalkylcarbonyl, imidazolyl-lower alkylcarbonyl, lower alkynylcarbonyl, (di(halo-lower alkyl-lower cycloalkyl)carbonyl, phenyl-lower alkoxy-lower alkylcarbonyl, cycloloweralkyl carbonyl wherein the cycloloweralkyl group is unsubstituted or substituted with one to three substituents selected from the group consisting of lower alkyl and lower alkyl carbonyl, pyranylcarbonyl, lower alkylthio-lower alkylcarbonyl, halo-lower alkylcarbonyl, heptenylcarbonyl, naphthyl-lower alkylcarbonyl, phenylcarbonyl-amino-lower alkylcarbonyl, lower alkylcarbonylamino-lower alkylcarbonyl, nitrosubstituted phenylcarbonyl-lower alkylcarbonyl, pyrimidinylthio-lower alkylcarbonyl, nitrosubstituted phenylcarbonyl-amino-lower alkylcarbonyl, phenylaminocarbonyloxy-lower alkylcarbonyl, lower alkyl thienyl carbonyl, phenyl lower cycloalkyl-carbonyl, nitrophenyl-lower alkylcarbonyl, thienylcarbonyl-lower alkylcarbonyl, lower alkylcarbonyl, and lower alkyl substituted phenoxy-lower alkylcarbonyl.

206. The compound of claim 205 wherein $R^{10}$ is lower alkylamino-lower alkylcarbonyl.

207. The compound of claim 206 which is 3(S)-[[N-[N-[N-[N-[N-(N,N-dimethylglycyl)-L-seryl]-O-benzyl-D-seryl]-2-methyl-L-phenylalanyl]-3-methyl-L-valyl]-L-leucyl]amino]-2-oxoheptanamide.

208. The compound of claim 205 wherein $R^{10}$ is lower alkylcarbonyl-lower alkylcarbonyl.

209. The compound of claim 208 which is 3(S)-[[N-[N-[N-[N-[N-(3-acetylpropionyl)-L-seryl]-O-benzyl-D-seryl]-2-methyl-L-phenylalanyl]-3-methyl-L-valyl]-L-leucyl]amino]-2-oxoheptanamide.

210. The compound of claim 205 wherein $R^{10}$ is benzotriazolyl-carbonyl.

211. The compound of claim 210 which is 3(S)-[[N-[N-[N-[N-[N-[(5-benzotriazolyl)carbonyl]-L-seryl]-O-benzyi-D-seryl]-2-methyl-L-phenylalanyl]-3-methyl-L-valyl]-L-leucyl]amino]-2-oxoheptanamide.

212. The compound of claim 205 wherein $R^{10}$ is hydroxy-fluorenylcarbonyl.

213. The compound of claim 212 which is 3(S)-[[N-[N-[N-[N-[N-[(9-hydroxy-9-fluorenyl)carbonyl]-L-seryl]-O-benzyl-D-seryl]-2-methyl-L-phenylalanyl]-3-methyl-L-valyl]-L-leucyl]amino]-2-oxoheptanamide.

214. The compound of claim 205 wherein $R^{10}$ is pyrimidinylcarbonyl.

215. The compound of claim 214 which is 3(S)-[[N-[N-[N-[N-[N-[(hexahydro-2,6-dioxo-4(S)-pyrimidinyl)carbonyl]-L-seryl]-O-benzyl-D-seryl]-2-methyl-L-phenylalanyl]-3-methyl-L-valyl]-L-leucyl]amino]-2-oxoheptanamide.

216. The compound of claim 205 wherein $R^{10}$ is halopyridylcarbonyl.

217. The compound of claim 216 which is 3(S)-[[N-[N-[N-[N-[N-[(2-chloro-3-pyridyl)carbonyl]-L-seryl]-O-benzyl-D-seryl]-2-methyl-L-phenylalanyl]-3-methyl-L-valyl]-L-leucyl]amino]-2-oxoheptanamide.

218. The compound of claim 205 wherein $R^{10}$ is di(lower alkyl) amino substituted phenyl carbonyl.

219. The compound of claim 218 which is 3(S)-[[N-[N-[N-[N-[N-[2-(dimethylamino)benzoyl]-L-seryl]-O-benzyl-D-seryl]-2-methyl-L-phenylalanyl]-3-methyl-L-valyl]-L-leucyl]amino]-2-oxoheptanamide.

220. The compound of claim 205 wherein $R^{10}$ is lower alkoxy substituted cycloalkylcarbonyl.

221. The compound of claim 220 which is 3(S)-[[N-[N-[N-[N-[N-[(3-methoxy-3(RS)-cyclohexyl)carbonyl]-L-seryl]-O-benzyl-D-seryl]-2-methyl-L-phenylalanyl]-3-methyl-L-valyl]-L-leucyl]amino]-2-oxoheptanamide.

222. The compound of claim 205 wherein $R^{10}$ is phenyl-lower alkoxycarbonylamine-lower alkylcarbonyl.

223. The compound of claim 222 which is 3(S)-[[N-[N-[N-[N-[N-[4-(benzyloxyformamido)butyryl]-L-seryl]-O-benzyl-D-seryl]-2-methyl-L-phenylalanyl]-3-methyl-L-valyl]-L-leucyl]amino]-2-oxoheptanamide.

224. The compound of claim 205 wherein $R^{10}$ is lower alkoxy-lower alkylcarbonyl.

225. The compound of claim 224 which is 3(S)-[[N-[N-[N-[N-[N-[2-(ethoxy)acetyl]-L-seryl]-O-benzyl-D-seryl]-2-methyl-L-phenylalanyl]-3-methyl-L-valyl]-L-leucyl]amino]-2-oxoheptanamide.

226. The compound of claim 205 wherein $R^{10}$ is lower alkylcarbonylamino-lower alkenylcarbonyl.

227. The compound of claim 226 which is 3(S)-[[N-[N-[N-[N-[N-(N-acetyl-DL-allylglycyl)-L-seryl]-O-benzyl-D-seryl]-2-methyl-L-phenylalanyl]-3-methyl-L-valyl]-L-leucyl]amino]-2-oxoheptanamide.

228. The compound of claim 205 wherein $R^{10}$ is unsubstituted or hydroxy substituted pyrrolidinyl-lower alkenylcarbonyl.

229. The compound of claim 228 which is 3(S)-[[N-[N-[N-[N-[N-(N-acetyl-4(S)-hydroxy-L-prolyl)-L-seryl]-O-benzyl-D-seryl]-2-methyl-L-phenylalanyl]-3-methyl-L-valyl]-L-leucyl]amino]-2-oxoheptanamide.

230. The compound of claim 228 which is 3(S)-[[N-[N-[N-[N-[N-(5-oxo-L-prolyl)-L-seryl]-O-benzyl-D-seryl]-2-methyl-L-phenylalanyl]-3-methyl-L-valyl]-L-leucyl]amino]-2-oxoheptanamide.

231. The compound of claim 205 wherein $R^{10}$ is phenyl-lower alkenylcarbonyl.

232. The compound of claim 231 which is(E)-3(S)-[[N-[N-[N-[N-[N-(4-phenyl-3-butenoyl)-L-seryl]-O-benzyl-D-seryl]-2-methyl-L-phenylalanyl]-3-methyl-L-valyl]-L-leucyl]amino]-2-oxoheptanamide.

233. The compound of claim 205 wherein $R^{10}$ is lower alkoxycarbonyl-lower alkylcarbonyl.

234. The compound of claim 233 which is 3(S)-[[N-[N-[N-[N-[N-[4-(methoxycarbonyl)butyryl]-L-seryl]-O-benzyl-D-seryl]-2-methyl-L-phenylalanyl]-3-methyl-L-valyl]-L-leucyl]amino]-2-oxoheptanamide.

235. The compound of claim 205 wherein $R^{10}$ is thienylcarbonyl-lower alkylcarbonyl.

236. The compound of claim 235 which is 3(S)-[[N-[N-[N-[N-[N-[3-(2-thenoyl)propionyl]-L-seryl]-O-benzyl-D-seryl]-2-methyl-L-phenylalanyl]-3-methyl-L-valyl]-L-leucyl]amino]-2-oxoheptanamide.

237. The compound of claim 205 wherein $R^{10}$ is hydroxy-halo-lower alkylcarbonyl.

238. The compound of claim 237 which is 3(S)-[[N-[N-[N-[N-[N-(4,4,4-trifluoro-3-hydroxy-3-methylbutyryl)-L-seryl]-O-benzyl-D-seryl]-2-methyl-L-phenylalanyl]-3-methyl-L-valyl]-L-leucyl]amino]-2-oxoheptanamide.

239. The compound of claim 205 wherein $R^{10}$ is di(lower alkyl)aminocarbonyl-lower alkylcarbonyl.

240. The compound of claim 239 which is 3(S)-[[N-[N-[N-[N-[N-[3-(dimethylcarbamoyl)propionyl]-L-seryl]-O-benzyl-D-seryl]-2-methyl-L-phenylalanyl]-3-methyl-L-valyl]-L-leucyl]amino]-2-oxoheptanamide.

241. The compound of claim 205 wherein $R^{10}$ is lower alkylcarbonyl or heterocyclylcarbonyl.

242. The compound of claim 241 which is 3(S)-[[N-[N-[N-[N-[N-[(-camphanyl)carbonyl]-L-seryl]-O-benzyl-D-seryl]-2-methyl-L-phenylalanyl]-3-methyl-L-valyl]-L-leucyl]amino]-2-oxoheptanamide.

243. The compound of claim 1, which is

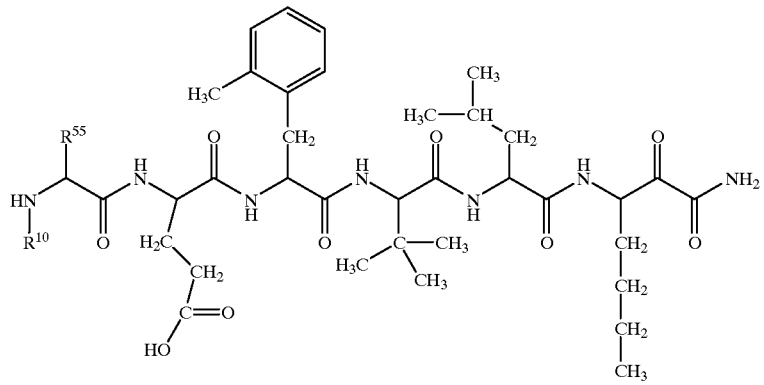

(XXXVI)

wherein $R^{10}$ is selected from the group consisting of lower alkylamino-lower alkylcarbonyl, lower alkylcarbonyl-lower alkylcarbonyl, heterocyclylcarbonyl wherein the heterocylic ring contains from four to twelve ring atoms with one of said ring atoms being a hetero atom selected from the group consisting of O, S and N, a five or six member heteroaryl ring-carbonyl, wherein the five or six member heteroaryl ring contains one or two heteroatoms independently selected from the group consisting of N, O, and S, hydroxyfluorenylcarbonyl, heterocycylcarbonyl, di(lower alkyl)amino substituted aryl carbonyl, lower alkoxy substituted cycloalkylcarbonyl, aryl-lower alkoxycarbonylamino-lower alkylcarbonyl, lower alkoxy-lower alkylcarbonyl, lower alkylcarbonylamino-lower alkenylcarbonyl, aryl-lower alkenylcarbonyl, lower alkoxycarbonyl-lower alkylcarbonyl, lower alkyl heteroarylcarbonyl wherein said heteroaryl is a five or six member heteroaryl ring containing one or two heteroatoms independently selected from the group consisting of N, O, and S, heteroaryl carbonyl-lower alkylcarbonyl, hydroxy-halo-lower alkylcarbonyl, di(lower alkyl)aminocarbonyl-lower alkylcarbonyl, lower alkylcarbonyl, lower cycloalkyl-lower alkylcarbonyl, lower alkenylcarbonyl, arylcarbonyl-lower alkylcarbonyl, lower alkyl substituted aryl carbonyl-lower alkylcarbonyl, lower alkoxy-lower alkoxy-lower alkoxy-lower alkylcarbonyl, di(lower alkoxy) phosphinyl-lower alkylcarbonyl, cycloloweralkylcarbonyl, a five or six member heteroaryl ring-lower alkyl or lower alkenyl carbonyl, wherein the five or six member heteroaryl ring contains one or two heteroatoms independently selected from the group consisting of N, O, and S and can be unsubstituted or hydroxy substituted, lower alkynylcarbonyl, (di(halo-lower alkyl-lower cycloalkyl)carbonyl, lower alkylthio-lower alkylcarbonyl, unsubstituted or nitro substituted arylcarbonyl-amino-lower alkylcarbonyl, lower alkylcarbonylamino-lower alkylcarbonyl, arylaminocarbonyl-lower alkylcarbonyl, a lower alkyl substituted five or six member heteroaryl ring-thio-lower alkylcarbonyl, wherein the five or six member heteroaryl ring contains one or two heteroatoms independently selected from the group consisting of N, O, and S, cycloloweralkyl carbonyl wherein the cycloloweralkyl group is unsubstituted or substituted with one to three substituents selected from the group consisting of lower alkyl and lower alkylcarbonyl, aryl lower cycloalkyl-carbonyl, nitroaryl-lower alkylcarbonyl, lower alkylcarbonyl, and lower alkyl substituted phenoxy-lower alkylcarbonyl; and $R^{55}$ is $CH_2COOH$ or $CH_2OH$.

244. The compound of claim 243 wherein $R^{10}$ is selected from the group consisting of lower alkylamino-lower alkylcarbonyl, lower alkylcarbonyl-lower alkylcarbonyl, benztriazoyl-carbonyl, hydroxyfluorenylcarbonyl, heterocyclylcarbonyl, pyrimidnylcarbonyl, halo-pyridylcarbonyl, pyridylcarbonyl, di(lower alkyl)amino substituted phenyl carbonyl, lower alkoxy substituted cycloalkylcarbonyl, phenyl-lower alkoxycarbonylamine-lower alkylcarbonyl, lower alkoxy-lower alkylcarbonyl, lower alkylcarbonylamino-lower alkenylcarbonyl, pyrrolidinyl-lower alkenylcarbonyl unsubstituted or hydroxy substituted, phenyl-lower alkenylcarbonyl, lower alkoxycarbonyl-lower alkylcarbonyl, thienylcarbonyl-lower alkylcarbonyl, hydroxy-halo-lower alkylcarbonyl, di(lower alkyl)aminocarbonyl-lower alkylcarbonyl, lower alkylcarbonyl, lower cycloalkyl-lower alkylcarbonyl, lower alkenylcarbonyl, phenylcarbonyl-lower alkylcarbonyl, lower alkyl substituted phenyl carbonyl-lower alkylcarbonyl, lower cycloalkylcarbonyl, lower alkoxy-lower alkoxy-lower alkoxy-lower alkylcarbonyl, di(lower alkoxy)phosphinyl-lower alkylcarbonyl, piperidinyl-carbonyl, lower bicycloalkylcarbonyl, imidazolyl-lower alkylcarbonyl, lower alkynylcarbonyl, (di(halo-lower alkyl-lower cycloalkyl)carbonyl, phenyl-lower alkoxy-lower alkylcarbonyl, cycloloweralkylcarbonyl wherein the cycloloweralkyl group is unbsubstituted or substituted with one to three substituents selected from the group consisting of lower alkyl and lower alkylcarbonyl, pyranylcarbonyl, lower alkylthio-lower alkylcarbonyl, halo-lower alkylcarbonyl, heptenylcarbonyl, naphthyl-lower alkylcarbonyl, phenylcarbonyl-amino-lower alkylcarbonyl, lower alkylcarbonylamino-lower alkylcarbonyl, phenylaminocarbonyl-lower alkylcarbonyl, pyrimidinylthio-lower alkylcarbonyl, nitro substituted phenylcarbonyl-amino- lower alkylcarbonyl, a lower alkyl substituted five or six member heteroaryl ring-thio-lower alkylcarbonyl, wherein the five or six member heteroaryl ring contains one or two heteroatoms independently selected from the group consisting of N, O, and S, phenylaminocarbonyloxy-lower alkylcarbonyl, lower alkyl thienyl carbonyl, phenyl lower cycloalkyl-carbonyl, nitrophenyl-lower alkylcarbonyl, thienylcarbonyl-lower alkylcarbonyl, lower alkylcarbonyl, and lower alkyl substituted phenoxy-lower alkylcarbonyl.

245. The compound of claim 244 wherein $R^{10}$ is heterocyclylcarbonyl or lower alkylcarbonyl.

246. The compound of claim 245 which is 3(S)-[[N-[N-[N-[N-[N-(methylcarbonyl)-L-α-aspartyl]-L-α-glutamyl]-2-methyl-L-phenylalanyl]-3-methyl-L-valyl]-L-leucyl]amino]-2-oxoheptanamide.

247. The compound of claim 244 wherein $R^{10}$ is pyrimidinylcarbonyl.

248. The compound of claim 247 which is 3(S)-[[N-[N-[N-[N-[N-[(2,6-dioxo-4-pyrimidinyl)carbonyl]-L-α-aspartyl]-L-α-glutamyl]-2-methyl-L-phenylalanyl]-3-methyl-L-valyl]-L-leucyl]amino]-2-oxoheptanamide.

249. The compound of claim 247 which is 3(S)-[[N-[N-[N-[N-[N-[(2,4-dioxo-5-pyrimidinyl)carbonyl]-L-α-aspartyl]-L-α-glutamyl]-2-methyl-L-phenylalanyl]-3-methyl-L-valyl]-L-leucyl]amino]-2-oxoheptanamide.

250. The compound of claim 244 wherein $R^{10}$ is lower cycloalkyl-lower alkylcarbonyl.

251. The compound of claim 250 which is 3(S)-[[N-[N-[N-[N-[N-[(4-tert-butylcyclohexyl)carbonyl]-L-α-aspartyl]-L-α-glutamyl]-2-methyl-L-phenylalanyl]-3-methyl-L-valyl]-L-leucyl]amino]-2-oxoheptanamide.

252. The compound of claim 250 which is 3(S)-[[N-[N-[N-[N-[N-(2-cyclohexylacetyl)-L-α-aspartyl]-L-α-glutamyl]-2-methyl-L-phenylalanyl]-3-methyl-L-valyl]-L-leucyl]amino]-2-oxoheptanamide.

253. The compound of claim 250 which is 3(S)-[[N-[N-[N-[N-[N-(tetrahydro-3-furoyl)-L-α-aspartyl]-L-α-glutamyl]-2-methyl-L-phenylalanyl]-3-methyl-L-valyl]-L-leucyl]amino]-2-oxoheptanamide.

254. The compound of claim 244 wherein $R^{10}$ is lower alkenylcarbonyl.

255. The compound of claim 254 which is 3(S)-[[N-[N-[N-[N-[N-(3-pentenoyl)-L-α-aspartyl]-L-α-glutamyl]-2-methyl-L-phenylalanyl]-3-methyl-L-valyl]-L-leucyl]amino]-2-oxoheptanamide.

256. The compound of claim 244 wherein $R^{10}$ is phenylcarbonyl-lower alkylcarbonyl.

257. The compound of claim 256 which is 3(S)-[[N-[N-[N-[N-[N-(4-benzoylbutyryl)-L-α-aspartyl]-L-α-glutamyl]-2-methyl-L-phenylalanyl]-3-methyl-L-valyl]-L-leucyl]amino]-2-oxoheptanamide.

258. The compound of claim 244 wherein $R^{10}$ is lower alkyl substituted phenyl carbonyl-lower alkylcarbonyl.

259. The compound of claim 258 which is 3(S)-[[N-[N-[N-[N-[N-[3-(4-methylbenzoyl)propionyl]-L-α-aspartyl]-L-α-glutamyl]-2-methyl-L-phenylalanyl]-3-methyl-L-valyl]-L-leucyl]amino]-2-oxoheptanamide].

260. The compound of claim 244 wherein $R^{10}$ is lower cycloalkylcarbonyl containing from 3 to 12 carbon atoms.

261. The compound of claim 260 which is 3(S)-[[N-[N-[N-[N-[N-(cyclopropylcarbonyl)-L-α-aspartyl]-L-α-glutamyl]-2-methyl-L-phenylalanyl]-3-methyl-L-valyl]-L-leucyl]amino]-2-oxoheptanamide.

262. The compound of claim 244 wherein $R^{10}$ is lower alkoxy lower alkoxy-lower alkoxy-lower alkylcarbonyl.

263. The compound of claim 262 which is 3(S)-[[N-[N-[N-[N-[N-[2-[2-(2-methoxyethoxy)ethoxy]acetyl]-L-α-aspartyl]-L-α-glutamyl]-2-methyl-L-phenylalanyl]-3-methyl-L-valyl]-L-leucyl]amino]-2-oxoheptanamide.

264. The compound of claim 244 wherein $R^{10}$ is di(lower alkoxy)phosphinyl-lower alkylcarbonyl.

265. The compound of claim 264 which is 3(S)-[[N-[N-[N-[N-[N-[2-(diethoxyphosphinyl)acetyl]-L-α-aspartyl]-L-α-glutamyl]-2-methyl-L-phenylalanyl]-3-methyl-L-valyl]-L-leucyl]amino]-2-oxoheptanamide.

266. The compound of claim 244 wherein $R^{10}$ is piperidinyl-carbonyl.

267. The compound of claim 266 which is 3(S)-[[N-[N-[N-[N-[N-[(1-acetyl-4-piperidinyl)carbonyl]-L-α-aspartyl]-L-α-glutamyl]-2-methyl-L-phenylalanyl]-3-methyl-L-valyl]-L-leucyl]amino]-2-oxoheptanamide.

268. The compound of claim 244 wherein $R^{10}$ is lower tricycloalkylcarbonyl.

269. The compound of claim 268 which is 3(S)-[[N-[N-[N-[N-[N-[(1-adamantyl)carbonyl]-L-α-aspartyl]-L-α-glutamyl]-2-methyl-L-phenylalanyl]-3-methyl-L-valyl]-L-leucyl]amino]-2-oxoheptanamide.

270. The compound of claim 244 wherein $R^{10}$ is imidazolyl-lower alkylcarbonyl.

271. The compound of claim 270 which is 3(S)-[[N-[N-[N-[N-[N-[3-(2-methyl-4-nitro-1-imidazolyl)propionyl]-L-α-aspartyl]-L-α-glutamyl]-2-methyl-L-phenylalanyl]-3-methyl-L-valyl]-L-leucyl]amino]-2-oxoheptanamide.

272. The compound of claim 244 wherein $R^{10}$ is lower alkynylcarbonyl.

273. The compound of claim 272 which is 3(S)-[[N-[N-[N-[N-[N-(4-hexynoyl)-L-α-aspartyl]-L-α-glutamyl]-2-methyl-L-phenylalanyl]-3-methyl-L-valyl]-L-leucyl]amino]-2-oxoheptanamide.

274. The compound of claim 244 wherein $R^{10}$ is (dihalo-lower alkyl-lower cycloalkyl)carbonyl.

275. The compound of claim 274 which is 3(S)-[[N-[N-[N-[N-[N-[(2,2-dichloro-1-methyl-1-cyclopropyl)carbonyl]-L-α-aspartyl]-L-α-glutamyl]-2-methyl-L-phenylalanyl]-3-methyl-L-valyl]-L-leucyl]amino]-2-oxoheptanamide.

276. The compound of claim 244 wherein $R^{10}$ is lower alkyl substituted phenoxy-lower alkylcarbonyl.

277. The compound of claim 276 which is 3(S)-[[N-[N-[N-[N-[N-[2-(4-methylphenoxy)acetyl]-L-α-aspartyl]-L-α-glutamyl]-2-methyl-L-phenylalanyl]-3-methyl-L-valyl]-L-leucyl]amino]-2-oxoheptanamide.

278. The compound of claim 244 wherein $R^{10}$ is cycloloweralkyl carbonyl wherein the cycloloweralkyl group is unsubstituted or substituted with one to three substituents selected from the group consisting of lower alkyl and lower alkyl carbonyl.

279. The compound of claim 278 which is 3(S)-[[N-[N-[N-[N-[N-[2-(3-acetyl-2,2-dimethyl-1-cyclobutyl)acetyl]-L-α-aspartyl]-L-α-glutamyl]-2-methyl-L-phenylalanyl]-3-methyl-L-valyl]-L-leucyl]amino]-2-oxoheptanamide.

280. The compound of claim 244 wherein $R^{10}$ is pyranylcarbonyl.

281. The compound of claim 280 which is 3(S)-[[N-[N-[N-[N-[N-[(6-oxo-6H-pyran-3-yl)carbonyl]-L-α-aspartyl]-

L-α-glutamyl]-2-methyl-L-phenylalanyl]-3-methyl-L-valyl]-L-leucyl]amino]-2-oxoheptanamide.

282. The compound of claim 280 which is 3(S)-[[N-[N-[N-[N-[(4,5-dihydro-6,6-dimethyl-4-oxo-6H-pyran-2-yl)carbonyl]-L-α-aspartyl]-L-α-glutamyl]-2-methyl-L-phenylalanyl]-3-methyl-L-valyl]-L-leucyl]amino]-2-oxoheptanamide.

283. The compound of claim 244 wherein $R^{10}$ is lower alkylthio-lower alkylcarbonyl.

284. The compound of claim 283 which is 3(S)-[[N-[N-[N-[N-[2-(methanesulphonyl)acetyl]-L-α-aspartyl]-L-α-glutamyl]-2-methyl-L-phenylalanyl]-3-methyl-L-valyl]-L-leucyl]amino]-2-oxoheptanamide.

285. The compound of claim 244 wherein $R^{10}$ is halo-lower alkylcarbonyl.

286. The compound of claim 285 which is 3(S)-[[N-[N-[N-[N-[N-(4,4,4-trifluoro-3(RS)-methylbutyryl)-L-α-aspartyl]-L-α-glutamyl]-2-methyl-L-phenylalanyl]-3-methyl-L-valyl]-L-leucyl]amino]-2-oxoheptanamide.

287. The compound of claim 244 wherein $R^{10}$ heptenyl-carbonyl.

288. The compound of claim 287 which is 3(S)-[[N-[N-[N-[N-[(bicyclo[2.2.1]-5-heptenyl)carbonyl]-L-α-aspartyl]-L-α-glutamyl]-2-methyl-L-phenylalanyl]-3-methyl-L-valyl]-L-leucyl]amino]-2-oxoheptanamide.

289. The compound of claim 244 wherein $R^{10}$ is naphthyl-lower alkylcarbonyl.

290. The compound of claim 289 which is 3(S)-[[N-[N-[N-[N-[2-(2-naphthyl)acetyl]-L-α-aspartyl]-L-α-glutamyl]-2-methyl-L-phenylalanyl]-3-methyl-L-valyl]-L-leucyl]amino]-2-oxoheptanamide.

291. The compound of claim 244 wherein $R^{10}$ is phenylcarbonyl-amino-lower alkylcarbonyl.

292. The compound of claim 291 which is 3(S)-[[N-[N-[N-[N-(N-benzoyl-β-alanyl)-L-α-aspartyl]-L-α-glutamyl]-2-methyl-L-phenylalanyl]-3-methyl-L-valyl]-L-leucyl]amino]-2-oxoheptanamide.

293. The compound of claim 243 wherein $R^{10}$ is lower alkylcarbonylamino-lower alkylcarbonyl.

294. The compound of claim 293 which is 3(S)-[[N-[N-[N-[N-[4-(acetamido)butyryl]-L-α-aspartyl]-L-α-glutamyl]-2-methyl-L-phenylalanyl]-3-methyl-L-valyl]-L-leucyl]amino]-2-oxoheptanamide.

295. The compound of claim 244 wherein $R^{10}$ is phenylaminocarbonyl-lower alkylcarbonyl.

296. The compound of claim 295 which is 3(S)-[[N-[N-[N-[N-[4-(phenylcarbamoyl)butyryl]-L-α-aspartyl]-L-α-glutamyl]-2-methyl-L-phenylalanyl]-3-methyl-L-valyl]-L-leucyl]amino]-2-oxoheptanamide.

297. The compound of claim 244 wherein $R^{10}$ is pyrimidinylthio-lower alkylcarbonyl.

298. The compound of claim 297 which is 3(S)-[[N-[N-[N-[N-[2-[(4,6-dimethyl-2-pyrimidinyl)thio]acetyl]-L-α-aspartyl]-L-α-glutamyl]-2-methyl-L-phenylalanyl]-3-methyl-L-valyl]-L-leucyl]amino]-2-oxoheptanamide.

299. The compound of claim 244 wherein $R^{10}$ is nitro substituted phenylcarbonyl-amino-lower alkylcarbonyl.

300. The compound of claim 299 which is 3(S)-[[N-[N-[N-[N-(4-nitrobenzoyl)-β-alanyl]-L-α-aspartyl]-L-α-glutamyl]-2-methyl-L-phenylalanyl]-3-methyl-L-valyl]-L-leucyl]amino]-2-oxoheptanamide.

301. The compound of claim 244 wherein $R^{10}$ is phenylaminocarbonyloxy-lower alkylcarbonyl.

302. The compound of claim 301 which is 3(S)-[[N-[N-[N-[N-[2(S)-[(phenylcarbamoyl)oxy]propionyl]-L-α-aspartyl]-L-α-glutamyl]-2-methyl-L-phenylalanyl]-3-methyl-L-valyl]-L-leucyl]amino]-2-oxoheptanamide.

303. The compound of claim 244 wherein $R^{10}$ is lower alkyl thienyl carbonyl.

304. The compound of claim 303 which is 3(S)-[[N-[N-[N-[N-(3-methyl-2-thenoyl)-L-α-aspartyl]-L-α-glutamyl]-2-methyl-L-phenylalanyl]-3-methyl-L-valyl]-L-leucyl]amino]-2-oxoheptanamide.

305. The compound of claim 244 wherein $R^{10}$ is pyridyl-carbonyl.

306. The compound of claim 305 which is 3(S)-[[N-[N-[N-[N-[(1-oxido-2-pyridyl)carbonyl]-L-α-aspartyl]-L-α-glutamyl]-2-methyl-L-phenylalanyl]-3-methyl-L-valyl]-L-leucyl]amino]-2-oxoheptanamide.

307. The compound of claim 244 wherein $R^{10}$ is phenyl lower cycloalkyl-carbonyl.

308. The compound of claim 307 which is 3(S)-[[N-[N-[N-[N-[(1-phenyl-1-cyclopropyl)carbonyl]-L-α-aspartyl]-L-α-glutamyl]-2-methyl-L-phenylalanyl]-3-methyl-L-valyl]-L-leucyl]amino]-2-oxoheptanamide.

309. The compound of claim 244 wherein $R^{10}$ is nitrophenyl-lower alkylcarbonyl.

310. The compound of claim 309 which is 3(S)-[[N-[N-[N-[N-[2(RS)-(4-nitrophenyl)propionyl]-L-α-aspartyl]-L-α-glutamyl]-2-methyl-L-phenylalanyl]-3-methyl-L-valyl]-L-leucyl]amino]-2-oxoheptanamide.

311. The compound of claim 244 wherein $R^{10}$ is thienylcarbonyl-lower alkylcarbonyl.

312. The compound of claim 311 which is 3(S)-[[N-[N-[N-[N-[4-(2-thenoyl)butyryl]-L-α-aspartyl]-L-α-glutamyl]-2-methyl-L-phenylalanyl]-3-methyl-L-valyl]-L-leucyl]amino]-2-oxoheptanamide.

313. The compound of claim 244 wherein $R^{10}$ is lower alkylthioheteroarylcarbonyl.

314. The compound of claim 313 which is 3(S)-[[N-[N-[N-[N-[[(2-(ethylthio)-3-pyridyl]carbonyl]-L-α-aspartyl]-L-α-glutamyl]-2-methyl-L-phenylalanyl]-3-methyl-L-valyl]-L-leucyl]amino]-2-oxoheptanamide.

315. The compound of claim 244 wherein $R^{10}$ is phenyl-lower alkoxy carbonyl.

316. The compound of claim 315 which is 3(S)-[[N-[N-[N-[N-(benzyloxycarbonyl)-L-α-aspartyl]-L-α-glutamyl]-2-methyl-L-phenylalanyl]-3-methyl-L-valyl]-L-leucyl]amino]-2-oxoheptanamide.

317. The compound of claim 1 which is 3(S)-[[N-[N-[N-[N-[N-(3-carboxypropionyl)-L-prolyl-L-α-glutamyl]-2-methyl-L-phenylalanyl]-3-methyl-L-valyl]-L-leucyl]amino]-2-oxoheptanamide.

318. The compound of claim 1 which is 3(S)-[[N-[N-[N-[3-(3-carboxypropionyl)-4(S)-oxazolidinyl]carbonyl-L-α-glutamyl]-2-methyl-L-phenylalany'l]-3-methyl-L-valyl]-L-leucyl]amino]-2-oxoheptanamide.

319. The compound of claim 1 which is 3(S)-[[N-[N-[N-[N-[O-benzyl-N-(3-carboxypropionyl)-L-seryl]-L-α-glutamyl]-2-methyl-L-phenylalanyl]-3-methyl-L-valyl]-L-leucyl]amino]-2-oxoheptanamide.

320. The compound of claim 1 which is 3(S)-[[N-[N-[N-[N-[N2-(3-carboxypropionyl)-L-glutaminyl-L-α-glutamyl]-2-methyl-L-phenylalanyl]-3-methyl-L-valyl]-L-leucyl]amino]-2-oxoheptanamide.

\* \* \* \* \*

UNITED STATES PATENT AND TRADEMARK OFFICE
CERTIFICATE OF CORRECTION

PATENT NO. : 6,187,905 B1
DATED : February 13, 2001
INVENTOR(S) : David Nigel Hurst, Philip Stephen Jones, Paul Brttain Kay, Tony Michael Raynham, Francis Xavier Wilson Page 1 of 2

It is certified that error appears in the above-identified patent and that said Letters Patent is hereby corrected as shown below:

Column 78, claim 47,
Line 49, "-N-(2-thienl)" should be -- N-(2-thienyl) --

Column 79, claim 55,
Line 33, "phenyl-lower alky" should be -- phenyl-lower alkyl --
Line 34, "alkyl, oxazolyl-" should be -- alkyl, and oxazolyl --

Column 85, claim 122,
Line 61, "$R^1$" should be -- $R^5$ --

Column 87, claim 133,
Line 2, "formidamino-lower" should be -- formamido-lower --

Column 90, claim 187,
Line 50, "-L-α-g lutamyl]-" should be -- -L-α-glutamyl]- --

Column 93, claim 205,
Line 1, "pyrimidnylcarbonyl" should be -- pyrimidinylcarbonyl --

Column 93, claim 211,
Line 52, "-benzyi-" should be -- benzyl- --

Column 96, claim 244,
Line 47, "pyrimidnylcarbonyl," should be -- pyrimidinylcarbonyl, --

Column 96, claim 287,
Line 20, after "$R^{10}$" insert -- is --

UNITED STATES PATENT AND TRADEMARK OFFICE
CERTIFICATE OF CORRECTION

PATENT NO.    : 6,187,905 B1
DATED         : February 13, 2001
INVENTOR(S)   : David Nigel Hurst, Philip Stephen Jones, Paul Brttain Kay, Tony Michael Raynham, Francis Xavier Wilson It is certified that error appears in the above-identified patent and that said Letters Patent is hereby corrected as shown below:

<u>Column 100, claim 318,</u>
Line 52, "-L-phenylany'l]-3-" should be -- -L-phenylanyl]-3- --

Signed and Sealed this

Twenty-sixth Day of March, 2002

*Attest:*

JAMES E. ROGAN
*Attesting Officer*        *Director of the United States Patent and Trademark Office*